(12) United States Patent
Shults et al.

(10) Patent No.: US 7,860,545 B2
(45) Date of Patent: *Dec. 28, 2010

(54) ANALYTE MEASURING DEVICE

(75) Inventors: Mark C. Shults, Madison, WI (US); James H. Brauker, Cement City, MI (US); Victoria Carr-Brendel, Pleasanton, CA (US); Mark A. Tapsak, Orangeville, PA (US); Dubravka Markovic, San Diego, CA (US); Stuart J. Updike, Madison, WI (US); Rathbun K. Rhodes, Madison, WI (US)

(73) Assignee: DexCom, Inc., San Diego, CA (US)

( * ) Notice: Subject to any disclaimer, the term of this patent is extended or adjusted under 35 U.S.C. 154(b) by 85 days.

This patent is subject to a terminal disclaimer.

(21) Appl. No.: 12/037,812

(22) Filed: Feb. 26, 2008

(65) Prior Publication Data

US 2008/0228051 A1    Sep. 18, 2008

Related U.S. Application Data

(60) Division of application No. 10/846,150, filed on May 14, 2004, which is a continuation-in-part of application No. 10/647,065, filed on Aug. 22, 2003, now Pat. No. 7,192,450.

(60) Provisional application No. 60/472,673, filed on May 21, 2003, provisional application No. 60/544,722, filed on Feb. 12, 2004.

(51) Int. Cl.
*A61B 5/00* (2006.01)
(52) U.S. Cl. .................................... 600/347; 600/365
(58) Field of Classification Search ....................... None
See application file for complete search history.

(56) References Cited

U.S. PATENT DOCUMENTS 3,775,182 A    11/1973    Patton et al.

(Continued)

FOREIGN PATENT DOCUMENTS

EP    0 098 592    1/1984

(Continued)

OTHER PUBLICATIONS

Abel et al. 2002. Biosensors for in vivo glucose measurement: can we cross the experimental stage. Biosens Bioelectron 17:1059-1070.

(Continued)

*Primary Examiner*—Robert L Nasser
(74) *Attorney, Agent, or Firm*—Knobbe Martens Olson & Bear LLP

(57) ABSTRACT

An implantable analyte-measuring device including a membrane adapted to promote vascularization and/or interfere with barrier cell layer formation. The membrane includes any combination of materials, architecture, and bioactive agents that facilitate analyte transport to provide long-term in vivo performance of the implantable analyte-measuring device.

7 Claims, 16 Drawing Sheets

U.S. PATENT DOCUMENTS

| | | | |
|---|---|---|---|
| 3,898,984 A | 8/1975 | Mandel et al. |
| 3,929,971 A | 12/1975 | Roy |
| 3,943,918 A | 3/1976 | Lewis |
| 3,964,974 A | 6/1976 | Banauch et al. |
| 3,966,580 A | 6/1976 | Janata et al. |
| 4,024,312 A | 5/1977 | Korpman |
| 4,040,908 A | 8/1977 | Clark, Jr. |
| 4,073,713 A | 2/1978 | Newman |
| 4,076,656 A | 2/1978 | White et al. |
| 4,172,770 A | 10/1979 | Semersky et al. |
| 4,197,840 A | 4/1980 | Beck et al. |
| 4,215,703 A | 8/1980 | Willson |
| 4,225,410 A | 9/1980 | Pace |
| 4,240,889 A | 12/1980 | Yoda et al. |
| 4,253,469 A | 3/1981 | Aslan |
| 4,255,500 A | 3/1981 | Hooke |
| 4,259,540 A | 3/1981 | Sabia |
| 4,260,725 A | 4/1981 | Keogh et al. |
| 4,353,888 A | 10/1982 | Sefton |
| 4,374,013 A | 2/1983 | Enfors |
| 4,388,166 A | 6/1983 | Suzuki et al. |
| 4,403,984 A | 9/1983 | Ash et al. |
| 4,415,666 A | 11/1983 | D'Orazio et al. |
| 4,418,148 A | 11/1983 | Oberhardt |
| 4,431,004 A | 2/1984 | Bessman et al. |
| 4,436,094 A | 3/1984 | Cerami |
| 4,442,841 A | 4/1984 | Uehara et al. |
| 4,477,314 A | 10/1984 | Richter et al. |
| 4,484,987 A | 11/1984 | Gough |
| 4,494,950 A | 1/1985 | Fischell |
| 4,506,680 A | 3/1985 | Stokes |
| RE31,916 E | 6/1985 | Oswin et al. |
| 4,534,355 A | 8/1985 | Potter |
| 4,554,927 A | 11/1985 | Fussell |
| 4,571,292 A | 2/1986 | Liu et al. |
| 4,577,642 A | 3/1986 | Stokes |
| 4,650,547 A | 3/1987 | Gough |
| 4,663,824 A | 5/1987 | Kenmochi |
| 4,671,288 A | 6/1987 | Gough |
| 4,680,268 A | 7/1987 | Clark, Jr. |
| 4,686,044 A | 8/1987 | Behnke et al. |
| 4,689,309 A | 8/1987 | Jones |
| 4,702,732 A | 10/1987 | Powers et al. |
| 4,703,756 A | 11/1987 | Gough et al. |
| 4,711,251 A | 12/1987 | Stokes |
| 4,721,677 A | 1/1988 | Clark |
| 4,753,652 A | 6/1988 | Langer et al. |
| 4,757,022 A | 7/1988 | Shults et al. |
| 4,759,828 A | 7/1988 | Young et al. |
| 4,776,944 A | 10/1988 | Janata et al. |
| 4,781,798 A | 11/1988 | Gough |
| 4,787,398 A | 11/1988 | Garcia et al. |
| 4,803,243 A | 2/1989 | Fujimoto et al. |
| 4,810,470 A | 3/1989 | Burkhardt et al. |
| 4,823,808 A | 4/1989 | Clegg et al. |
| 4,852,573 A | 8/1989 | Kennedy |
| 4,861,830 A | 8/1989 | Ward, Jr. |
| 4,871,440 A | 10/1989 | Nagata et al. |
| 4,883,057 A | 11/1989 | Broderick |
| 4,889,744 A | 12/1989 | Quaid |
| 4,890,620 A | 1/1990 | Gough |
| 4,902,294 A | 2/1990 | Gosserez |
| 4,927,407 A | 5/1990 | Dorman |
| 4,935,345 A | 6/1990 | Guilbeau et al. |
| 4,953,552 A | 9/1990 | DeMarzo |
| 4,963,595 A | 10/1990 | Ward et al. |
| 4,970,145 A | 11/1990 | Bennetto et al. |
| 4,984,929 A | 1/1991 | Rock et al. |
| 4,986,271 A | 1/1991 | Wilkins |
| 4,986,671 A | 1/1991 | Sun et al. |
| 4,994,167 A | 2/1991 | Shults et al. |
| 5,002,572 A | 3/1991 | Picha |
| 5,007,929 A | 4/1991 | Quaid |
| 5,050,612 A | 9/1991 | Matsumura |
| 5,059,654 A | 10/1991 | Hou et al. |
| 5,067,491 A | 11/1991 | Taylor, II et al. |
| 5,101,814 A | 4/1992 | Palti |
| 5,113,871 A | 5/1992 | Viljanto et al. |
| 5,130,231 A | 7/1992 | Kennedy et al. |
| 5,137,028 A | 8/1992 | Nishimura |
| 5,165,407 A | 11/1992 | Wilson et al. |
| 5,171,689 A | 12/1992 | Kawaguri et al. |
| 5,190,041 A | 3/1993 | Palti |
| 5,222,980 A | 6/1993 | Gealow |
| 5,235,003 A | 8/1993 | Ward et al. |
| 5,249,576 A | 10/1993 | Goldberger et al. |
| 5,264,104 A | 11/1993 | Gregg et al. |
| 5,269,891 A | 12/1993 | Colin |
| 5,271,736 A | 12/1993 | Picha |
| 5,282,848 A | 2/1994 | Schmitt |
| 5,285,513 A | 2/1994 | Kaufman et al. |
| 5,299,571 A | 4/1994 | Mastrototaro |
| 5,304,468 A | 4/1994 | Phillips et al. |
| 5,310,469 A | 5/1994 | Cunningham et al. |
| 5,314,471 A | 5/1994 | Brauker et al. |
| 5,316,008 A | 5/1994 | Suga et al. |
| 5,321,414 A | 6/1994 | Alden et al. |
| 5,322,063 A | 6/1994 | Allen et al. |
| 5,326,356 A | 7/1994 | Della Valle et al. |
| 5,330,521 A | 7/1994 | Cohen |
| 5,331,555 A | 7/1994 | Hashimoto et al. |
| 5,340,352 A | 8/1994 | Nakanishi et al. |
| 5,342,409 A | 8/1994 | Mullett |
| 5,343,869 A | 9/1994 | Pross et al. |
| 5,344,451 A | 9/1994 | Dayton |
| 5,344,454 A | 9/1994 | Clarke et al. |
| 5,348,788 A | 9/1994 | White |
| 5,356,786 A | 10/1994 | Heller et al. |
| 5,368,028 A | 11/1994 | Palti |
| 5,372,133 A | 12/1994 | Hogen Esch |
| 5,380,536 A | 1/1995 | Hubbell et al. |
| 5,382,514 A | 1/1995 | Passaniti et al. |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney, II et al. |
| 5,397,848 A | 3/1995 | Yang et al. |
| 5,411,647 A | 5/1995 | Johnson et al. |
| 5,417,395 A | 5/1995 | Fowler et al. |
| 5,421,923 A | 6/1995 | Clarke et al. |
| 5,428,123 A | 6/1995 | Ward et al. |
| 5,431,160 A | 7/1995 | Wilkins |
| 5,431,921 A | 7/1995 | Thombre |
| 5,443,508 A | 8/1995 | Giampapa |
| 5,453,278 A | 9/1995 | Chan et al. |
| 5,458,631 A | 10/1995 | Xavier |
| 5,462,051 A | 10/1995 | Oka et al. |
| 5,462,064 A | 10/1995 | D'Angelo et al. |
| 5,469,846 A | 11/1995 | Khan |
| 5,476,094 A | 12/1995 | Allen et al. |
| 5,480,711 A * | 1/1996 | Ruefer ............... 428/315.5 |
| 5,484,404 A | 1/1996 | Schulman et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,507,288 A | 4/1996 | Bocker et al. |
| 5,512,055 A | 4/1996 | Domb et al. |
| 5,513,636 A | 5/1996 | Palti |
| 5,529,066 A | 6/1996 | Palti |
| 5,531,878 A | 7/1996 | Vadgama et al. |
| 5,538,511 A | 7/1996 | Van Antwerp |
| 5,540,828 A | 7/1996 | Yacynych |
| 5,545,220 A | 8/1996 | Andrews et al. |

| | | | | | | |
|---|---|---|---|---|---|---|
| 5,545,223 A | 8/1996 | Neuenfeldt et al. | | 5,957,854 A | 9/1999 | Besson et al. |
| 5,549,675 A | 8/1996 | Neuenfeldt et al. | | 5,957,903 A | 9/1999 | Mirzaee et al. |
| 5,564,439 A | 10/1996 | Picha | | 5,964,261 A | 10/1999 | Neuenfeldt et al. |
| 5,568,806 A | 10/1996 | Cheney, II et al. | | 5,964,804 A | 10/1999 | Brauker et al. |
| 5,569,186 A | 10/1996 | Lord et al. | | 5,964,993 A | 10/1999 | Blubaugh et al. |
| 5,569,462 A | 10/1996 | Martinson et al. | | 5,965,125 A | 10/1999 | Mineau-Hanschke |
| 5,571,395 A | 11/1996 | Park et al. | | 5,965,380 A | 10/1999 | Heller et al. |
| 5,575,930 A | 11/1996 | Tietje-Girault et al. | | 5,967,986 A | 10/1999 | Cimochowski et al. |
| 5,578,463 A | 11/1996 | Berka et al. | | 5,976,085 A | 11/1999 | Kimball et al. |
| 5,582,184 A | 12/1996 | Erickson et al. | | 5,985,129 A | 11/1999 | Gough et al. |
| 5,584,876 A | 12/1996 | Bruchman et al. | | 5,999,848 A | 12/1999 | Gord et al. |
| 5,586,553 A | 12/1996 | Halili et al. | | 6,001,067 A * | 12/1999 | Shults et al. ............... 600/584 |
| 5,589,563 A | 12/1996 | Ward et al. | | 6,001,471 A | 12/1999 | Bries et al. |
| 5,590,651 A | 1/1997 | Shaffer et al. | | 6,011,984 A | 1/2000 | Van Antwerp et al. |
| 5,593,440 A | 1/1997 | Brauker et al. | | 6,013,113 A | 1/2000 | Mika |
| 5,593,852 A | 1/1997 | Heller et al. | | 6,016,448 A | 1/2000 | Busacker et al. |
| 5,624,537 A | 4/1997 | Turner et al. | | 6,049,727 A | 4/2000 | Crothall |
| 5,628,890 A | 5/1997 | Carter et al. | | 6,063,637 A | 5/2000 | Arnold et al. |
| 5,640,954 A | 6/1997 | Pfeiffer et al. | | 6,081,736 A | 6/2000 | Colvin et al. |
| 5,653,756 A | 8/1997 | Clarke et al. | | 6,083,710 A | 7/2000 | Heller et al. |
| 5,653,863 A | 8/1997 | Genshaw et al. | | 6,088,608 A | 7/2000 | Schulman et al. |
| 5,658,330 A | 8/1997 | Carlisle et al. | | 6,093,172 A | 7/2000 | Funderburk et al. |
| 5,660,163 A | 8/1997 | Schulman et al. | | 6,103,033 A | 8/2000 | Say et al. |
| 5,683,562 A | 11/1997 | Schaffar et al. | | 6,115,634 A | 9/2000 | Donders et al. |
| 5,686,829 A | 11/1997 | Girault | | 6,119,028 A | 9/2000 | Schulman et al. |
| 5,695,623 A | 12/1997 | Michel et al. | | 6,121,009 A | 9/2000 | Heller et al. |
| 5,697,976 A | 12/1997 | Chesterfield et al. | | 6,122,536 A | 9/2000 | Sun et al. |
| 5,704,354 A | 1/1998 | Preidel et al. | | 6,134,461 A | 10/2000 | Say et al. |
| 5,706,807 A * | 1/1998 | Picha ......................... 600/345 | | 6,135,978 A | 10/2000 | Houben et al. |
| 5,711,861 A * | 1/1998 | Ward et al. ................ 600/347 | | 6,144,869 A | 11/2000 | Berner et al. |
| 5,713,888 A | 2/1998 | Neuenfeldt et al. | | 6,162,611 A | 12/2000 | Heller et al. |
| 5,733,336 A | 3/1998 | Neuenfeldt et al. | | 6,167,614 B1 | 1/2001 | Tuttle et al. |
| 5,741,330 A | 4/1998 | Brauker et al. | | 6,175,752 B1 | 1/2001 | Say et al. |
| 5,743,262 A | 4/1998 | Lepper, Jr. et al. | | 6,187,062 B1 | 2/2001 | Oweis et al. |
| 5,756,632 A | 5/1998 | Ward et al. | | 6,189,536 B1 | 2/2001 | Martinez et al. |
| 5,773,286 A | 6/1998 | Dionne et al. | | 6,200,772 B1 | 3/2001 | Vadgama et al. |
| 5,776,324 A | 7/1998 | Usala | | 6,201,980 B1 | 3/2001 | Darrow et al. |
| 5,777,060 A | 7/1998 | Van Antwerp | | 6,206,856 B1 | 3/2001 | Mahurkar |
| 5,779,665 A | 7/1998 | Mastrototaro et al. | | 6,208,894 B1 | 3/2001 | Schulman et al. |
| 5,782,912 A | 7/1998 | Brauker et al. | | 6,212,416 B1 | 4/2001 | Ward et al. |
| 5,783,054 A | 7/1998 | Raguse et al. | | 6,214,185 B1 | 4/2001 | Offenbacher et al. |
| 5,787,900 A | 8/1998 | Butler et al. | | 6,230,059 B1 | 5/2001 | Duffin |
| 5,791,344 A | 8/1998 | Schulman et al. | | 6,231,879 B1 | 5/2001 | Li et al. |
| 5,795,774 A | 8/1998 | Matsumoto et al. | | 6,233,471 B1 | 5/2001 | Berner et al. |
| 5,798,065 A | 8/1998 | Picha | | 6,241,863 B1 | 6/2001 | Monbouquette |
| 5,800,420 A | 9/1998 | Gross et al. | | 6,248,067 B1 | 6/2001 | Causey, III et al. |
| 5,800,529 A | 9/1998 | Brauker et al. | | 6,256,522 B1 | 7/2001 | Schultz |
| 5,804,048 A | 9/1998 | Wong et al. | | 6,259,937 B1 | 7/2001 | Schulman et al. |
| 5,807,375 A | 9/1998 | Gross et al. | | 6,274,285 B1 | 8/2001 | Gries et al. |
| 5,807,406 A | 9/1998 | Brauker et al. | | 6,275,717 B1 | 8/2001 | Gross et al. |
| 5,811,487 A | 9/1998 | Schulz, Jr. et al. | | 6,281,015 B1 | 8/2001 | Mooney et al. |
| 5,820,622 A | 10/1998 | Gross et al. | | 6,284,478 B1 | 9/2001 | Heller et al. |
| 5,824,651 A | 10/1998 | Nanci et al. | | 6,293,925 B1 | 9/2001 | Safabash et al. |
| 5,833,603 A | 11/1998 | Kovacs et al. | | 6,299,578 B1 | 10/2001 | Kurnik et al. |
| 5,837,728 A | 11/1998 | Purcell | | 6,300,002 B1 | 10/2001 | Webb et al. |
| 5,840,240 A | 11/1998 | Stenoien et al. | | 6,309,351 B1 | 10/2001 | Kurnik et al. |
| 5,851,197 A | 12/1998 | Marano et al. | | 6,309,384 B1 | 10/2001 | Harrington et al. |
| 5,851,229 A | 12/1998 | Lentz et al. | | 6,325,978 B1 | 12/2001 | Labuda et al. |
| 5,858,365 A | 1/1999 | Faller | | 6,325,979 B1 | 12/2001 | Hahn et al. |
| 5,858,747 A | 1/1999 | Schinstine et al. | | 6,329,161 B1 | 12/2001 | Heller et al. |
| 5,861,019 A | 1/1999 | Sun et al. | | 6,330,464 B1 | 12/2001 | Colvin, Jr. et al. |
| 5,871,514 A | 2/1999 | Wiklund et al. | | 6,343,225 B1 * | 1/2002 | Clark, Jr. ..................... 600/347 |
| 5,879,713 A | 3/1999 | Roth et al. | | 6,365,670 B1 | 4/2002 | Fry |
| 5,882,354 A | 3/1999 | Brauker et al. | | 6,368,274 B1 | 4/2002 | Van Antwerp et al. |
| 5,882,494 A | 3/1999 | Van Antwerp | | 6,372,244 B1 | 4/2002 | Antanavich et al. |
| 5,897,578 A | 4/1999 | Wiklund et al. | | 6,383,478 B1 | 5/2002 | Prokop et al. |
| 5,904,708 A | 5/1999 | Goedeke | | 6,400,974 B1 | 6/2002 | Lesho |
| 5,910,554 A | 6/1999 | Kempe et al. | | 6,409,674 B1 | 6/2002 | Brockway et al. |
| 5,913,998 A | 6/1999 | Butler et al. | | 6,413,393 B1 | 7/2002 | Van Antwerp et al. |
| 5,914,026 A | 6/1999 | Blubaugh, Jr. et al. | | 6,424,847 B1 | 7/2002 | Mastrototaro et al. |
| 5,917,346 A | 6/1999 | Gord | | 6,447,448 B1 | 9/2002 | Ishikawa et al. |
| 5,919,215 A | 7/1999 | Wiklund et al. | | 6,447,542 B1 | 9/2002 | Weadock |
| 5,931,814 A | 8/1999 | Alex et al. | | 6,454,710 B1 | 9/2002 | Ballerstadt et al. |

| | | |
|---|---|---|
| 6,459,917 B1 | 10/2002 | Gowda et al. |
| 6,461,496 B1 | 10/2002 | Feldman et al. |
| 6,466,810 B1 * | 10/2002 | Ward et al. .................. 600/345 |
| 6,471,689 B1 | 10/2002 | Joseph et al. |
| 6,475,750 B1 | 11/2002 | Han et al. |
| 6,477,392 B1 | 11/2002 | Honigs et al. |
| 6,477,395 B2 | 11/2002 | Schulman et al. |
| 6,481,440 B2 | 11/2002 | Gielen et al. |
| 6,497,729 B1 | 12/2002 | Moussy et al. |
| 6,498,043 B1 | 12/2002 | Schulman et al. |
| 6,514,718 B2 | 2/2003 | Heller et al. |
| 6,520,997 B1 | 2/2003 | Pekkarinen et al. |
| 6,527,729 B1 | 3/2003 | Turcott |
| 6,537,318 B1 | 3/2003 | Ita et al. |
| 6,541,107 B1 | 4/2003 | King et al. |
| 6,545,085 B2 | 4/2003 | Kilgour et al. |
| 6,546,268 B1 | 4/2003 | Ishikawa et al. |
| 6,547,839 B2 | 4/2003 | Zhang et al. |
| 6,551,496 B1 | 4/2003 | Moles et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,569,195 B2 | 5/2003 | Yang et al. |
| 6,569,521 B1 | 5/2003 | Sheridan et al. |
| 6,579,498 B1 | 6/2003 | Eglise |
| 6,585,763 B1 | 7/2003 | Keilman et al. |
| 6,607,509 B2 | 8/2003 | Bobroff et al. |
| 6,613,379 B2 | 9/2003 | Ward et al. |
| 6,615,078 B1 | 9/2003 | Burson et al. |
| 6,618,934 B1 | 9/2003 | Feldman et al. |
| 6,642,015 B2 | 11/2003 | Vachon et al. |
| 6,645,181 B1 | 11/2003 | Lavi et al. |
| 6,654,625 B1 | 11/2003 | Say et al. |
| 6,663,615 B1 | 12/2003 | Madou et al. |
| 6,666,821 B2 * | 12/2003 | Keimel .................. 600/365 |
| 6,683,535 B1 | 1/2004 | Utke |
| 6,694,191 B2 | 2/2004 | Starkweather et al. |
| 6,695,860 B1 | 2/2004 | Ward et al. |
| 6,699,218 B2 | 3/2004 | Flaherty et al. |
| 6,702,857 B2 | 3/2004 | Brauker et al. |
| 6,721,587 B2 | 4/2004 | Gough |
| 6,731,976 B2 | 5/2004 | Penn et al. |
| 6,740,075 B2 | 5/2004 | Lebel et al. |
| 6,741,877 B1 | 5/2004 | Shults et al. |
| 6,810,290 B2 | 10/2004 | Lebel et al. |
| 6,862,465 B2 | 3/2005 | Shults et al. |
| 6,931,327 B2 | 8/2005 | Goode et al. |
| 6,991,643 B2 * | 1/2006 | Saadat .................. 606/221 |
| 7,110,803 B2 | 9/2006 | Shults et al. |
| 7,136,689 B2 | 11/2006 | Shults et al. |
| 7,153,265 B2 | 12/2006 | Vachon |
| 2002/0019330 A1 | 2/2002 | Murray et al. |
| 2002/0022883 A1 | 2/2002 | Burg |
| 2002/0042090 A1 | 4/2002 | Heller et al. |
| 2002/0133224 A1 | 9/2002 | Bajgar et al. |
| 2002/0151796 A1 | 10/2002 | Koulik |
| 2002/0182241 A1 | 12/2002 | Borenstein et al. |
| 2002/0193885 A1 | 12/2002 | Legeay et al. |
| 2003/0006669 A1 | 1/2003 | Pei et al. |
| 2003/0031699 A1 | 2/2003 | Van Antwerp |
| 2003/0032874 A1 | 2/2003 | Rhodes et al. |
| 2003/0036794 A1 | 2/2003 | Ragheb et al. |
| 2003/0036803 A1 | 2/2003 | McGhan |
| 2003/0070548 A1 | 4/2003 | Clausen |
| 2003/0072741 A1 | 4/2003 | Berglund et al. |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0091433 A1 | 5/2003 | Tam et al. |
| 2003/0099682 A1 | 5/2003 | Moussy et al. |
| 2003/0125613 A1 | 7/2003 | Enegren et al. |
| 2003/0188427 A1 | 10/2003 | Say et al. |
| 2003/0199744 A1 | 10/2003 | Buse et al. |
| 2003/0217966 A1 | 11/2003 | Tapsak et al. |
| 2004/0010207 A1 | 1/2004 | Flaherty et al. |
| 2004/0015134 A1 | 1/2004 | Lavi et al. |
| 2004/0030285 A1 | 2/2004 | Lavi et al. |
| 2004/0030294 A1 | 2/2004 | Mahurkar |
| 2004/0039406 A1 | 2/2004 | Jessen |
| 2004/0068230 A1 | 4/2004 | Estes et al. |
| 2004/0106857 A1 | 6/2004 | Gough |
| 2004/0186362 A1 | 9/2004 | Brauker et al. |
| 2004/0186365 A1 | 9/2004 | Jin et al. |
| 2004/0199059 A1 | 10/2004 | Brauker et al. |
| 2004/0219664 A1 | 11/2004 | Heller et al. |
| 2005/0027180 A1 | 2/2005 | Goode et al. |
| 2005/0027181 A1 | 2/2005 | Goode et al. |
| 2005/0027463 A1 | 2/2005 | Goode et al. |
| 2005/0033132 A1 | 2/2005 | Shults et al. |
| 2005/0043598 A1 | 2/2005 | Goode et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0090607 A1 | 4/2005 | Tapsak et al. |
| 2005/0115832 A1 | 6/2005 | Simpson et al. |
| 2005/0192557 A1 | 9/2005 | Brauker et al. |
| 2005/0245795 A1 | 11/2005 | Goode et al. |
| 2005/0245799 A1 | 11/2005 | Brauker et al. |
| 2006/0015020 A1 | 1/2006 | Neale et al. |
| 2006/0015024 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2008/0228054 A1 | 9/2008 | Shults et al. |

FOREIGN PATENT DOCUMENTS

| | | |
|---|---|---|
| EP | 0 107 634 | 5/1984 |
| EP | 0 127 958 | 12/1984 |
| EP | 0 320 109 | 6/1989 |
| EP | 0 353 328 | 2/1990 |
| EP | 0 390 390 | 10/1990 |
| EP | 0 512 122 | 11/1992 |
| EP | 0 534 074 | 3/1993 |
| EP | 0 535 898 | 4/1993 |
| EP | 0 539 751 | 5/1993 |
| EP | 0 747 069 | 12/1996 |
| EP | 0 776 628 | 6/1997 |
| EP | 0 817 809 | 1/1998 |
| EP | 0 885 932 | 12/1998 |
| FR | 2656423 | 6/1991 |
| FR | 2760962 | 9/1998 |
| GB | 1 442 303 | 7/1976 |
| GB | 2149918 | 6/1985 |
| JP | 62083849 | 4/1997 |
| WO | WO 89/02720 | 4/1989 |
| WO | WO 90/00738 | 1/1990 |
| WO | WO 92/07525 | 5/1992 |
| WO | WO 92/13271 | 8/1992 |
| WO | WO 93/14693 | 8/1993 |
| WO | WO 93/19701 | 10/1993 |
| WO | WO 94/22367 | 10/1994 |
| WO | WO 95/07109 | 3/1995 |
| WO | WO 96/01611 | 1/1996 |
| WO | WO 96/03117 | 2/1996 |
| WO | WO 96/14026 | 5/1996 |
| WO | WO 96/25089 | 8/1996 |
| WO | WO 96/30431 | 10/1996 |
| WO | WO 96/32076 | 10/1996 |
| WO | WO 96/36296 | 11/1996 |
| WO | WO 97/01986 | 1/1997 |
| WO | WO 97/43633 | 11/1997 |
| WO | WO 98/24358 | 6/1998 |
| WO | WO 00/13003 | 3/2000 |

| | | |
|---|---|---|
| WO | WO 00/19887 | 4/2000 |
| WO | WO 00/32098 | 6/2000 |
| WO | WO 00/33065 | 6/2000 |
| WO | WO 00/59373 | 10/2000 |
| WO | WO 01/12158 | 2/2001 |
| WO | WO 01/20019 | 3/2001 |
| WO | WO 01/20334 | 3/2001 |
| WO | WO 01/43660 | 6/2001 |
| WO | WO 01/88524 | 11/2001 |
| WO | WO 02/053764 | 7/2002 |
| WO | WO 03/022125 | 3/2003 |
| WO | WO 03/101862 | 12/2003 |

OTHER PUBLICATIONS

Answers.com. "xenogenic." The American Heritage Stedman's Medical Dictionary. Houghton Mifflin Company, 2002. Answers. com Nov. 7, 2006 http://www.Answers.com/topic/xenogenic.

Armour et al. Dec. 1990. Application of Chronic Intravascular Blood Glucose Sensor in Dogs. Diabetes 39:1519-1526.

Atanasov et al. 1994. Biosensor for continuous glucose monitoring. Biotechnology and Bioengineering 43:262-266.

Atanasov et al. 1997. Implantation of a refillable glucose monitoring-telemetry device. Biosens Bioelectron 12:669-680.

Baker et al. 1993. Dynamic concentration challenges for biosensor characterization. Biosensors & Bioelectronics 8:433-441.

Bani Amer, M. M. 2002. An accurate amperometric glucose sensor based glucometer with eliminated cross-sensitivity. J Med Eng Technol 26(5):208-213.

Beach et al. 1999. Subminiature implantable potentiostat and modified commercial telemetry device for remote glucose monitoring. IEEE Transactions on Instrumentation and Measurement 48(6):1239-1245.

Bellucci et al. Jan. 1986. Electrochemical behaviour of graphite-epoxy composite materials (GECM) in aqueous salt solutions, Journal of Applied Electrochemistry, 16(1):15-22.

Bindra et al. 1989. Pulsed amperometric detection of glucose in biological fluids at a surface-modified gold electrode. Anal Chem 61:2566-2570.

Bindra et al. 1991. Design and in Vitro Studies of a Needle-Type Glucose Senso for Subcutaneous Monitoring. Anal. Chem 63:1692-96.

Bobbioni-Harsch et al. 1993. Lifespan of subcutaneous glucose sensors and their performances during dynamic glycaemia changes in rats, J. Biomed. Eng. 15:457-463.

Bode et al. 1999. Continuous glucose monitoring used to adjust diabetes therapy improves glycosylated hemoglobin: A pilot study. Diabetes Research and Clinical Practice 46:183-190.

Bode et al. 2000. Using the continuous glucose monitoring system to improve the management of type 1 diabetes. Diabetes Technology & Therapeutics, 2(Suppl 1):S43-48.

Bode, B. W. 2000. Clinical utility of the continuous glucose monitoring system. Diabetes Technol Ther, 2(Suppl 1):S35-41.

Bott, A. W. 1997. A Comparison of Cyclic Voltammetry and Cyclic Staircase Voltammetry Current Separations 16:1, 23-26.

Bowman, L.; Meindl, J. D. 1986. The packaging of implantable integrated sensors. IEEE Trans Biomed Eng BME33(2):248-255.

Brauker et al. 1995. Neovascularization of synthetic membranes directed by membrane Microarchitecture. J. Biomed Mater Res 29:1517-1524.

Brauker et al. 1998. Sustained expression of high levels of human factor IX from human cells implanted within an immunoisolation device into athymic rodents. Hum Gene Ther 9:879-888.

Brauker et al. 2001. Unraveling Mysteries at the Biointerface: Molecular Mediator of Inhibition of Blood vessel Formation in the Foreign Body Capsule Revealed. Surfacts Biomaterials 6. 1;5.

Brauker et al. Jun. 27, 1996. Local Inflammatory Response Around Diffusion Chambers Containing Xenografts Transplantation 61(12):1671-1677.

Brauker, J., Abstract: Neovascularization of Cell Transplantation Devices: Membrane Architecture-Driven an Implanted Tissue-Driven Vascularization. Baxter Healthcare Corp., winter 2001.

Bremer et al. 2001. Benchmark data from the literature for evaluation of new glucose sensing technologies. Diabetes Technology & Therapeutics 3(3):409-418.

Brooks et al. "Development of an on-line glucose sensor for fermentation monitoring," Biosensors, 3:45-56 (1987/88).

Brunner et al. 1998. Validation of home blood glucose meters with respect to clinical and analytical approaches. Diabetes Care 21(4):585-590.

Cai et al. 2004. A wireless, remote query glucose biosensor based on a pH-sensitive polymer. Anal Chem 76(4):4038-4043.

Cass et al. "Ferrocene-mediated enzyme electrodes for amperometric determination of glucose," Anal. Chem., 36:667-71 (1984).

Cox et al. 1985. Accuracy of perceiving blood glucose in IDDM. Diabetes Care 8(6):529-536.

D'Arrigo et al. 2003. Porous-Si based bioreactors for glucose monitoring and drugs production. Proc. of SPIE 4982:178-184.

Davies, et al. 1992. Polymer membranes in clinical sensor applications. I. An overview of membrane function, Biomaterials, 13(14):971-978.

Dixon et al. 2002. Characterization in vitro and in vivo of the oxygen dependence of an enzyme/polymer biosensor for monitoring brain glucose. Journal of Neuroscience Methods 119:135-142.

DuPont[1] Dimension AR® (Catalog), 1998.

El-Sa'ad et al. 1990. Moisture Absorption by Epoxy Resins: the Reverse Thermal Effect. Journal of Materials Science 25:3577-3582.

Ernst et al. 2002. Reliable glucose monitoring through the use of microsystem technology. Anal. Bioanal. Chem. 373:758-761.

Fare et al. 1998. Functional characterization of a conducting polymer-based immunoassay system. Biosensors & Bioelectronics 13(3-4):459-470.

Feldman et al. 2003. A continuous glucose sensor based on wired enzyme technology—results from a 3-day trial in patients with type 1 diabetes. Diabetes Technol Ther 5(5):769-779.

Fischer et al. 1989. Oxygen Tension at the Subcutaneous Implantation Site of Glucose Sensors. Biomed. Biochem 11/12:965-972.

Frost et al. 2002. Implantable chemical sensors for real-time clinical monitoring: Progress and challenges. Current Opinion in Chemical Biology 6:633-641.

Garg et al. 2004. Improved Glucose Excursions Using an Implantable Real-Time continuous Glucose Sensor in Adults with Type I Diabetes. Diabetes Care 27:734-738.

Geller et al. 1997. Use of an immunoisolation device for cell transplantation and tumor immunotherapy. Ann NY Acad Sci 831:438-451.

Gerritsen et al. 1999. Performance of subcutaneously implanted glucose sensors for continuous monitoring. The Netherlands Journal of Medicine 54:167-179.

Gerritsen et al. 2001. Influence of inflammatory cells and serum on the performance of implantable glucose sensors. J Biomed Mater Res 54:69-75.

Gerritsen, M. 2000. Problems associated with subcutaneously implanted glucose sensors. Diabetes Care 23(2):143-145.

Gilligan et al. 1994. Evaluation of a subcutaneous glucose sensor out to 3 months in a dog model. Diabetes Care 17(8):882-887.

Gilligan et al. 2004, Feasibility of continuous long-term glucose monitoring from a subcutaneous glucose sensor in humans. Diabetes Technol Ther 6:378-386.

Gough et al. 2000. Immobilized glucose oxidase in implantable glucose sensor technology. Diabetes Technology & Therapeutics 2(3):377-380.

Gross et al. 2000. Efficacy and reliability of the continuous glucose monitoring system. Diabetes Technology & Therapeutics, 2(Suppl 1):S19-26.

Gross et al. 2000. Performance evaluation of the MiniMed® continuous glucose monitoring system during patient home use. Diabetes Technology & Therapeutics 2(1):49-56.

Hall et al. 1998. Electrochemical oxidation of hydrogen peroxide at platinum electrodes. Part II: Effect of potential. Electrochimica Acta 43(14-15):2015-2024.

Hall et al. 1998. Electrochemical oxidation of hydrogen peroxide at platinum electrodes. Part I: An adsorption-controlled mechanism. Electrochimica Acta, 43(5-6):579-588.

Hall et al. 1999. Electrochemical oxidation of hydrogen peroxide at platinum electrodes. Part III: Effect of temperature. Electrochimica Acta, 44:2455-2462.

Hall et al. 1999. Electrochemical oxidation of hydrogen peroxide at platinum electrodes. Part IV: Phosphate buffer dependence. Electrochimica Acta, 44:4573-4582.

Hall et al. 2000. Electrochemical oxidation of hydrogen peroxide at platinum electrodes. Part V: Inhibition by chloride. Electrochimica Acta, 45:3573-3579.

Heller, "Electrical wiring of redox enzymes," Acc. Chem. Res., 23:128-134 (1990).

Heller, A. 1992. Electrical Connection of Enzyme Redox Centers to Electrodes. J. Phys. Chem. 96:3579-3587.

Heller, A. 1999. Implanted electrochemical glucose sensors for the management of diabetes. Annu Rev Biomed Eng 1:153-175.

Heller, A. 2003. Plugging metal connectors into enzymes. Nat Biotechnol 21:631-2.

Hicks, 1985. In Situ Monitoring, Clinical Chemistry, 31(12):1931-1935.

Hitchman, M. L. 1978. Measurement of Dissolved Oxygen. In Elving et al. (Eds.). Chemical Analysis, vol. 49, Chap. 3, pp. 34-49, 59-123. New York: John Wiley & Sons.

Hrapovic et al. 2003. Picoamperometric detection of glucose at ultrasmall platinum-based biosensors: preparation and characterization. Anal Chem 75:3308-3315.

Hu, et al. 1993. A needle-type enzyme-based lactate sensor for in vivo monitoring, Analytica Chimica Acta, 281:503-511.

Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode, pp. 1-116.

Hunter et al. 2000. Minimally Invasive Glucose Sensor and Insulin Delivery System. MIT Home Automation and Healthcare Consortium. Progress Report No. 25.

Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Complications, 12:295-301.

Jensen et al. 1997. Fast wave forms for pulsed electrochemical detection of glucose by incorporation of reductive desorption of oxidation products. Analytical Chemistry 69(9):1776-1781.

Jeutter, D. C. 1982. A transcutaneous implanted battery recharging and biotelemeter power switching system. IEEE Trans Biomed Eng 29:314-321.

Johnson et al. 1992. In vivo evaluation of an electroenzymatic glucose sensor implanted in subcutaneous tissue. Biosensors & Bioelectronics, 7:709-714.

Jovanovic, L. 2000. The role of continuous glucose monitoring in gestational diabetes mellitus. Diabetes Technology & Therapeutics, 2 Suppl 1, S67-71.

Kang et al. 2003. In vitro and short-term in vivo characteristics of a Kel-F thin film modified glucose sensor. Anal Sci 19:1481-1486.

Kargol et al. 2001. Studies on the structural properties of porous membranes: measurement of linear dimensions of solutes. Biophys Chem 91:263-271.

Kaufman. 2000. Role of the continuous glucose monitoring system in pediatric patients. Diabetes Technology & Therapeutics 2(1):S-49-S-52.

Kawagoe et al. 1991. Enzyme-modified organic conducting salt microelectrode, Anal. Chem. 63:2961-2965.

Kerner et al. "The function of a hydrogen peroxide-detecting electroenzymatic glucose electrode is markedly impaired in human sub-cutaneous tissue and plasma," Biosensors & Bioelectronics, 8:473-482 (1993).

Kiechle, F.L. 2001. The impact of continuous glucose monitoring on hospital point-of-care testing programs. Diabetes Technol Ther 3:647-649.

Koschinsky et al. 2001. Sensors for glucose monitoring: Technical and clinical aspects. Diabetes Metab. Res. Rev. 17:113-123.

Kraver et al. 2001. A mixed-signal sensor interface microinstrument. Sensors and Actuators A 91:266-277.

Kruger et al. 2000. Psychological motivation and patient education: A role for continuous glucose monitoring. Diabetes Technology & Therapeutics, 2(Suppl 1):S93-97.

Lee et al. 1999. Effects of pore size, void volume, and pore connectivity on tissue responses. Society for Biomaterials 25th Annual Meeting, 171.

Lerner et al. 1984. An implantable electrochemical glucose sensor. Ann. N. Y. Acad. Sci. 428:263-278.

Leypoldt et al. 1984. Model of a two-substrate enzyme electrode for glucose. Anal. Chem. 56:2896-2904.

Loffler et al. 1995. Separation and determination of traces of ammonia in air by means of chromatomembrane cells. Fresenius J Anal Chem 352:613-614.

Lyman D. 1960. Polyurethanes. I. The Solution Polymerization of Diisocyanates with Ethylene Glycol. J. Polymer Sci XLV:45:49.

Maidan et al. 1992. Elimination of Electrooxidizable Interferent-Produced Currents in Amperometric Biosensors, Analytical Chemistry, 64:2889-2896.

Makale et al. 2003. Tissue window chamber system for validation of implanted oxygen sensors. Am. J. Physiol. Heart Circ. Physiol. 284:H2288-2294.

Malin et al. 1999. Noninvasive Prediction of Glucose by Near-Infrared Diffuse Reflectance Spectroscopy. Clinical Chemistry 45:9, 1651-1658.

Maran et al. 2002. Continuous subcutaneous glucose monitoring in diabetic patients: A multicenter analysis. Diabetes Care 25(2):347-352.

Mar., W. F. 2002. Dealing with the delay. Diabetes Technol Ther 4(1):49-50.

Mastrototaro et al. "An electroenzymatic glucose sensor fabricated on a flexible substrate," Sensors and Actuators B, 5:139-44 (1991).

Mastrototaro et al. 2003. Reproducibility of the continuous glucose monitoring system matches previous reports and the intended use of the product. Diabetes Care 26:256; author reply p. 257.

Mastrototaro, J. J. 2000. The MiniMed continuous glucose monitoring system. Diabetes Technol Ther 2(Suppl 1):S13-8.

Matsumoto et al. 2001. A long-term lifetime amperometric glucose sensor with a perfluorocarbon polymer coating. Biosens Bioelectron 16:271-276.

McCartney et al. 2001. Near-infrared fluorescence lifetime assay for serum glucose based on allophycocyanin-labeled concanavalin A. Anal Biochem 292:216-221.

McGrath et al. 1995. The use of differential measurements with a glucose biosensor for interference compensation during glucose determinations by flow injection analysis. Biosens Bioelectron 10:937-943.

McKean, et al. Jul. 7, 1988. A Telemetry Instrumentation System for Chronically Implanted Glucose and Oxygen Sensors. Transactions on Biomedical Engineering 35:526-532.

Memoli et al. 2002. A comparison between different immobilised glucoseoxidase-based electrodes. J Pharm Biomed Anal 29:1045-1052.

Miller et al. 1989. In vitro stimulation of fibroblast activity by factors generated from human monocytes activated by biomedical polymers. Journal of J Biomed Mater Res 23:911-930.

Miller et al. 1989. Generation of IL1-like activity in response to biomedical polymer implants: a comparison of in vitro and in vivo models. J Biomed Mater Res 23:1007-1026.

Miller, A. 1988. Human monocyte/macrophage activation and interleukin 1 generation by biomedical polymers. J Biomed Mater Res 23:713-731.

Moatti-Sirat et al. 1992. Towards continuous glucose monitoring: in vivo evaluation of a miniaturized glucose sensor implanted for several days in rat subcutaneous tissue. Diabetologia 35:224-230.

Moussy et al. 2000. Biomaterials community examines biosensor biocompatibility Diabetes Technol Ther 2:473-477.

Mowery et al. 2000. Preparation and characterization of hydrophobic polymeric films that are thromboresistant via nitric oxide release. Biomaterials 21:9-21.

Murphy, et al. 1992. Polymer membranes in clinical sensor applications. II. The design and fabrication of permselective hydrogels for electrochemical devices, Biomaterials, 13(14):979-990.

Myler et al. 2002. Ultra-thin-polysiloxane-film-composite membranes for the optimisation of amperometric oxidase enzyme electrodes. Biosens Bioelectron 17:35-43.

Nam et al. 2000. A novel fabrication method of macroporous biodegradable polymer scaffolds using gas foaming salt as a porogen additive. J Biomed Mater Res 53:1-7.

Ohara et al. 1994. "Wired" enzyme electrodes for amperometric determination of glucose or lactate in the presence of interfering substances. Anal Chem 66:2451-2457.

Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.

Okuda et al. 1971. Mutarotase effect on micro determinations of D-glucose and its anomers with β-D-glucose oxidase. Anal Biochem 43:312-315.

Palmisano et al. 2000. Simultaneous monitoring of glucose and lactate by an interference and cross-talk free dual electrode amperometric biosensor based on electropolymerized thin films. Biosensors & Bioelectronics 15:531-539.

Panetti 2002. Differential effects of sphingosine 1-phosphate and lysophosphatidic acid on endothelial cells. Biochimica et Biophysica Acta 1582:190-196.

Patel et al. 2003. Amperometric glucose sensors based on ferrocene containing polymeric electron transfer systems—a preliminary report. Biosens Bioelectron 18:1073-6.

Phillips and Smith. 1988. Bromedical Applications of Polyurethanes: Implications of Failure Mechanisms. J. Biomat. Appl. 3:202-227.

Pichert et al. 2000. Issues for the coming age of continuous glucose monitoring Diabetes Educ 26(6):969-980.

Pickup et al. "Implantable glucose sensors: choosing the appropriate sensing strategy," Biosensors, 3:335-346 (1987/88).

Pickup et al. "In vivo molecular sensing in diabetes mellitus: an implantable glucose sensor with direct electron transfer," Diabetologia, 32:213-217 (1989).

Pineda et al. 1996. Bone regeneration with resorbable polymeric membranes. III. Effect of poly(L-lactide) membrane pore size on the bone healing process in large defects. J. Biomedical Materials Research 31:385-394.

Pishko et al. "Amperometric glucose microelectrodes prepared through immobilization of glucose oxidase in redox hydrogels," Anal. Chem., 63:2268-72 (1991).

Pitzer et al. 2001. Detection of hypoglycemia with the GlucoWatch biographer. Diabetes Care 24(5):881-885.

Poitout et al. 1993. A glucose monitoring system for on line estimation in man of blood glucose concentration using a miniaturized glucose sensor implanted in the subcutaneous tissue and a wearable control unit. Diabetologia 36:658-663.

Postlethwaite et al. 1996. Interdigitated array electrode as an alternative to the rotated ring-disk electrode for determination of the reaction products of dioxygen reduction. Analytical Chemistry 68:2951-2958.

Quinn et al. 1997. Biocompatible, glucose-permeable hydrogel for in situ coating of implantable biosensors. Biomaterials 18:1665-1670.

Ratner, B.D. 2002. Reducing capsular thickness and enhancing angiogenesis around implant drug release systems. J Control Release 78:211-218.

Reach et al. 1986. A Method for Evaluating in vivo the Functional Characteristics of Glucose Sensors. Biosensors 2:211-220.

Reach et al. 1992. Can continuous glucose monitoring be used for the treatment of diabetes? Analytical Chemistry 64(5):381-386.

Reach, Gerard. 2001. Letters to the Editor Re: Diabetes Technology & Therapeutics, 2000;2:49-56. Diabetes Technology & Therapeutics 3(1):129-130.

Rebrin et al. 1999. Subcutaneous glucose predicts plasma glucose independent of insulin: Implications for continuous monitoring. Am. J. Physiol. 277:E561-71.

Rhodes et al. 1994. Prediction of pocket-portable and implantable glucose enzyme electrode performance from combined species permeability and digital simulation analysis. Analytical Chemistry 66(9):1520-1529.

Sakakida et al. 1992. Development of Ferrocene-Mediated Needle-Type Glucose Sensor as a Measure of True Subcutaneous Tissue Glucose Concentrations. Artif. Organs Today 2(2):145-158.

Sansen et al. 1985. "Glucose sensor with telemetry system." In Ko, W. H. (Ed.). Implantable Sensors for Closed Loop Prosthetic Systems. Chap. 12, pp. 167-175, Mount Kisco, NY: Futura Publishing Co.

Sansen et al. 1990. A smart sensor for the voltammetric measurement of oxygen or glucose concentrations. Sensors and Actuators B 1:298-302.

Schmidt et al. 1993. Glucose concentration in subcutaneous extracellular space. Diabetes Care 16(5):695-700.

Schoemaker et al. 2003. The SCGM1 system: Subcutaneous continuous glucose monitoring based on microdialysis technique. Diabetes Technology & Therapeutics 5(4):599-608.

Schuler et al. 1999. Modified gas-permeable silicone rubber membranes for covalent immobilisation of enzymes and their use in biosensor development. Analyst 124:1181-1184.

Selam, J. L. 1997. Management of diabetes with glucose sensors and implantable insulin pumps. From the dream of the 60s to the realities of the 90s. ASAIO J, 43:137-142.

Service, R. F. 2002. Can sensors make a home in the body? Science 297:962-3.

Sharkawy et al. 1996. Engineering the tissue which encapsulates subcutaneous implants. I. Diffusion properties, J Biomed Mater Res, 37:401-412.

Shaw et al. "In vitro testing of a simply constructed, highly stable glucose sensor suitable for implantation in diabetic patients," Biosensors & Bioelectronics, 6:401-406 (1991).

Shichiri et al. 1982. Wearable artificial endocrine pancrease with needle-type glucose sensor. Lancet 2:1129-1131.

Shichiri et al. 1985. Needle-type Glucose Sensor for Wearable Artificial Endocrine Pancreas in Implantable Sensors 197-210.

Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.

Shichiri et al. 1989. Membrane Design for Extending the Long-Life of an Implantable Glucose Sensor. Diab. Nutr. Metab. 2:309-313.

Shults et al. 1994. A telemetry-instrumentation system for monitoring multiple subcutaneously implanted glucose sensors. IEEE Transactions on Biomedical Engineering 41(10):937-942.

Sieminski et al. 2000. Biomaterial-microvasculature interactions. Biomaterials 21:2233-2241.

Skyler, J. S. 2000. The economic burden of diabetes and the benefits of improved glycemic control: The potential role of a continuous glucose monitoring system. Diabetes Technology & Therapeutics 2 Suppl 1:S7-12.

Sriyudthsak et al. 1996. Enzyme-epoxy membrane based glucose analyzing system and medical applications. Biosens Bioelectron 11:735-742.

Steil et al. 2003. Determination of plasma glucose during rapid glucose excursions with a subcutaneous glucose sensor. Diabetes Technology & Therapeutics 5(1):27-31.

Sternberg et al. 1988. Study and Development of Multilayer Needle-type Enzyme-based Glucose Microsensors. Biosensors 4:27-40.

Stokes. 1988. Polyether Polyurethanes: Biostable or Not? J. Biomat. Appl. 3:228-259.

Tanenberg et al. 2000. Continuous glucose monitoring system: A new approach to the diagnosis of diabetic gastroparesis. Diabetes Technology & Therapeutics, 2 Suppl 1:S73-80.

Tang et al. 1993. Fibrin(ogen) mediates acute inflammatory responses to biomaterials. J Exp Med 178:2147-2156.

Tang et al. 1995. Inflammatory responses to biomaterials. Am J Clin Pathol 103:466-471.

Tang et al. 1996. Molecular determinants of acute inflammatory responses to biomaterials. J Clin Invest 97:1329-1334.

Tang et al. 1998. Mast cells mediate acute inflammatory responses to implanted biomaterials. Proc Natl Acad Sci U S A 95:8841-8846.

Thome-Duret et al. 1996. Use of a subcutaneous glucose sensor to detect decreases in glucose concentration prior to observation in blood, Anal. Chem. 68:3822-3826.

Thomé-Duret et al. 1998. Continuous glucose monitoring in the free-moving rat. Metabolism, 47:799-803.

Thompson et al., In Vivo Probes: Problems and Perspectives, Department of Chemistry, University of Toronto, Canada, pp. 255-261, 1986.

Tibell et al. 2001. Survival of macroencapsulated allogeneic parathyroid tissue one year after transplantation in nonimmunosuppressed humans. Cell Transplant 10:591-9.

Tierney et al. 2000. Effect of acetaminophen on the accuracy of glucose measurements obtained with the GlucoWatch biographer. Diabetes Technol Ther 2:199-207.

Tierney et al. 2000. The GlucoWatch® biographer: A frequent, automatic and noninvasive glucose monitor. Ann. Med. 32:632-641.

Trecroci, D. 2002. A Glimpse into the Future- Continuous Monitoring of Glucose with a Microfiber. Diabetes Interview 42-43.

Tse and Gough. 1987. Time-Dependent Inactivation of Immobilized Glucose Oxidase and Catalase. Biotechnol. Bioeng. 29:705-713.

Turner and Pickup, "Diabetes mellitus: biosensors for research and management," *Biosensors*, 1:85-115 (1985).

Updike et al. 1967. The enzyme electrode. Nature, 214:986-988.

Updike et al. 1982. Implanting the glucose enzyme electrode: Problems, progress, and alternative solutions. Diabetes Care, 5(3):207-212.

Updike et al. 1988. Laboratory Evaluation of New Reusable Blood Glucose Sensor. Diabetes Care, 11:801-807.

Updike et al. 1994. Enzymatic glucose sensor: Improved long-term performance in vitro and in vivo. ASAIO Journal, 40(2):157-163.

Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons, pp. 117-137.

Updike et al. 2000. A subcutaneous glucose sensor with improved longevity, dynamic range, and stability of calibration. Diabetes Care 23(2):208-214.

Velho et al. 1989. In vitro and in vivo stability of electrode potentials in needle-type glucose sensors. Influence of needle material. Diabetes 38:164-171.

Velho et al. 1989. Strategies for calibrating a subcutaneous glucose sensor. Biomed Biochim Acta 48(11/12):957-964.

von Woedtke et al. 1989. In situ calibration of implanted electrochemical glucose sensors. Biomed Biochim. Acta 48(11/12):943-952.

Wagner et al. 1998. Continuous amperometric monitoring of glucose in a brittle diabetic chimpanzee with a miniature subcutaneous electrode. Proc. Natl. Acad. Sci. A, 95:6379-6382.

Wang et al. 1994. Highly Selective Membrane-Free, Mediator-Free Glucose Biosensor. Anal. Chem. 66:3600-3603.

Wang et al. 1997. Improved ruggedness for membrane-based amperometric sensors using a pulsed amperometric method. Anal Chem 69:4482-4489.

Ward et al. 2000. Rise in background current over time in a subcutaneous glucose sensor in the rabbit: Relevance to calibration and accuracy. Biosensors & Bioelectronics, 15:53-61.

Ward et al. 2002. A new amperometric glucose microsensor: In vitro and short-term in vivo evaluation. Biosensors & Bioelectronics, 17:181-189.

Wientjes, K. J. C. 2000. Development of a glucose sensor for diabetic patients (Ph.D. Thesis).

Wilkins et al. 1995. Glucose monitoring: state of the art and future possibilities. Med Eng Phys 18:273-288.

Wilkins et al. 1995. Integrated implantable device for long-term glucose monitoring. Biosens. Bioelectron 10:485-494.

Wilson et al. 1992. Progress toward the development of an implantable sensor for glucose. Clin. Chem. 38(9):1613-1617.

Wilson et al. 2000. Enzyme-based biosensors for in vivo measurements. Chem. Rev., 100:2693-2704.

Wood, W. et al. Mar. 1990. Hermetic Sealing with Epoxy. Mechanical Engineering 1-3.

Woodward. 1982. How Fibroblasts and Giant Cells Encapsulate Implants: Considerations in Design of Glucose Sensor. Diabetes Care 5:278-281.

Wu et al. 1999. In situ electrochemical oxygen generation with an immunoisolation device. Annals New York Academy of Sciences, pp. 105-125.

Yang et al. 1998. Development of needle-type glucose sensor with high selectivity. Science and Actuators B 46:249-256.

Zhang et al. 1994. Elimination of the acetaminophen interference in an implantable glucose sensor. Analytical Chemistry 66(7):1183-1188.

English translation of Office Action in Japanese App. No. 10/538680.

European Search Report for App. No. 98908875.2 dated Apr. 29, 2004.

ISR & WO for PCT/US04/015846 filed May 18, 2004.

Office Communication for European App. No. 98908875.2 dated Jun. 1, 2005.

Office Action dated Apr. 9, 2003 in U.S. Appl. No. 09/916,386.
Office Action dated Feb. 4, 2009 in U.S. Appl. No. 10/768,889.
Office Action dated Dec. 7, 1998 in U.S. Appl. No. 08/811,473.
Office Action dated Aug. 14, 2001 in U.S. Appl. No. 09/489,588.
Office Action dated Aug. 15, 2001 in U.S. Appl. No. 09/447,227.
Office Action dated Jan. 17, 2002 in U.S. Appl. No. 09/447,227.
Office Action dated Feb. 27, 2002 in U.S. Appl. No. 09/489,588.
Office Action dated Jul. 15, 2002 in U.S. Appl. No. 09/447,227.
Office Action dated Jan. 16, 2003 in U.S. Appl. No. 09/447,227.
Office Action dated Jun. 12, 2003 in U.S. Appl. No. 09/489,588.
Office Action dated Jul. 9, 2003 in U.S. Appl. No. 09/447,227.
Office Action dated Nov. 28, 2003 in U.S. Appl. No. 09/447,227.
Office Action dated Sep. 22, 2005 in U.S. Appl. No. 09/447,227.
Office Action dated Apr. 4, 2006 in U.S. Appl. No. 09/447,227.
Office Action dated Aug. 1, 2006 in U.S. Appl. No. 09/447,227.
Office Action dated Mar. 9, 2007 in U.S. Appl. No. 09/447,227.
Office Action dated Jul. 17, 2007 in U.S. Appl. No. 09/447,227.
Office Action dated Jan. 23, 2008 in U.S. Appl. No. 09/447,227.
Office Action dated Jun. 12, 2008 in U.S. Appl. No. 09/447,227.
Office Action dated Dec. 11, 2008 in U.S. Appl. No. 09/447,227.
Office Action dated May 26, 2009 in U.S. Appl. No. 09/447,227.
Office Action dated Mar. 22, 2004 in U.S. Appl. No. 09/916,858.
Office Action dated Sep. 21, 2004 in U.S. Appl. No. 10/657,843.
Office Action dated Sep. 21, 2004 in U.S. Appl. No. 09/916,858.
Office Action dated May 4, 2005 in U.S. Appl. No. 11/039,269.
Office Action dated Nov. 2, 2005 in U.S. Appl. No. 11/039,269.
Office Action dated Feb. 24, 2006 in U.S. Appl. No. 11/039,269.
Office Action dated Aug. 14, 2006 in U.S. Appl. No. 11/039,269.
Office Action dated Sep. 29, 2008 in U.S. Appl. No. 12/037,830.
Office Action dated Sep. 29, 2008 in U.S. Appl. No. 12/037,812.
Office Action dated Feb. 26, 2009 in U.S. Appl. No. 12/037,830.
Office Action dated Apr. 1, 2009 in U.S. Appl. No. 12/037,812.
Office Action dated Jul. 24, 2009 in U.S. Appl. No. 12/037,812.
Office Action dated Sep. 22, 2004 in U.S. Appl. No. 10/646,333.
Office Action dated Jun. 6, 2005 in U.S. Appl. No. 10/646,333.
Office Action dated Feb. 24, 2006 in U.S. Appl. No. 10/646,333.
Office Action dated Oct. 16, 2006 in U.S. Appl. No. 10/647,065.
Office Action dated May 23, 2007 in U.S. Appl. No. 11/055,779.
Office Action dated Oct. 24, 2007 in U.S. Appl. No. 11/055,779.
Office Action dated Sep. 21, 2007 in U.S. Appl. No. 10/838,912.
Office Action dated Mar. 24, 2008 in U.S. Appl. No. 10/838,912.
Office Action dated Jul. 16, 2008 in U.S. Appl. No. 10/838,912.
Office Action mailed Jun. 5, 2008 in U.S. Appl. No. 10/838,909.
Office Action mailed Mar. 16, 2009 in U.S. Appl. No. 10/838,909.
Office Action dated Sep. 18, 2008 in U.S. Appl. No. 11/439,630.
Office Action dated Feb. 23, 2009 in U.S. Appl. No. 11/439,630.
Office Action dated Dec. 1, 2008 in U.S. Appl. No. 11/503,367.

* cited by examiner

ANALYTE MEASURING DEVICE

CROSS-REFERENCE TO RELATED APPLICATIONS

This application is a division of application Ser. No. 10/846,150, filed May 14, 2004, which is a continuation-in-part of application Ser. No. 10/647,065, filed Aug. 22, 2003 now U.S. Pat. No. 7,192,450, which claims the benefit of priority under 35 U.S.C. §119(e) to Provisional Application No. 60/472,673, filed May 21, 2003. This application claims the benefit of priority under 35 U.S.C. §119(e) to Provisional Application No. 60/544,722, filed Feb. 12, 2004. All above-referenced prior applications are incorporated by reference herein in their entirety.

FIELD OF THE INVENTION

The present invention relates generally to biointerface membranes that can be utilized with implantable devices, such as devices for the detection of analyte concentrations in a biological sample. The present invention further relates to methods for determining analyte levels using implantable devices including these membranes. More particularly, the invention relates to novel biointerface membranes, to devices and implantable devices including these membranes, and to methods for monitoring glucose levels in a biological fluid sample using an implantable analyte detection device.

BACKGROUND OF THE INVENTION

One of the most heavily investigated analyte sensing devices is the implantable glucose device for detecting glucose levels in patients with diabetes. Despite the increasing number of individuals diagnosed with diabetes and recent advances in the field of implantable glucose monitoring devices, currently used devices are unable to provide data safely and reliably for long periods of time (for example, months or years). See Moatti-Sirat et al., *Diabetologia*, 35:224-30 (1992). There are two commonly used types of implantable glucose sensing devices. These types include those that are implanted intravascularly and those that are implanted in tissue.

With reference to conventional devices that can be implanted in tissue, a disadvantage of these devices is that they tend to lose their function after the first few days to weeks following implantation. While not wishing to be bound by any particular theory, it is believed that this loss of function is due to the lack of direct contact with circulating blood to deliver sample to the tip of the probe of the implanted device. Because of these limitations, it has previously been difficult to obtain continuous and accurate glucose level measurements. However, such information is often extremely desirable to diabetic patients in ascertaining whether immediate corrective action is needed in order to adequately manage their disease.

Some medical devices, including implantable analyte measuring-devices, drug delivery devices, and cell transplantation devices require transport of solutes across the device-tissue interface for proper function. These devices generally include a membrane, herein referred to as a "cell-impermeable membrane" or "bioprotective membrane" which encases the device or a portion of the device to prevent access by host inflammatory or immune cells to sensitive regions of the device.

A disadvantage of cell-impermeable membranes is that they often stimulate a local inflammatory response, called the foreign body response (FBR) that has long been recognized as limiting the function of implanted devices that require solute transport. Previous efforts to overcome this problem have been aimed at increasing local vascularization at the device-tissue interface, but have achieved only limited success.

FIG. 1 is a schematic drawing that illustrates a classical FBR to a conventional cell-impermeable synthetic membrane 10 implanted under the skin. There are three main layers of a FBR. The innermost FBR layer 12, adjacent to the device, is composed generally of macrophages and foreign body giant cells 14 (herein referred to as the "barrier cell layer"). These cells form a monolayer of closely opposed cells over the entire surface of a microscopically smooth membrane, a macroscopically smooth (but microscopically rough) membrane, or a microporous (i.e., average pore size of less than about 1 µm) membrane. A membrane can be adhesive or non-adhesive to cells. However, its relatively smooth surface causes the downward tissue contracture 21 (discussed below) to translate directly to the cells at the device-tissue interface 26. The intermediate FBR layer 16 (herein referred to as the "fibrous zone"), lying distal to the first layer with respect to the device, is a wide zone (about 30 to 100 µm) composed primarily of fibroblasts 18, fibrous matrixes, and contractile fibrous tissue 20. The organization of the fibrous zone, and particularly the contractile fibrous tissue 20, contributes to the formation of the monolayer of closely opposed cells due to the contractile forces 21 around the surface of the foreign body (for example, membrane 10). The outermost FBR layer 22 is loose connective granular tissue containing new blood vessels 24 (herein referred to as the "vascular zone"). Over time, this FBR tissue becomes muscular in nature and contracts around the foreign body so that the foreign body remains tightly encapsulated. Accordingly, the downward forces 21 press against the tissue-device interface 26, and without any counteracting forces, aid in the formation of a barrier cell layer 14 that blocks and/or refracts the transport of analytes 23 (for example, glucose) across the tissue-device interface 26.

A consistent feature of the innermost layers 12, 16 is that they are devoid of blood vessels. This has led to widely supported speculation that poor transport of molecules across the device-tissue interface 26 is due to a lack of vascularization near the interface. See Scharp et al., World J. Surg., 8:221-229 (1984); and Colton et al., J. Biomech. Eng., 113: 152-170 (1991). Previous efforts to overcome this problem have been aimed at increasing local vascularization at the device-tissue interface, but have achieved only limited success.

Although local vascularization can aid in sustenance of local tissue over time, the presence of a barrier cell layer 14 prevents the passage of molecules that cannot diffuse through the layer. For example, when applied to an implantable glucose-measuring device, both glucose and its phosphorylated form do not readily transit the cell membrane. Consequently, little glucose reaches the implant's membrane through the barrier cell layer. The known art purports to increase the local vascularization in order to increase solute availability. See Brauker et al., U.S. Pat. No. 5,741,330. However, it has been observed by the inventors that once the monolayer of cells (barrier cell layer) is established adjacent to a membrane, increasing angiogenesis is not sufficient to increase transport of molecules such as glucose and oxygen across the device-tissue interface 26. In fact, the barrier cell layer blocks and/or refracts the analytes 23 from transport across the device-tissue interface 26.

The continuous measurement of substances in biological fluids is of interest in the control and study of metabolic disorders. Electrode systems have been developed for this purpose whereby an enzyme-catalyzed reaction is monitored (e.g., by the changing concentrations of reactants or products) by an electrochemical sensor. In such electrode systems, the electrochemical sensor comprises an electrode with potentiometric or amperometric function in close contact with a thin layer containing an enzyme in dissolved or insoluble form. Generally, a semipermeable membrane separates the thin layer of the electrode containing the enzyme from the sample of biological fluid that includes the substance to be measured.

Electrode systems that include enzymes have been used to convert amperometrically inactive substances into reaction products, which are amperometrically active. For example, in the analysis of blood for glucose content, glucose (which is relatively inactive amperometrically) can be catalytically converted by the enzyme glucose oxidase in the presence of oxygen and water to gluconic acid and hydrogen peroxide. Tracking the concentration of glucose is possible since for every glucose molecule converted a proportional change in either oxygen or hydrogen peroxide sensor current will occur [U.S. Pat. Nos. 4,757,022 and 4,994,167 to Shults et al., both of which are hereby incorporated by reference. Hydrogen peroxide is anodically active and produces a current that is proportional to the concentration of hydrogen peroxide, which is directly related to the concentration of glucose in the sample. See, e.g. Updike et al., Diabetes Care, 11:801-807 (1988).

Despite recent advances in the field of implantable glucose monitoring devices, presently used devices are unable to provide data safely and reliably for long periods of time (e.g. months or years). See, e.g. Moatti-Sirat et al., Diabetologia 35:224-30 (1992). For example, Armour et al., Diabetes 39:1519-26 (1990), describes a miniaturized sensor that is placed intravascularly, thereby allowing the tip of the sensor to be in continuous contact with the blood. Unfortunately, probes that are placed directly into the vasculature put the recipient at risk for thrombophlebosis, thromboembolism, and thrombophlebitis.

Currently available glucose monitoring devices that can be implanted in tissue (e.g. subcutaneously) are also associated with several shortcomings. For example, there is no dependable flow of blood to deliver sample to the tip of the probe of the implanted device. Similarly, in order to be effective, the probe consumes some oxygen and glucose, but not enough to perturb the available glucose which it is intended to measure; subcutaneously implanted probes often reside in a relatively stagnant environment in which oxygen or glucose depletion zones around the probe tip can result in erroneously low measured glucose levels. Finally, the probe can be subject to "motion artifact" because the device is not adequately secured to the tissue, thus contributing to unreliable results. Partly because of these limitations, it has previously been difficult to obtain accurate information regarding the changes in the amounts of analytes (e.g. whether blood glucose levels are increasing or decreasing); this information is often extremely desirable, for example, in ascertaining whether immediate corrective action is needed in the treatment of diabetic patients.

There is a need for a device that accurately and continuously determines the presence and the amounts of a particular analyte, such as glucose, in biological fluids. The device should be easy to use, be capable of accurate measurement of the analyte over long periods of time, and should not readily be susceptible to motion artifact.

SUMMARY OF THE INVENTION

It has been confirmed through histological examination of biointerface membranes that the one mechanism for inhibition of molecular transport across the device-tissue interface is the barrier cell layer adjacent to the membrane. There is a strong correlation between the desired device function and the lack of formation of a barrier cell layer at the device-tissue interface. For example, glucose-measuring devices that were observed histologically to have substantial barrier cell layers were functional only 41% of the time after 12 weeks in vivo. In contrast, devices that did not have significant barrier cell layers were functional 86% of the time after 12 weeks in vivo.

Consequently, there is a need for a membrane that interferes with the formation of a barrier cell layer and protects the sensitive regions of the implantable device from host inflammatory response. The biointerface membranes of the preferred embodiments interfere with the formation of a monolayer of cells adjacent to the membrane, henceforth referred to herein as a "barrier cell layer", which interferes with the transport of oxygen, glucose, or other analytes or substances, across a device-tissue interface.

The biointerface membranes, devices including these membranes, and methods of use of these membranes according to the preferred embodiments allow for long term protection of implanted cells or drugs, as well as for obtaining continuous information regarding, for example, glucose levels of a host over extended periods of time. Because of these abilities, the biointerface membranes of the preferred embodiments can be extremely useful in implantable devices for the management of transplant patients, diabetic patients, and patients requiring frequent drug treatment.

In a first embodiment, a device for subcutaneous monitoring of glucose levels is provided, comprising a housing and a sensor, the sensor comprising an angiogenic layer for promoting adequate microcirculatory delivery of glucose and oxygen to the sensor, wherein the angiogenic layer further comprises a bioactive agent.

In an aspect of the first embodiment, the device is sized and configured for wholly subcutaneous implantation.

In an aspect of the first embodiment, the angiogenic layer comprises a material selected from the group consisting of hydrophilic polyvinylidene fluoride, mixed cellulose esters, polyvinyl chloride, polyvinyl alcohol, polyethylene, polytetrafluoroethylene, cellulose acetate, cellulose nitrate, polycarbonate, nylon, polyester, mixed esters of cellulose polyvinylidene difluoride, silicone, polyacrylonitrile, polypropylene, polysulfone, polymethacrylate, and mixtures thereof.

In an aspect of the first embodiment, the angiogenic layer comprises expanded polytetrafluoroethylene.

In an aspect of the first embodiment, the angiogenic layer comprises silicone.

In an aspect of the first embodiment, the bioactive agent is selected from the group consisting of anti-inflammatory agents, anti-infective agents, anesthetics, inflammatory agents, growth factors, immunosuppressive agents, antiplatelet agents, anticoagulants, ACE inhibitors, cytotoxic agents, anti-barrier cell compounds, vascularization-inducing compounds, anti-sense molecules, and mixtures thereof.

In an aspect of the first embodiment, the bioactive agent is an anti-inflammatory agent selected from the group consisting of nonsteroidal anti-inflammatory drugs (NTHEs), aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, tolmetin, corticosteroids, cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, dexamethasone, and mixtures thereof.

In an aspect of the first embodiment, the bioactive agent is an anti-infective agent selected from the group consisting of anthelmintics, mebendazole, antibiotics, aminoclycosides, gentamicin, neomycin, tobramycin, antifungal antibiotics, amphotericin b, fluconazole, griseofulvin, itraconazole, ketoconazole, nystatin, micatin, tolnaftate, cephalosporins, cefaclor, cefazolin, cefotaxime, ceftazidime, ceftriaxone, cefuroxime, cephalexin, beta-lactam antibiotics, cefotetan, meropenem, chloramphenicol, macrolides, azithromycin, clarithromycin, erythromycin, penicillins penicillin G sodium salt, amoxicillin, ampicillin, dicloxacillin, nafcillin, piperacillin, ticarcillin, tetracyclines, doxycycline, minocycline, tetracycline, bacitracin, clindamycin, colistimethate sodium, polymyxin b sulfate, vancomycin; antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine, quinolones, ciprofloxacin, levofloxacin, sulfonamides, sulfadiazine, sulfisoxazole, sulfones, dapsone, furazolidone, metronidazole, pentamidine, sulfanilamidum crystallinum, gatifloxacin, sulfamethoxazole/trimethoprim, and mixtures thereof.

In an aspect of the first embodiment, the bioactive agent is an anesthetic selected from the group consisting of ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocalne, phenazopyridine, and mixtures thereof.

In an aspect of the first embodiment, the bioactive agent is selected from the group consisting of S1P, monobutyrin, Cyclosporin A, Anti-thrombospondin-2, Rapamycin, Dexamethasone, Super Oxide Dismutase (SOD) Mimetic Compounds, Lipopolysaccharide, angiogenic lipid product of adipocytes, Sphingosine-1-Phosphate, Thrombospondin-2 antisense, and mixtures thereof.

In an aspect of the first embodiment, the bioactive agent is incorporated within the angiogenic layer by absorption into the angiogenic layer.

In an aspect of the first embodiment, the bioactive agent is incorporated within the angiogenic layer during formation of the angiogenic layer.

In an aspect of the first embodiment, the bioactive agent is incorporated within the angiogenic layer using a microcapsule agent.

In an aspect of the first embodiment, the bioactive agent is incorporated within the angiogenic layer using a carrier agent.

In an aspect of the first embodiment, the bioactive agent is incorporated in the angiogenic layer using at least one substance selected from the group consisting of an ionic surfactant, a nonionic surfactant, a detergent, an emulsifier, a demulsifier, a stabilizer, an aqueous carrier, an oleaginous carrier, a solvent, a preservative, an antioxidant, a buffering agent, and mixtures thereof.

In an aspect of the first embodiment, the angiogenic layer comprises a plurality of pores and wherein the bioactive agent is contained within the pores of the angiogenic layer.

In an aspect of the first embodiment, the sensor further comprises a membrane impregnated with an oxidase.

In an aspect of the first embodiment, the oxidase impregnated membrane comprises a resistance layer, an enzyme layer, an interference layer, and an electrolyte layer.

In an aspect of the first embodiment, the oxidase impregnated membrane comprises a single homogeneous structure.

In an aspect of the first embodiment, the resistance layer restricts transport of glucose therethrough.

In an aspect of the first embodiment, the resistance layer comprises a polymer membrane with an oxygen-to-glucose permeability ratio of at least about 100:1.

In an aspect of the first embodiment, the interference layer comprises a hydrophobic membrane substantially permeable to hydrogen peroxide.

In an aspect of the first embodiment, the interference layer comprises a hydrophobic membrane substantially impermeable to at least one substance having a molecular weight substantially greater than hydrogen peroxide.

In an aspect of the first embodiment, the electrolyte layer comprises a semipermeable hydrophilic coating.

In an aspect of the first embodiment, the electrolyte layer comprises a curable copolymer of a urethane polymer and a hydrophilic film-forming polymer.

In an aspect of the first embodiment, the enzyme layer comprises glucose oxidase.

In an aspect of the first embodiment, the housing comprises an electronic circuit and at least two electrodes operatively connected to the electronic circuit, wherein the sensor is operably connected to the electrodes of the housing.

In an aspect of the first embodiment, the housing comprises a data transmitting apparatus operatively connected to the electronic circuit for transmitting data to a location external to the device.

In an aspect of the first embodiment, the data transmitting apparatus comprises radiotelemetry.

In an aspect of the first embodiment, the sensor is located at an apex of the housing.

In an aspect of the first embodiment, the sensor comprises a dome configuration on at least a portion thereof.

In a second embodiment, a device for subcutaneous monitoring of a glucose level is provided, comprising a housing and a sensor, the sensor comprising a first domain, a second domain, and a bioactive agent; wherein the first domain supports tissue ingrowth and is positioned more distal to the housing than the second domain; wherein the second domain is substantially impermeable to macrophages and is situated between the first domain and the housing, and wherein the bioactive agent is incorporated within at least one of the first domain, the second domain, and the sensor.

In an aspect of the second embodiment, the device is sized and configured for wholly subcutaneous implantation.

In an aspect of the second embodiment, the first domain comprises a material selected from the group consisting of hydrophilic polyvinylidene fluoride, mixed cellulose esters, polyvinyl chloride, polyethylene, polyvinyl alcohol, polytetrafluoroethylene, expanded polytetrafluoroethylene, cellulose acetate, cellulose nitrate, polycarbonate, nylon, polyester, mixed esters of cellulose polyvinylidene difluoride, silicone, polyacrylonitrile, polypropylene, polysulfone, polymethacrylate, and mixtures thereof.

In an aspect of the second embodiment, the bioactive agent is selected from the group consisting of anti-inflammatory agents, anti-infective agents, anesthetics, inflammatory agents, growth factors, immunosuppressive agents, antiplatelet agents, anticoagulants, ACE inhibitors, cytotoxic agents, anti-barrier cell compounds, vascularization-inducing compounds, anti-sense molecules, and mixtures thereof.

In an aspect of the second embodiment, the bioactive agent is an anti-inflammatory agent selected from the group consisting of nonsteroidal anti-inflammatory drugs (NTHEs), aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, tolmetin, corticosteroids, cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, dexamethasone, and mixtures thereof.

In an aspect of the second embodiment, the bioactive agent is an anti-infective agent selected from the group consisting of anthelmintics, mebendazole, antibiotics, aminoclycosides, gentamicin, neomycin, tobramycin, antifungal antibiotics, amphotericin b, fluconazole, griseofulvin, itraconazole, ketoconazole, nystatin, micatin, tolnaftate, cephalosporins, cefaclor, cefazolin, cefotaxime, ceftazidime, ceftriaxone, cefuroxime, cephalexin, beta-lactam antibiotics, cefotetan, meropenem, chloramphenicol, macrolides, azithromycin, clarithromycin, erythromycin, penicillins penicillin G sodium salt, amoxicillin, ampicillin, dicloxacillin, nafcillin, piperacillin, ticarcillin, tetracyclines, doxycycline, minocycline, tetracycline, bacitracin, clindamycin, colistimethate sodium, polymyxin b sulfate, vancomycin; antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine; quinolones, ciprofloxacin, levofloxacin, sulfonamides, sulfadiazine, sulfisoxazole, sulfones, dapsone, furazolidone, metronidazole, pentamidine, sulfanilamidum crystallinum, gatifloxacin, and sulfamethoxazole/trimethoprim.

In an aspect of the second embodiment, the bioactive agent is an anesthetic selected from the group consisting of ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocalne, phenazopyridine, and mixtures thereof.

In an aspect of the second embodiment, the bioactive agent is selected from the group consisting of S1P, monobutyrin, Cyclosporin A, Anti-thrombospondin-2, Rapamycin, Dexamethasone, Super Oxide Dismutase (SOD) Mimetic Compounds, Lipopolysaccharide, angiogenic lipid product of adipocytes, Sphingosine-1-Phosphate, Thrombospondin-2 antisense, and mixtures thereof.

In an aspect of the second embodiment, the bioactive agent is incorporated within the first domain by absorption.

In an aspect of the second embodiment, the bioactive agent is incorporated within the second domain by absorption.

In an aspect of the second embodiment, the bioactive agent is loaded into at least one of the first domain, the second domain, and the sensor using a microcapsule agent.

In an aspect of the second embodiment, the bioactive agent is loaded is loaded into at least one of the first domain, the second domain, and the sensor using a carrier agent.

In an aspect of the second embodiment, the bioactive agent is incorporated into the vascular promotion layer using at least one substance selected from the group consisting of an ionic surfactant, a nonionic surfactant, a detergent, an emulsifier, a demulsifier, a stabilizer, an aqueous carrier, an oleaginous carrier, a solvent, a preservative, an antioxidant, a buffering agent, and mixtures thereof.

In an aspect of the second embodiment, first domain comprises a plurality of pores and wherein the vascular promotion layer comprises the bioactive agent contained within the pores of the angiogenic layer.

In an aspect of the second embodiment, the sensor further comprises a membrane impregnated with an oxidase.

In an aspect of the second embodiment, the oxidase impregnated membrane comprises a resistance layer, an enzyme layer, an interference layer, and an electrolyte layer.

In an aspect of the second embodiment, the oxidase impregnated membrane comprises a single homogeneous structure.

In an aspect of the second embodiment, the resistance layer restricts transport of glucose therethrough.

In an aspect of the second embodiment, the resistance layer comprises a polymer membrane with an oxygen-to-glucose permeability ratio of at least about 100:1.

In an aspect of the second embodiment, the interference layer comprises a hydrophobic membrane substantially permeable to hydrogen peroxide.

In an aspect of the second embodiment, the interference layer comprises a hydrophobic membrane substantially impermeable to substances having a molecular weight substantially greater than hydrogen peroxide.

In an aspect of the second embodiment, the electrolyte layer comprises a semipermeable hydrophilic coating.

In an aspect of the second embodiment, the electrolyte layer comprises a curable copolymer of a urethane polymer and a hydrophilic film-forming polymer.

In an aspect of the second embodiment, the enzyme layer comprises glucose oxidase.

In an aspect of the second embodiment, the housing comprises an electronic circuit and at least two electrodes operatively connected to the electronic circuit, and wherein the sensor is operably connected to the electrodes of the housing.

In an aspect of the second embodiment, the housing comprises a data transmitting apparatus operatively connected to the electronic circuit for transmitting data to a location external to the device.

In an aspect of the second embodiment, the data transmitting apparatus comprises radiotelemetry.

In an aspect of the second embodiment, the sensor is located at an apex of the housing.

In an aspect of the second embodiment, the sensor comprises a dome configuration on at least a portion thereof.

In a third embodiment, a device for subcutaneous monitoring of glucose levels is provided, comprising a housing, a sensor, and an angiogenic layer for promoting adequate microcirculatory delivery of glucose and oxygen to the sensor, wherein the angiogenic layer is configured to promote vascularization in or around the angiogenic layer so as to maintain sufficient blood flow to the sensor for glucose measurement thereby.

In an aspect of the third embodiment, the device is sized and configured for wholly subcutaneous implantation.

In an aspect of the third embodiment, the angiogenic layer comprises a material selected from the group consisting of hydrophilic polyvinylidene fluoride, mixed cellulose esters, polyvinyl chloride, polyvinyl alcohol, polyethylene, polytetrafluoroethylene, cellulose acetate, cellulose nitrate, polycarbonate, nylon, polyester, mixed esters of cellulose polyvinylidene difluoride, silicone, polyacrylonitrile, polypropylene, polysulfone, polymethacrylate, and mixtures thereof.

In an aspect of the third embodiment, the angiogenic layer comprises expanded polytetrafluoroethylene.

In an aspect of the third embodiment, the angiogenic layer comprises silicone.

In an aspect of the third embodiment, the sensor further comprising a membrane impregnated with an oxidase.

In an aspect of the third embodiment, the oxidase impregnated membrane comprises a resistance layer, an enzyme layer, an interference layer, and an electrolyte layer.

In an aspect of the third embodiment, the oxidase impregnated membrane comprises a single homogeneous structure.

In an aspect of the third embodiment, the resistance layer restricts transport of glucose therethrough.

In an aspect of the third embodiment, the resistance layer comprises a polymer membrane with an oxygen-to-glucose permeability ratio of at least about 100:1.

In an aspect of the third embodiment, the interference layer comprises a hydrophobic membrane substantially permeable to hydrogen peroxide.

In an aspect of the third embodiment, the interference layer comprises a hydrophobic membrane substantially impermeable to at least one substance having a molecular weight substantially greater than hydrogen peroxide.

In an aspect of the third embodiment, the electrolyte layer comprises a semipermeable hydrophilic coating.

In an aspect of the third embodiment, the electrolyte layer comprises a curable copolymer of a urethane polymer and a hydrophilic film-forming polymer.

In an aspect of the third embodiment, the enzyme layer comprises glucose oxidase.

In an aspect of the third embodiment, the housing comprises an electronic circuit and at least two electrodes operatively connected to the electronic circuit, and wherein the sensor is operably connected to the electrodes of the housing.

In an aspect of the third embodiment, the housing comprises a data transmitting apparatus operatively connected to the electronic circuit for transmitting data to a location external to the device.

In an aspect of the third embodiment, the data transmitting apparatus comprises radiotelemetry.

In an aspect of the third embodiment, the sensor is located at an apex of the housing.

In an aspect of the third embodiment, the sensor comprises a dome configuration on at least a portion thereof.

The devices and methods of the preferred embodiments allow for the implantation of analyte-monitoring devices such as glucose monitoring devices that result in a dependable flow of blood to deliver sample to the implanted device at a concentration representative of that in the vasculature. Moreover, the devices of the preferred embodiments become secured within the tissue of the subject, thereby greatly reducing or eliminating the phenomenon of "motion artifact". In addition, the devices of the preferred embodiments utilize materials that eliminate or significantly delay environmental stress cracking at the sensor interface, resulting in the ability to obtain accurate, long-term data.

These effects result, in part, from the use of materials that enhance the formation of a foreign body capsule (FBC). Previously, FBC formation has been viewed as being adverse to sensor function, and researchers have attempted to minimize FBC formation (see, e.g. U.S. Pat. No. 5,380,536 to Hubbell et al.). However, the methods and devices of the preferred embodiments utilize specific materials and architecture that elicit a type of FBC that does not hamper the generation of reliable data for long periods. The devices of the preferred embodiments are capable of accurate operation in the approximately 37° C., low $O_2$, environment characteristic of living tissue for extended lengths of time (e.g. months to years).

The electrode-membrane region of the devices of the preferred embodiments comprises a unique architectural arrangement. In preferred embodiments, the electrode surfaces are in contact with (or operably connected with) a thin electrolyte phase, which in turn is covered by an enzyme membrane that contains an enzyme, e.g. glucose oxidase, and a polymer system. A bioprotective membrane covers this enzyme membrane system and serves, in part, to protect the sensor from external forces and factors that can result in environmental stress cracking. Finally, an angiogenic layer is placed over the bioprotective membrane and serves to promote vascularization in the sensor interface region. It is to be understood that other configurations (e.g. variations of that described above) are contemplated by the preferred embodiments and are within the scope thereof.

The preferred embodiments contemplate a biological fluid measuring device, comprising a) a housing comprising electronic circuit means and at least two electrodes operably connected to the electronic circuit means; and b) a sensor means operably connected to the electrodes of the housing, the sensor means comprising i) a bioprotective membrane, and ii) an angiogenic layer, the angiogenic layer positioned more distal to the housing than the bioprotective membrane. In particular embodiments, the bioprotective membrane is substantially impermeable to macrophages. In some embodiments, the bioprotective membrane comprises pores having diameters ranging from about 0.1 micron to about 1.0 micron. In certain embodiments, the bioprotective membrane comprises polytetrafluoroethylene, and in particular embodiments, the angiogenic layer also comprises polytetrafluoroethylene.

Particular embodiments of the biological fluid measuring device further comprise c) means for securing the device to biological tissue, the securing means associated with the housing. In some embodiments, the securing means comprises a polyester velour jacket. In preferred embodiments, the securing means covers the top surface (e.g. the top member or the top member sheath, as described further below) and a portion of the sensor interface; it should be noted that the securing means generally should not cover the entire sensor interface, as this would interfere with the ability of blood vessels to deliver sample to the biological fluid measuring device. In preferred embodiments, the securing means comprises poly(ethylene terephthalate).

In further embodiments, the sensor means of the biological fluid measuring device further comprises means for determining the amount of glucose in a biological sample. In some embodiments, the glucose determining means comprises a membrane containing glucose oxidase, the glucose oxidase-containing membrane positioned more proximal to the housing than the bioprotective membrane. In additional embodiments, the housing further comprises means for transmitting data to a location external to the device (e.g. a radiotelemetry device).

The preferred embodiments also contemplate a device for measuring glucose in a biological fluid, comprising a) a housing comprising electronic circuit means and at least one electrode operably connected to the electronic circuit means; and b) a sensor means operably connected to the electrode of the housing, the sensor means comprising i) means for determining the amount of glucose in a biological sample, the glucose determining means operably associated with the electrode, ii) a bioprotective membrane, the bioprotective membrane positioned more distal to the housing than the glucose determining means and substantially impermeable to macrophages, and iii) an angiogenic layer, the angiogenic layer positioned more distal to the housing than the bioprotective membrane.

In particular embodiments, the glucose determining means comprises a membrane containing glucose oxidase. In some embodiments, the angiogenic layer comprises polytetrafluoroethylene.

In some embodiments, the pores of the bioprotective membrane have diameters ranging from about 0.1 micron to about 1.0 micron, while in other embodiments the pores have diameters ranging from about 0.2 micron to about 0.5 micron. In certain embodiments, the bioprotective membrane comprises polytetrafluoroethylene.

Still other embodiments further comprise c) means for securing the device to biological tissue, the securing means associated with the housing. In particular embodiments, the securing means comprises poly(ethylene terephthalate). Additional embodiments comprise means for transmitting data to a location external to the device; in some embodiments, the data transmitting means comprises a radiotelemetric device.

The preferred embodiments also contemplate a method for monitoring glucose levels, comprising a) providing i) a host, and ii) a device comprising a housing and means for determining the amount of glucose in a biological fluid; and b) implanting the device in the host under conditions such that the device measures the glucose accurately for a period exceeding 90 days. In some embodiments, the device measures glucose accurately for a period exceeding 150 days, while in other embodiments, the device measures glucose accurately for a period exceeding 360 days.

The preferred embodiments also contemplate a method of measuring glucose in a biological fluid, comprising a) providing i) a host, and ii) a device comprising a housing and means for determining the amount of glucose in a biological fluid, the glucose determining means capable of accurate continuous glucose sensing; and b) implanting the device in the host under conditions such that the continuous glucose sensing begins between approximately day 2 and approximately day 25. In some embodiments, the continuous glucose sensing begins between approximately day 3 and approximately day 21. In particular embodiments, the implanting is subcutaneous.

The devices of the preferred embodiments allow continuous information regarding, for example, glucose levels. Such continuous information enables the determination of trends in glucose levels, which can be extremely desirable in the management of diabetic patients.

DETAILED DESCRIPTION OF THE PREFERRED EMBODIMENT

Figure 1:
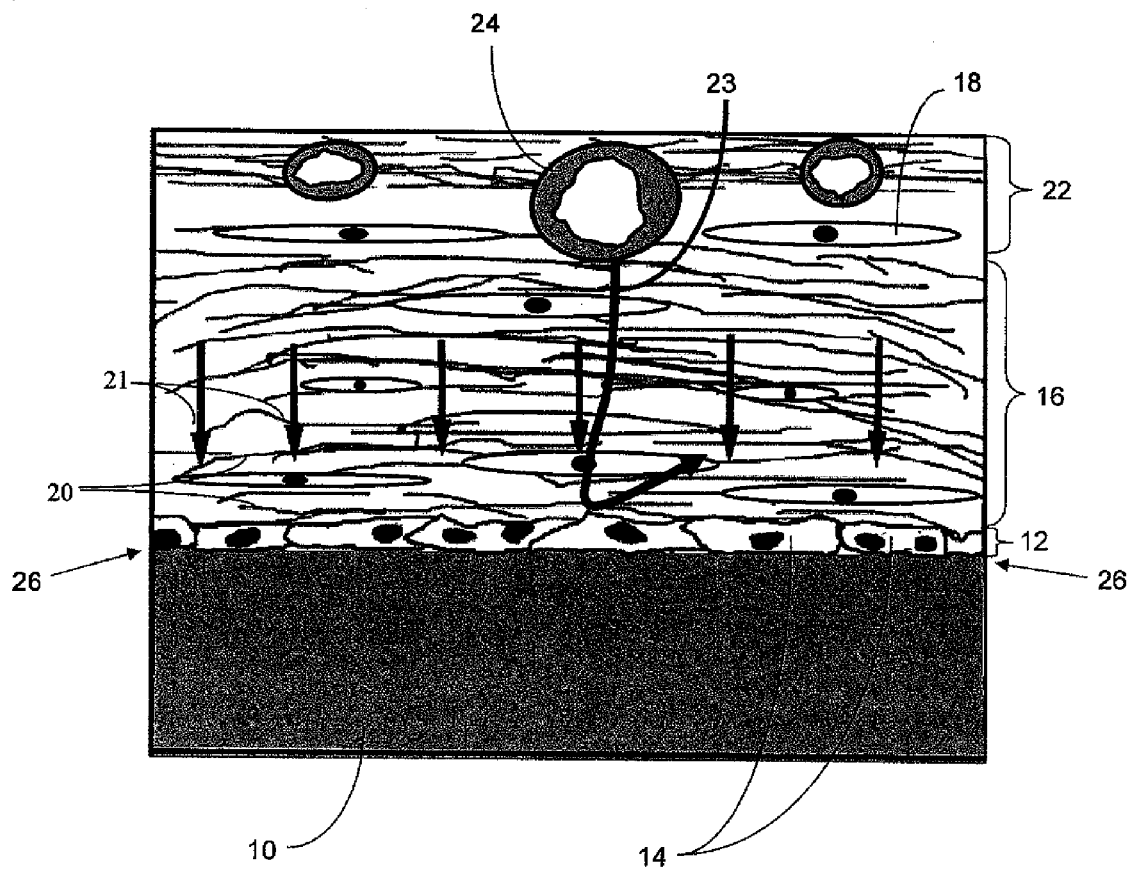
FIG. 1 is an illustration of classical three-layered foreign body response to a conventional synthetic membrane implanted under the skin.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

DEFINITIONS

In order to facilitate an understanding of the preferred embodiment, a number of terms are defined below.

The term "comprising" as used herein is synonymous with "including," "containing," or "characterized by," and is inclusive or open-ended and does not exclude additional, unrecited elements or method steps.

The term "biointerface membrane" as used herein is a broad term and is used in its ordinary sense, including, without limitation, to refer to a permeable membrane that functions as an interface between host tissue and an implantable device. In some embodiments, the biointerface membrane includes both macro-architectures and micro-architectures.

The term "barrier cell layer" as used herein is a broad term and is used in its ordinary sense, including, without limitation, to refer to a part of a foreign body response that forms a cohesive monolayer of cells (for example, macrophages and foreign body giant cells) that substantially block the transport of molecules and other substances to the implantable device.

The term "angiogenesis" as used herein is a broad term and is used in its ordinary sense, including, without limitation, the development of new blood vessels. Thus the term angiogenic can be used to describe a material, substance, or mechanism that stimulates new blood vessel growth.

The term "cell processes" as used herein is a broad term and is used in its ordinary sense, including, without limitation, to refer to pseudopodia of a cell.

The term "cellular attachment" as used herein is a broad term and is used in its ordinary sense, including, without limitation, to refer to adhesion of cells and/or cell processes to a material at the molecular level, and/or attachment of cells and/or cell processes to microporous material surfaces or macroporous material surfaces. One example of a material used in the prior art that encourages cellular attachment to its porous surfaces is the BIOPORE™ cell culture support marketed by Millipore (Bedford, Mass.), and as described in Brauker et al., U.S. Pat. No. 5,741,330.

The term "solid portions" as used herein is a broad term and is used in its ordinary sense, including, without limitation, to refer to portions of a membrane's material having a mechanical structure that demarcates cavities, voids, or other non-solid portions.

The term "co-continuous" as used herein is a broad term and is used in its ordinary sense, including, without limitation, to describe a solid portion or cavity wherein an unbroken curved line in three dimensions can be drawn between two sides of a membrane.

The term "biostable" as used herein is a broad term and is used in its ordinary sense, including, without limitation, to describe materials that are relatively resistant to degradation by processes that are encountered in vivo.

The terms "bioresorbable" or "bioabsorbable" as used here are broad terms and are used in their ordinary sense, including, without limitation, to describe materials that can be absorbed, or lose substance, in a biological system.

The terms "nonbioresorbable" or "nonbioabsorbable" as used here are broad terms and are used in their ordinary sense, including, without limitation, to describe materials that are not substantially absorbed, or do not substantially lose substance, in a biological system.

The terms "oxygen antenna domain" or "oxygen reservoir" as used here are broad terms and are used in their ordinary sense, including, without limitation, to refer to a domain composed of a material that has a higher oxygen solubility than an aqueous media such that it concentrates oxygen from the biological fluid surrounding a biocompatible membrane. In one embodiment, the properties of silicone (and/or silicone compositions) enable domains formed from silicone to act as an oxygen antenna domain. The oxygen antenna domain enhances function in a glucose-measuring device by applying a higher flux of oxygen to certain locations.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobinopathies, A,S,C,E, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Helicobacter pylori*, hepatitis B virus, herpes virus, HIV-1, IgE (atopic disease), influenza virus, *Leishmania donovani*, leptospira, measles/mumps/rubella, *Mycobacterium leprae*, *Mycoplasma pneumoniae*, *Myoglobin*, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni*, *Toxoplasma gondii*, *Trepenoma pallidium*, *Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The terms "analyte-measuring device," "means for determining the amount of glucose in a biological sample", and the like as used herein is a broad term and is used in its ordinary sense, including, without limitation, to refer to any mechanism (for example, an enzymatic mechanism or a non-enzymatic mechanism) by which an analyte can be quantified. An example is a glucose-measuring device incorporating a membrane that contains glucose oxidase that catalyzes the conversion of oxygen and glucose to hydrogen peroxide and gluconate:

$$\text{Glucose} + O_2 \rightarrow \text{Gluconate} + H_2O_2$$

In the above reaction, for each glucose molecule consumed, there is a proportional change in the co-reactant $O_2$ and the product $H_2O_2$. Current change in either the co-reactant or the product can be monitored to determine glucose concentration.

The term "host" as used herein is a broad term and is used in its ordinary sense, including, without limitation, to refer to mammals, preferably humans.

The phrase "continuous analyte sensing" as used herein is a broad term and is used in its ordinary sense, including, without limitation, to describe the period in which monitoring of analyte concentration is continuously, continually, and/or intermittently (but regularly) performed, for example, from about every 5 seconds or less to about 10 minutes or more, preferably from about 10, 15, 20, 25, 30, 35, 40, 45, 50, 55, or 60 second to about 1.25, 1.50, 1.75, 2.00, 2.25, 2.50, 2.75, 3.00, 3.25, 3.50, 3.75, 4.00, 4.25, 4.50, 4.75, 5.00, 5.25, 5.50, 5.75, 6.00, 6.25, 6.50, 6.75, 7.00, 7.25, 7.50, 7.75, 8.00, 8.25, 8.50, 8.75, 9.00, 9.25, 9.50 or 9.75 minutes.

The terms "sensor interface," "sensor means," "sensing region," and the like refer to the region of a monitoring device responsible for the detection of a particular analyte. For example, in some embodiments of a glucose monitoring device, the sensor interface refers to that region wherein a biological sample (e.g., blood or interstitial fluid) or a portion thereof contacts (directly or after passage through one or more membranes or layers) an enzyme (e.g., glucose oxidase); the reaction of the biological sample (or portion thereof) results in the formation of reaction products that allow a determination of the glucose level in the biological sample. In preferred embodiments, the sensor means comprises an angiogenic layer, a bioprotective layer, an enzyme layer, and an electrolyte phase (i.e., a free-flowing liquid phase comprising an electrolyte-containing fluid [described further below]). In some preferred embodiments, the sensor interface protrudes beyond the plane of the housing. As another example, the sensing region can comprise a non-conductive body, a working electrode (anode), a reference electrode, and a counter electrode (cathode) passing through and secured within the device body, forming an electrochemically reactive surface at one location on the body and an electronic connection at another location on the body, and a sensing membrane affixed to the body and covering the electrochemically reactive surface. The counter electrode preferably has a greater electrochemically reactive surface area than the working electrode. During general operation of the device, a biological sample, for example, blood or interstitial fluid, or a component thereof contacts, either directly or after passage through one or more membranes, an enzyme, for example, glucose oxidase. The reaction of the biological sample or component thereof results in the formation of reaction products that permit a determination of the analyte level, for example, glucose, in the biological sample. In some embodiments, the sensing membrane further comprises an enzyme domain, for example, an enzyme layer, and an electrolyte phase, for example, a free-flowing liquid phase comprising an electrolyte-containing fluid described further below.

The term "electrochemically reactive surface" as used herein is a broad term and is used in its ordinary sense, including, without limitation, to refer to the surface of an electrode where an electrochemical reaction takes place. In a working electrode, hydrogen peroxide produced by an enzyme-catalyzed reaction of an analyte being detected reacts can create a measurable electronic current. For example, in the detection of glucose, glucose oxidase produces $H_2O_2$ peroxide as a byproduct. the $H_2O_2$ reacts with the surface of the working electrode to produce two protons ($2H^+$), two electrons ($2e^-$) and one molecule of oxygen ($O_2$), which produces the electronic current being detected. In a counter electrode, a reducible species, for example, $O_2$ is reduced at the electrode surface so as to balance the current generated by the working electrode.

The term "sensing membrane" as used herein is a broad term and is used in its ordinary sense, including, without limitation, to refer to a permeable or semi-permeable membrane that can comprise one or more domains and that is constructed of materials having a thickness of a few microns or more, and that are permeable to reactants and/or co-reactants employed in determining the analyte of interest. As an example, a sensing membrane can comprise an immobilized glucose oxidase enzyme, which catalyzes an electrochemical reaction with glucose and oxygen to permit measurement of a concentration of glucose.

The term "proximal" as used herein, is a broad term and is used in its ordinary sense, including, without limitation, to describe a region near to a point of reference, such as an origin or a point of attachment.

The term "distal" as used herein, is a broad term and is used in its ordinary sense, including, without limitation, to describe a region spaced relatively far from a point of reference, such as an origin or a point of attachment.

The terms "operably connected" and "operably linked" as used herein are broad terms and are used in their ordinary sense, including, without limitation, to describe one or more components linked to another component(s) in a manner that facilitates transmission of signals between the components. For example, one or more electrodes can be used to detect an analyte in a sample and convert that information into a signal; the signal can then be transmitted to an electronic circuit. In this example, the electrode is "operably linked" to the electronic circuit.

The term "bioactive agent" as used herein is a broad term and is used in its ordinary sense, including, without limitation, to describe any substance that has an effect on or elicits a response from living tissue.

The term "bioerodible" or "biodegradable", as used herein, is a broad term and is used in its ordinary sense, including, without limitation, to describe materials that are enzymatically degraded or chemically degraded in vivo into simpler components.

The terms "operably connected," "operably linked," and the like refer to one or more components being linked to another component(s) in a manner that allows transmission of, e.g. signals between the components. For example, one or more electrodes can be used to detect the amount of analyte in a sample and convert that information into a signal; the signal can then be transmitted to electronic circuit means (i.e., the electrode is "operably linked" to the electronic circuit means), which can convert the signal into a numerical value in the form of known standard values.

The term "electronic circuit means" refers to the electronic circuitry components of a biological fluid measuring device required to process information obtained by a sensor means regarding a particular analyte in a biological fluid, thereby providing data regarding the amount of that analyte in the fluid. U.S. Pat. No. 4,757,022 to Shults et al., previously incorporated by reference, describes suitable electronic circuit means (see, e.g. FIG. 7); of course, the preferred embodiments are not limited to use with the electronic circuit means described therein. A variety of circuits are contemplated, including but not limited to those circuits described in U.S. Pat. Nos. 5,497,772 and 4,787,398, hereby incorporated by reference.

The terms "angiogenic layer," "angiogenic membrane," and the like refer to a region, membrane, or the like of a biological fluid measuring device that promotes and maintains the development of blood vessels microcirculation around the sensor region of the device.

The terms "bioprotective membrane," "bioprotective layer," and the like refer to a semipermeable membrane comprised of protective biomaterials of a few microns thickness or more which are permeable to oxygen and glucose and are placed over the tip of the sensor to keep the white blood cells (e.g. tissue macrophages) from gaining proximity to and then damaging the enzyme membrane. In some embodiments, the bioprotective membrane has pores (typically from approximately 0.1 to approximately 1.0 micron). In preferred embodiments, a bioprotective membrane comprises polytetrafluoroethylene and contains pores of approximately 0.4 microns in diameter. Pore size is defined as the pore size provided by the manufacturer or supplier. In preferred embodiments, the bioprotective membrane is one embodiment of the second domain of the biointerface membrane.

The term "domain" as used herein is a broad term and is used in its ordinary sense, including, without limitation, regions of the biointerface membrane that can be layers, uniform or non-uniform gradients (i.e., anisotropic) or provided as portions of the membrane.

The phrase "substantially impermeable to macrophages" means that few, if any, macrophages are able to cross a barrier (e.g., the bioprotective membrane). In preferred embodiments, fewer than 1% of the macrophages that come in contact with the bioprotective membrane are able to cross.

The phrase "means for securing said device to biological tissue" refers to materials suitable for attaching the devices of the preferred embodiments to, e.g. the fibrous tissue of a foreign body capsule. Suitable materials include, but are not limited to, poly(ethylene terephthalate). In preferred embodiments, the top of the housing is covered with the materials in the form of surgical grade fabrics; more preferred embodiments also contain material in the sensor interface region (see FIG. 1B).

The phrase "means for transmitting data to a location external to said device" refers broadly to any mechanism by which data collected by a biological fluid measuring device implanted within a subject can be transferred to a location external to the subject. In preferred embodiments, radiotelemetry is used to provide data regarding blood glucose levels, trends, and the like. The terms "radiotelemetry," "radiotelemetric device," and the like refer to the transmission by radio waves of the data recorded by the implanted device to an ex vivo recording station (e.g. a computer), where the data is recorded and, if desired, further processed (see, e.g. U.S. Pat. Nos. 5,321,414 and 4,823,808, hereby incorporated by reference; PCT Patent Publication WO 9422367).

Overview

Devices and probes that are implanted into subcutaneous tissue conventionally elicit a foreign body response (FBR), which forms a foreign body capsule (FBC), as part of the body's response to the introduction of a foreign material. Specifically, implantation of a device, for example, a glucose sensing device, can result in an acute inflammatory reaction resolving to chronic inflammation with concurrent building of fibrotic tissue, such as is described in detail above. Eventually, a mature FBC including primarily contractile fibrous tissue forms around the device. See Shanker and Greisler, Inflammation and Biomaterials in Greco R S, ed., "Implantation Biology: The Host Response and Biomedical Devices" pp 68-80, CRC Press (1994).

The FBC surrounding conventional implanted devices has been shown to hinder or block the transport of analytes across the device-tissue interface. Thus, continuous long-term analyte transport in vivo has been conventionally believed to be unreliable or impossible. For example, because the formation of a FBC isolates an implantable device in a capsule containing fluid that does not mimic the levels of analytes, such as glucose and oxygen, in the body's vasculature, long-term device function was not believed to be reliable. Additionally, the composition of a FBC can prevent stabilization of the implantable device, contributing to motion artifact that also renders results unreliable.

In contrast to conventional belief, it has been recognized that FBC formation is the dominant event surrounding long-term implantation of any device, and can be managed or manipulated to support rather than hinder or block analyte transport. It has been observed that during the early periods following implantation of an analyte-sensing device, for example a glucose-sensing device, glucose changes can be tracked in vivo although significant time delays are typically incurred. However, after a few days to two or more weeks of implantation, these devices typically lose their function. See, for example, U.S. Pat. No. 5,791,344 and Gross et al. and "Performance Evaluation of the MiniMed Continuous Monitoring System During Patient home Use," Diabetes Technology and Therapeutics, (2000) 2(1):49-56, which have reported a glucose oxidase device, approved for use in humans by the Food and Drug Administration, that functions well for several days following implantation but loses function quickly after 3 days. These results suggest that there is sufficient vascularization and, therefore, perfusion of oxygen and glucose to support the function of an implantable glucose-measuring device for the first few days following implantation. New blood vessel formation is clearly not needed for the function of a glucose oxidase mediated electrochemical device implanted in the subcutaneous tissue for at least several days after implantation.

After several days, however, it is believed that this lack of device function is most likely due to cells, such as polymorphonuclear cells and monocytes, that migrate to the wound site during the first few days after implantation, for example, from the wounding of the tissue during implant. These cells consume local glucose and oxygen. If there is an overabundance of such cells, they can deplete glucose and/or oxygen before it is able to reach the device enzyme layer, thereby reducing the sensitivity of the device or rendering it non-functional. Further inhibition of device function can be due to inflammatory cells, for example, macrophages, that associate, for example, align at the interface, with the implantable device and physically block the transport of glucose into the device, for example, by formation of a barrier cell layer.

Additionally, these inflammatory cells can biodegrade many artificial biomaterials (some of which were, until recently, considered non-biodegradable). When activated by a foreign body, tissue macrophages degranulate, releasing hypochlorite (bleach) and other oxidative species. Hypochlorite and other oxidative species are known to break down a variety of polymers.

In order to overcome the problems associated with conventional membranes, the preferred embodiments employ biointerface membrane architectures that promote vascularization within the membrane and that interfere with barrier cell layer formation. The biointerface membranes are robust and suitable for long-term implantation and long-term analyte transport in vivo. Additionally, the membranes can be used in a variety of implantable devices, for example, analyte measuring devices, particularly glucose-measuring devices, cell transplantation devices, drug delivery devices, and electrical signal delivery and measuring devices. For example, in some embodiments of a glucose-monitoring device, the device interface can include a sensing membrane that has different domains and/or layers that can cover and protect an underlying enzyme membrane and the electrodes of the glucose-measuring device.

Biointerface Membranes

The biointerface membranes of the preferred embodiments comprise two or more domains, and incorporate a bioactive agent. A first domain is provided that includes an architecture, including cavity size, configuration, and/or overall thickness, that encourages vascular tissue ingrowth, disrupts downward tissue contracture, and/or discourages barrier cell formation. A second domain is provided that is impermeable to cells and/or cell processes. A bioactive agent is provided that is incorporated into the first and/or second domain, wherein the bioactive agent includes mechanisms that induce local vascularization and/or resist barrier cell formation.

Figure 2A:
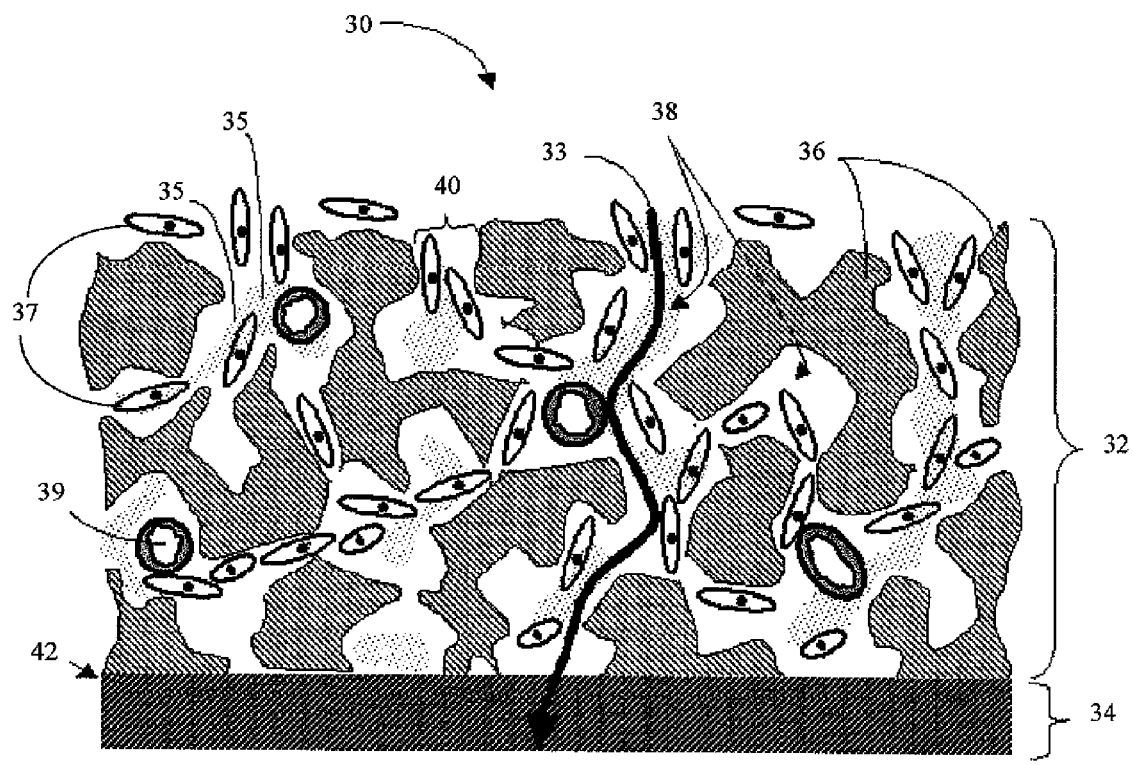
FIG. 2A is a cross-sectional schematic view of a membrane of a preferred embodiment that facilitates vascularization of the first domain without barrier cell layer formation.

FIG. 2A is a cross-sectional schematic view of a membrane 30 in vivo in one exemplary embodiment, wherein the membrane comprises a first domain 32 and second domain 34. The architecture of the membrane provides a robust, long-term implantable membrane that facilitates the transport of analytes through vascularized tissue ingrowth without the formation of a barrier cell layer.

The first domain 32 comprises a solid portion 36 and a plurality of interconnected three-dimensional cavities 38 formed therein. The cavities 38 have sufficient size and structure to allow invasive cells, such as fibroblasts 35, a fibrous matrix 37, and blood vessels 39 to enter into the apertures 40 that define the entryway into each cavity 38, and to pass through the interconnected cavities toward the interface 42 between the first and second domains. The cavities comprise an architecture that encourages the ingrowth of vascular tissue in vivo as indicated by the blood vessels 39 formed throughout the cavities. Because of the vascularization within the cavities, solutes 33 (for example, oxygen, glucose and other analytes) pass through the first domain with relative ease, and/or the diffusion distance (namely, distance that the glucose diffuses) is reduced.

The biointerface membranes of the preferred embodiments preferably include a bioactive agent, which is incorporated into at least one of the first and second domains 32, 34 of the biointerface membrane, or which is incorporated into the device and adapted to diffuse through the first and/or second domains, in order to modify the tissue response of the host to the membrane. The architectures of the first and second domains have been shown to support vascularized tissue ingrowth, to interfere with and resist barrier cell layer formation, and to facilitate the transport of analytes across the membrane. However, the bioactive agent can further enhance vascularized tissue ingrowth, resistance to barrier cell layer formation, and thereby facilitate the passage of analytes 33 across the device-tissue interface 42.

Architecture of the First Domain

The first domain of the biointerface membrane includes an architecture that supports tissue ingrowth, disrupts contractile forces typically found in a foreign body response, encourages vascularity within the membrane, and disrupts the formation of a barrier cell layer. The first domain, also referred to as the cell disruptive domain, comprises an open-celled configuration comprising interconnected cavities and solid portions. The distribution of the solid portion and cavities of the first domain preferably includes a substantially co-continuous solid domain and includes more than one cavity in three dimensions substantially throughout the entirety of the first domain. Generally, cells can enter into the cavities; however, they cannot travel through or wholly exist within the solid portions. The cavities permit most substances to pass through, including, for example, cells and molecules.

Figure 2B:
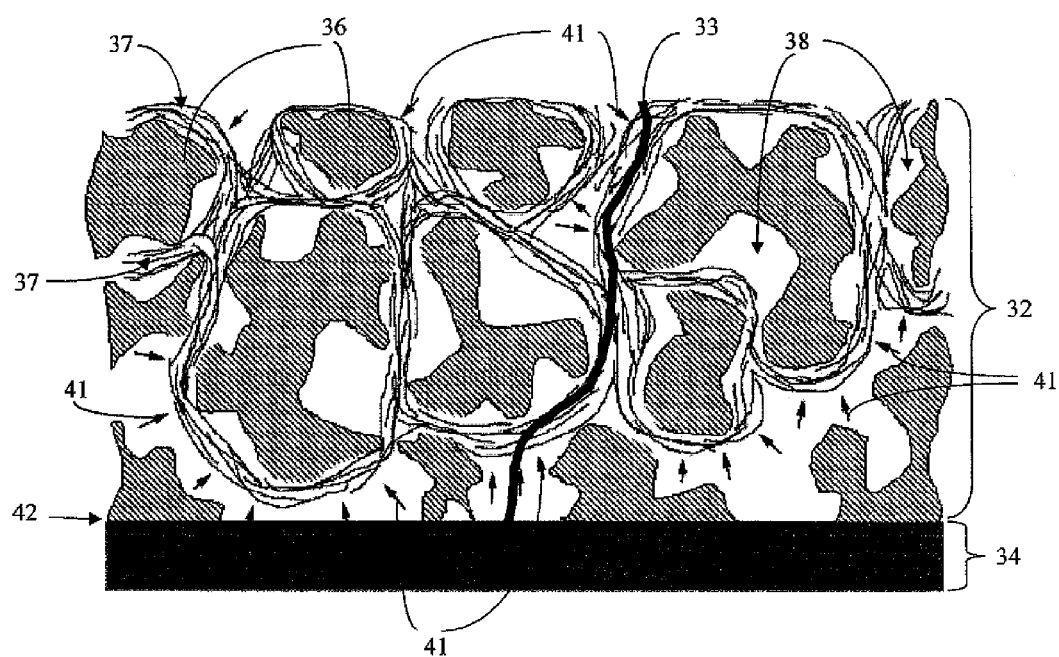
FIG. 2B is a cross-sectional schematic view of the membrane of FIG. 2A showing contractile forces caused by the fibrous tissue of the FBR.

Reference is now made to FIG. 2B, which is an illustration of the membrane of FIG. 2A, showing contractile forces caused by the fibrous tissue, for example, from the fibroblasts and fibrous matrix, of the FBR. Specifically, the architecture of the first domain, including the cavity interconnectivity and multiple-cavity depth, (namely, two or more cavities in three dimensions throughout a substantial portion of the first domain) can affect the tissue contracture that typically occurs around a foreign body.

A contraction of the FBC around the device as a whole produces downward forces on the device can be helpful in reducing motion artifacts, such as are described in copending U.S. patent application Ser. No. 10/646,333, filed Aug. 22, 2003 and entitled "OPTIMIZED DEVICE GEOMETRY FOR AN IMPLANTABLE GLUCOSE DEVICE," which is incorporated herein in its entirety by reference. The architecture of the first domain of the biointerface membrane, including the interconnected cavities and solid portion, is advantageous because the contractile forces caused by the downward tissue contracture that can otherwise cause cells to flatten against the device and occlude the transport of analytes, is instead translated to, disrupted by, and/or counteracted by the forces 41 that contract around the solid portions 36 (for example, throughout the interconnected cavities 38) away from the device. That is, the architecture of the solid portions 36 and cavities 38 of the first domain cause contractile forces

41 to disperse away from the interface between the first domain 32 and second domain 34. Without the organized contracture of fibrous tissue toward the tissue-device interface 42 typically found in a FBC (FIG. 1), macrophages and foreign body giant cells do not form a substantial monolayer of cohesive cells (namely, a barrier cell layer) and therefore the transport of molecules across the second domain and/or membrane is not blocked, as indicated by free transport of analyte 33 through the first and second domains in FIGS. 2A and 2B.

Various methods are suitable for use in manufacturing the first domain in order to create an architecture with preferred dimensions and overall structure. The first domain can be manufactured by forming particles, for example, sugar granules, salt granules, and other natural or synthetic uniform or non-uniform particles, in a mold, wherein the particles have shapes and sizes substantially corresponding to the desired cavity dimensions. In some methods, the particles are made to coalesce to provide the desired interconnectivity between the cavities. The desired material for the solid portion can be introduced into the mold using methods common in the art of polymer processing, for example, injecting, pressing, vacuuming, or pouring. After the solid portion material is cured or solidified, the coalesced particles are then dissolved, melted, etched, or otherwise removed, leaving interconnecting cavities within the solid portion. In such embodiments, sieving can be used to determine the dimensions of the particles, which substantially correspond to the dimensions of resulting cavities. In sieving, also referred to as screening, the particles are added to the sieve and then shaken to produce overs and unders. The overs are the particles that remain on the screen and the unders are the particles that pass through the screen. Other methods and apparatus known in the art are also suitable for use in determining particle size, for example, air classifiers, which apply opposing air flows and centrifugal forces to separate particles having sizes down to 2 μm, can be used to determine particle size when particles are smaller than 100 μm.

In one embodiment, the cavity size of the cavities 38 of the first domain is substantially defined by the particle size(s) used in creating the cavities. In some embodiments, the particles used to form the cavities can be substantially spherical, thus the dimensions below describe a diameter of the particle and/or a diameter of the cavity. In some alternative embodiments, the particles used to form the cavities can be non-spherical (for example, rectangular, square, diamond, or other geometric or non-geometric shapes), thus the dimensions below describe one dimension (for example, shortest, average, or longest) of the particle and/or cavity.

In some embodiments, a variety of different particle sizes can be used in the manufacture of the first domain. In some embodiments, the dimensions of the particles can be somewhat smaller or larger than the dimensions of the resulting cavities, due to dissolution or other precipitation that can occur during the manufacturing process.

Although one method of manufacturing porous domains is described above, a variety of methods known to one of ordinary skill in the art can be employed to create the structures of preferred embodiments. For example, molds can be used in the place of the particles described above, such as coral, self-assembly beads, etched or broken silicon pieces, glass frit pieces, and the like. The dimensions of the mold can define the cavity sizes, which can be determined by measuring the cavities of a model final product, and/or by other measuring techniques known in the art, for example, by a bubble point test. In U.S. Pat. No. 3,929,971, Roy discloses a method of making a synthetic membrane having a porous microstructure by converting calcium carbonate coral materials to hydroxyapatite while at the same time retaining the unique microstructure of the coral material.

Other methods of forming a three-dimensional first domain can be used, for example holographic lithography, stereolithography, and the like, wherein cavity sizes are defined and precisely formed by the lithographic or other such process to form a lattice of unit cells, as described in co-pending U.S. Provisional Patent Application 60/544,722, entitled "Macro-Micro Architecture for Biointerface Membrane," which is incorporated herein by reference in its entirety and as described by Pekkarinen et al. in U.S. Pat. No. 6,520,997, which discloses a photolithographic process for creating a porous membrane.

The first domain 32 can be defined using alternative methods. In an alternative preferred embodiment, fibrous non-woven or woven materials, or other such materials, such as electrospun, scattered, or aggregate materials, are manufactured by forming the solid portions without particularly defining the cavities therebetween. Accordingly, in these alternative embodiments, structural elements that provide the three-dimensional conformation can include fibers, strands, globules, cones, and/or rods of amorphous or uniform geometry that are smooth or rough. These elements are hereinafter referred to as "strands." The solid portion of the first domain can include a plurality of strands, which generally define apertures formed by a frame of the interconnected strands. The apertures of the material form a framework of interconnected cavities. Formed in this manner, the first domain is defined by a cavity size of about 0.6 to about 1000 μm in at least one dimension.

Referring to the dimensions and architecture of the first domain 32, the porous biointerface materials can be loosely categorized into at least two groups: those having a micro-architecture and those having a macro-architecture.

FIGS. 2A and 2B illustrate one preferred embodiment wherein the biointerface material includes a macro-architecture as defined herein. In general, the cavity size of a macro-architecture provides a configuration and overall thickness that encourages vascular tissue ingrowth and disrupts tissue contracture that is believed to cause barrier cell formation in vivo (as indicated by the blood vessels 39 formed throughout the cavities), while providing a long-term, robust structure. Referring to the macro-architecture, a substantial number of the cavities 38, defined using any of the methods described above, are greater than or equal to about 20 μm in one dimension. In some other embodiments, a substantial number of the cavities are greater than or equal to about 30, 40, 50, 60, 70, 80, 90, 100, 120, 140, 160, 180, 200, 240, 280, 320, 360, 400, 500, 600, 700 μm, and preferably less than about 1000 μm in one dimension. Although the macro-architecture is associated the numerous advantages as described above, in some embodiments it can create an opportunity for foreign body giant cells to flatten against the second domain and/or implantable device 34 and potentially create a layer of barrier cells that can block some or all analyte transport. It is therefore advantageous to incorporate a bioactive agent into the macro-architecture in order to modify the tissue response of the host to the membrane.

The biointerface material can also be formed with a micro-architecture as defined herein. Generally, at least some of the cavities of a micro-architecture have a sufficient size and structure to allow inflammatory cells to partially or completely enter into the cavities. However, in contrast to the macro-architecture, the micro-architecture does not allow extensive ingrowth of vascular and connective tissues within the cavities. Therefore, in some embodiments, the microarchitecture of preferred embodiments is defined by the actual size of the cavity, wherein the cavities are formed from a mold, for example, such as described in more detail above. However, in the context of the micro-architecture it is preferable that the majority of the mold dimensions, whether particles, beads, crystals, coral, self-assembly beads, etched or broken silicon pieces, glass frit pieces, or other mold elements that form cavities, are less than about 20 μm in at least one dimension.

In some alternative micro-architecture embodiments, wherein the biointerface material is formed from a substantially fibrous material, the micro-architecture is defined by a strand size of less than 6 μm in all but the longest dimension, and a sufficient number of cavities are provided of a size and structure to allow inflammatory cells, for example, macrophages, to completely enter through the apertures that define the cavities, without extensive ingrowth of vascular and connective tissues.

In certain embodiments, the micro-architecture is characterized, or defined, by standard pore size tests, such as the bubble point test. The micro-architecture is selected with a nominal pore size of from about 0.6 μm to about 20 μm. In some embodiments, the nominal pore size from about 1, 2, 3, 4, 5, 6, 7, 8, or 9 μm to about 10, 11, 12, 13, 14, 15, 16, 17, 18, or 19 μm. It has been found that a porous polymer membrane having an average nominal pore size of about 0.6 to about 20 μm functions satisfactorily in creating a vascular bed within the micro-architecture at the device-tissue interface. The term "nominal pore size" in the context of the micro-architecture 52 in certain embodiments is derived from methods of analysis common to membrane, such as the ability of the membrane to filter particles of a particular size, or the resistance of the membrane to the flow of fluids. Because of the amorphous, random, and irregular nature of most of these commercially available membranes, the "nominal pore size" designation may not actually indicate the size or shape of the apertures and cavities, which in reality have a high degree of variability. Accordingly, as used herein with reference to the micro-architecture, the term "nominal pore size" is a manufacturer's convention used to identify a particular membrane of a particular commercial source which has a certain bubble point; as used herein, the term "pore" does not describe the size of the cavities of the material in the preferred embodiments. The bubble point measurement is described in Pharmaceutical Technology, May 1983, pp. 36 to 42.

While not wishing to be bound by any particular theory, it is believed that biointerface membranes with a micro-architecture as defined herein, are advantageous for inducing close vascular structures, maintaining rounded inflammatory cell morphology, preventing barrier cell layer formation, and preventing organized fibroblasts and connective tissue from entering into the membrane. In some instances, crushing and delamination of a micro-architecture biointerface material can occur, which allows foreign body giant cells to flatten against the implantable device and potentially create a barrier layer of cells that block some or all analyte transport. It can therefore be advantageous to incorporate a bioactive agent into the micro-architecture in order to modify the tissue response of the host to the membrane.

The optimum dimensions, architecture (for example, micro-architecture or macro-architecture), and overall structural integrity of the membrane can be adjusted according to the parameters of the device that it supports. For example, if the membrane is employed with a glucose-measuring device, the mechanical requirements of the membrane can be greater for devices having greater overall weight and surface area when compared to those that are relatively smaller.

With regard to the depth of cavities, improved vascular tissue ingrowth is observed when the first domain has a thickness that accommodates a depth of at least two cavities throughout a substantial portion of the thickness. Improved vascularization results at least in part from multi-layered interconnectivity of the cavities, such as in the preferred embodiments, as compared to a surface topography such as seen in the prior art, for example, wherein the first domain has a depth of only one cavity throughout a substantial portion thereof. The multi-layered interconnectivity of the cavities enables vascularized tissue to grow into various layers of cavities in a manner that provides mechanical anchoring of the device with the surrounding tissue. Such anchoring resists movement that can occur in vivo which results in reduced sheer stress and scar tissue formation. The optimum depth or number of cavities can vary depending upon the parameters of the device that it supports. For example, if the membrane is employed with a glucose-measuring device, the anchoring that is required of the membrane is greater for devices having greater overall weight and surface area as compared to those that are relatively smaller.

The thickness of the first domain can be optimized for decreased time-to-vascularize in vivo that is, vascular tissue ingrowth can occur somewhat faster with a membrane that has a thin first domain as compared to a membrane that has a relatively thicker first domain. Decreased time-to-vascularize results in faster stabilization and functionality of the biointerface in vivo. For example, in a subcutaneous implantable glucose device, consistent and increasing functionality of the device is at least in part a function of consistent and stable glucose transport across the biointerface membrane, which is at least in part a function of the vascularization thereof. Thus, quicker start-up time and/or shortened time lag (as when, for example, the diffusion path of the glucose through the membrane is reduced) can be achieved by decreasing the thickness of the first domain.

The thickness of the first domain is typically from about 20 μm to about 2000 μm, preferably from about 30, 40, 50, 60, 70, 80, 90, or 100 μm to about 800, 900, 1000, 1100, 1200, 1300, 1400, 1500, 1600, 1700, 1800, or 1900 μm, and most preferably from about 150, 200, 250, 300, 350, or 400 μm to about 450, 500, 550, 600, 650, 700, or 750 μm. However, in some alternative embodiments a thinner or thicker cell disruptive domain (first domain) can be desired.

The solid portion preferably includes one or more materials such as silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, polysulfones and block copolymers thereof including, for example, di-block, tri-block, alternating, random and graft copolymers. In some embodiments, the material selected for the first domain is an elastomeric material, for example, silicone, which is able to absorb stresses that can occur in vivo, such that sheer and other environmental forces are significantly minimized at the second domain. The solid portion can comprises a silicone composition with a hydrophile such as Polyethylene Glycol (PEG) covalently incorporated or grafted therein, such as described in co-pending U.S. patent application Ser. No. 10/695,636, filed Oct. 28, 2003, and entitled, "SILICONE COMPOSITION FOR BIOCOMPATIBLE MEMBRANE," which is incorporated herein by reference in its entirety. Additionally, elastomeric materials with a memory of the original configuration can withstand greater stresses without affecting the configuration, and thus the function, of the device.

The first domain can include a macro-architecture and a micro-architecture located within at least a portion of the macro-architecture, such as is described in co-pending U.S. Provisional Patent Application 60/544,722, entitled, "BIOINTERFACE WITH MACRO- AND MICRO-ARCHITECTURE," which is incorporated herein by reference in its entirety. For example, the macro-architecture includes a porous structure with interconnected cavities such as described with reference to the solid portion of the first domain, wherein at least some portion of the cavities of the first domain are filled with the micro-architecture that includes a fibrous or other fine structured material that aids in preventing formation of a barrier cell layer, for example in pockets in the bottom of the cavities of the macro-architecture adjacent to the implantable device.

In certain embodiments, other non-resorbable implant materials can be used in forming the first domain, including but not limited to, metals, ceramics, cellulose, hydrogel polymers, poly(2-hydroxyethyl methacrylate, pHEMA), hydroxyethyl methacrylate, (HEMA), polyacrylonitrile-polyvinyl chloride (PAN-PVC), high density polyethylene, acrylic copolymers, nylon, polyvinyl difluoride, polyanhydrides, poly(l-lysine), poly(L-lactic acid), hydroxyethylmethacrylate, hydroxyapeptite, alumina, zirconia, carbon fiber, aluminum, calcium phosphate, titanium, titanium alloy, nintinol, stainless steel, and CoCr alloy.

Architecture of the Second Domain

FIGS. 2A and 2B, illustrate the second domain of the membrane. The second domain is impermeable to cells or cell processes, and is composed of a biostable material. In one embodiment, the second domain is comprised of polyurethane and a hydrophilic polymer, such as is described in co-pending U.S. application Ser. No. 09/916,858 filed Jul. 27, 2001, which is incorporated herein by reference in its entirety. Alternatively, the hydrophilic polymer can include polyvinylpyrrolidone. Alternatively, the second domain is polyurethane comprising about 5 weight percent or more polyvinylpyrrolidone and about 45 weight percent or more polyvinylpyrrolidone. Alternatively, the second domain comprises about 20 weight percent or more polyvinylpyrrolidone and about 35 weight percent or more polyvinylpyrrolidone. Alternatively, the second domain is polyurethane comprising about 27 weight percent polyvinylpyrrolidone. In certain embodiments, however, the second domain can comprise about 5 weight percent or more than about 45 weight percent polyvinylpyrrolidone.

Alternatively, the second domain can be formed from materials such as copolymers or blends of copolymers with hydrophilic polymers such as polyvinylpyrrolidone (PVP), polyhydroxyethyl methacrylate, polyvinylalcohol, polyacrylic acid, polyethers such as polyethylene glycol, and block copolymers thereof, including, for example, di-block, tri-block, alternating, random and graft copolymers (block copolymers are disclosed in U.S. Pat. Nos. 4,803,243 and 4,686,044). In some embodiments, the second domain can comprise a silicone composition with a hydrophile such as Polyethylene Glycol (PEG) covalently incorporated or grafted therein, such as described in co-pending U.S. patent application Ser. No. 10/695,636, entitled, "SILICONE COMPOSITION FOR BIOCOMPATIBLE MEMBRANE," which is incorporated herein by reference in its entirety. In one embodiment, the second domain is comprised of a silicone copolymer including a hydrophilic component, which can be formed as a unitary structure with the first domain or a separate structure adhered thereto.

In general, the materials preferred for the second domain prevent or hinder cell entry or contact with device elements underlying the membrane and prevent or hinder the adherence of cells, thereby further discouraging formation of a barrier cell layer. Additionally, because of the resistance of the materials to barrier cell layer formation, membranes prepared therefrom are robust long-term in vivo.

The thickness of the cell impermeable biomaterial of the second domain (also referred to as a cell impermeable domain) is typically about 1 µm or more, preferably from about 1, 5, 10, 15, 20, 25, 30, 35, 40, 45, or 50 µm to about 55, 60, 65, 70, 75, 80, 85, 90, 95, 100, 110, 120, 130, 140, 150, 160, 170, 180, 190, or 200 µm. In some embodiments, thicker or thinner cell impermeable domains can be desired. Alternatively, the function of the cell impermeable domain is accomplished by the implantable device, or a portion of the implantable device, which may or may not include a distinct domain or layer.

The characteristics of the cell impermeable membrane prevent or hinder cells from entering the membrane, but permit or facilitate transport of the analyte of interest or a substance indicative of the concentration or presence of the analyte. Additionally the second domain, similar to the first domain, is preferably constructed of a biodurable material (for example, a material durable for a period of several years in vivo) that is impermeable to host cells, for example, macrophages, such as described above.

In embodiments wherein the biointerface membrane is employed in an implantable glucose-measuring device, the biointerface membrane is permeable to oxygen and glucose or a substance indicative of the concentration of glucose. In embodiments wherein the membrane is employed in a drug delivery device or other device for delivering a substance to the body, the cell impermeable membrane is permeable to the drug or other substance dispensed from the device. In embodiments wherein the membrane is employed for cell transplantation, the membrane is semi-permeable, for example, impermeable to immune cells and soluble factors responsible for rejecting transplanted tissue, but permeable to the ingress of glucose and oxygen for the purpose of sustaining the transplanted tissue; additionally, the second domain is permeable to the egress of the gene product of interest (for example, insulin).

The cell disruptive (first) domain and the cell impermeable (second) domain can be secured to each other by any suitable method as is known in the art. For example, the cell impermeable domain can simply be layered or cast upon the porous cell disruptive domain so as to form a mechanical attachment. Alternatively, chemical and/or mechanical attachment methods can be suitable for use. Chemical attachment methods can include adhesives, glues, lamination, and/or wherein a thermal bond is formed through the application of heat and pressure, and the like. Suitable adhesives are those capable of forming a bond between the materials that make up both the barrier cell disruptive domain and the cell impermeable domain, and include liquid and/or film applied adhesives. An appropriate material can be designed that can be used for preparing both domains such that the composite is prepared in one step, thereby forming a unitary structure. For example, when the cell disruptive domain and the cell impermeable domain comprise silicone, the materials can be designed so that they can be covalently cured to one another. However, in some embodiments wherein the second domain comprises a part of the implantable device, it can be attached to or simply lie adjacent to the first domain.

In some embodiments wherein an adhesive is employed, the adhesive can comprise a biocompatible material. However, in some embodiments adhesives not generally considered to have a high degree of biocompatibility can also be employed. Adhesives with varying degrees of biocompatibility suitable for use include acrylates, for example, cyanoacrylates, epoxies, methacrylates, polyurethanes, and other polymers, resins, and crosslinking agents as are known in the art. In some embodiments, a layer of non-woven material (such as ePTFE) is cured to the first domain after which the material is bonded to the second domain, which allows a good adhesive interface between the first and second domains using a biomaterial known to respond well at the tissue-device interface, for example.

Bioactive Agents

The biointerface membranes of the preferred embodiments preferably include a bioactive agent, which is incorporated into at least one of the first and second domains of the biointerface membrane, or which is incorporated into the device and adapted to diffuse through the first and/or second domains, in order to modify the tissue response of the host to the membrane. The architectures of the first and second domains support vascularized tissue growth in or around the biointerface membrane, interfere with and resist barrier cell layer formation, and allow the transport of analytes across the membrane. However, certain outside influences, for example, faulty surgical techniques, acute or chronic movement of the implant, or other surgery-, patient-, and/or implantation site-related conditions, can create acute and/or chronic inflammation at the implant site. When this occurs, the biointerface membrane architecture alone may not be sufficient to overcome the acute and/or chronic inflammation. Alternatively, the membrane architecture can benefit from additional mechanisms that aid in reducing this acute and/or chronic inflammation that can produce a barrier cell layer and/or a fibrotic capsule surrounding the implant, resulting in compromised solute transport through the membrane.

In general, the inflammatory response to biomaterial implants can be divided into two phases. The first phase consists of mobilization of mast cells and then infiltration of predominantly polymorphonuclear (PMN) cells. This phase is termed the acute inflammatory phase. Over the course of days to weeks, chronic cell types that comprise the second phase of inflammation replace the PMNs. Macrophage and lymphocyte cells predominate during this phase. While not wishing to be bound by any particular theory, it is believed that short-term stimulation of vascularization, or short-term inhibition of scar formation or barrier cell layer formation, provides protection from scar tissue formation, thereby providing a stable platform for sustained maintenance of the altered foreign body response.

Accordingly, bioactive intervention can modify the foreign body response in the early weeks of foreign body capsule formation, thereby fundamentally altering the long-term behavior of the foreign body capsule. Additionally, it is believed that the biointerface membranes of the preferred embodiments can advantageously benefit from bioactive intervention to overcome sensitivity of the membrane to implant procedure, motion of the implant, or other factors, which are known to otherwise cause inflammation, scar formation, and hinder device function in vivo.

In general, bioactive agents that are believed to modify tissue response include anti-inflammatory agents, anti-infective agents, anesthetics, inflammatory agents, growth factors, angiogenic (growth) factors, adjuvants, wound factors, resorbable device components, immunosuppressive agents, antiplatelet agents, anticoagulants, ACE inhibitors, cytotoxic agents, anti-barrier cell compounds, vascularization compounds, anti-sense molecules, and the like. In some embodiments, preferred bioactive agents include SIP (Sphingosine-1-phosphate), Monobutyrin, Cyclosporin A, Anti-thrombospondin-2, Rapamycin (and its derivatives), and Dexamethasone. However, other bioactive agents, biological materials (for example, proteins), or even non-bioactive substances can be preferred for incorporation into the membranes of preferred embodiments.

Bioactive agents suitable for use in the preferred embodiments are loosely organized into two groups: anti-barrier cell agents and vascularization agents. These designations reflect functions that are believed to provide short-term solute transport through the biointerface membrane, and additionally extend the life of a healthy vascular bed and hence solute transport through the biointerface membrane long term in vivo. However, not all bioactive agents can be clearly categorized into one or other of the above groups; rather, bioactive agents generally comprise one or more varying mechanisms for modifying tissue response and can be generally categorized into one or both of the above-cited categories.

Anti-Barrier Cell Agents

Generally, anti-barrier cell agents include compounds exhibiting affects on macrophages and foreign body giant cells (FBGCs). It is believed that anti-barrier cell agents prevent closure of the barrier to solute transport presented by macrophages and FBGCs at the device-tissue interface during FBC maturation.

Anti-barrier cell agents generally include mechanisms that inhibit foreign body giant cells and/or occlusive cell layers. For example, Super Oxide Dismutase (SOD) Mimetic, which utilizes a manganese catalytic center within a porphyrin like molecule to mimic native SOD and effectively remove superoxide for long periods, thereby inhibiting FBGC formation at the surfaces of biomaterials in vivo, is incorporated into a biointerface membrane of a preferred embodiment.

Anti-barrier cell agents can include anti-inflammatory and/or immunosuppressive mechanisms that affect the wound healing process, for example, healing of the wound created by the incision into which an implantable device is inserted. Cyclosporine, which stimulates very high levels of neovascularization around biomaterials, can be incorporated into a biointerface membrane of a preferred embodiment [see U.S. Pat. No. 5,569,462 to Martinson et al., which is incorporated herein by reference in its entirety.] Alternatively, Dexamethasone, which abates the intensity of the FBC response at the tissue-device interface, can be incorporated into a biointerface membrane of a preferred embodiment. Alternatively, Rapamycin, which is a potent specific inhibitor of some macrophage inflammatory functions, can be incorporated into a biointerface membrane of a preferred embodiment.

Other suitable medicaments, pharmaceutical compositions, therapeutic agents, or other desirable substances can be incorporated into the membranes of preferred embodiments, including, but not limited to, anti-inflammatory agents, anti-infective agents, and anesthetics.

Generally, anti-inflammatory agents reduce acute and/or chronic inflammation adjacent to the implant, in order to decrease the formation of a FBC capsule to reduce or prevent barrier cell layer formation. Suitable anti-inflammatory agents include but are not limited to, for example, nonsteroidal anti-inflammatory drugs (NSAIDs) such as acetometaphen, aminosalicylic acid, aspirin, celecoxib, choline magnesium trisalicylate, diclofenac potassium, diclofenac sodium, diflunisal, etodolac, fenoprofen, flurbiprofen, ibuprofen, indomethacin, interleukin (IL)-10, IL-6 mutein, anti-IL-6 iNOS inhibitors (for example, L-NAME or L-NMDA), Interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone.

Generally, immunosuppressive and/or immunomodulatory agents interfere directly with several mechanisms necessary for involvement of different cellular elements in the inflammatory response. Suitable immunosuppressive and/or immunomodulatory agents include anti-proliferative, cell-cycle inhibitors, (for example, paclitaxel, cytochalasin D, infiximab), taxol, actinomycin, mitomycin, thospromote VEGF, estradiols, NO donors, QP-2, tacrolimus, tranilast, actinomycin, everolimus, methothrexate, mycophenolic acid, angiopeptin, vincristing, mitomycine, statins, C MYC antisense, sirolimus (and analogs), RestenASE, 2-chloro-deoxyadenosine, PCNA Ribozyme, batimstat, prolyl hydroxylase inhibitors, PPARγ ligands (for example troglitazone, rosiglitazone, pioglitazone), halofuginone, C-proteinase inhibitors, probucol, BCP671, EPC antibodies, catchins, glycating agents, endothelin inhibitors (for example, Ambrisentan, Tesosentan, Bosentan), Statins (for example, Cerivasttin), *E. coli* heat-labile enterotoxin, and advanced coatings.

Generally, anti-infective agents are substances capable of acting against infection by inhibiting the spread of an infectious agent or by killing the infectious agent outright, which can serve to reduce immunoresponse without inflammatory response at the implant site. Anti-infective agents include, but are not limited to, anthelmintics (mebendazole), antibiotics including aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, silver, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim.

Vascularization Agents

Generally, vascularization agents include substances with direct or indirect angiogenic properties. In some cases, vascularization agents can additionally affect formation of barrier cells in vivo. By indirect angiogenesis, it is meant that the angiogenesis can be mediated through inflammatory or immune stimulatory pathways. It is not fully known how agents that induce local vascularization indirectly inhibit barrier-cell formation. However it is believed that some barrier-cell effects can result indirectly from the effects of vascularization agents.

Vascularization agents include mechanisms that promote neovascularization and accelerate wound healing around the membrane and/or minimize periods of ischemia by increasing vascularization close to the tissue-device interface. Sphingosine-1-Phosphate (S1P), which is a phospholipid possessing potent angiogenic activity, is incorporated into a biointerface membrane of a preferred embodiment. Monobutyrin, which is a potent vasodilator and angiogenic lipid product of adipocytes, is incorporated into a biointerface membrane of a preferred embodiment. In another embodiment, an anti-sense molecule (for example, thrombospondin-2 antisense), which increases vascularization, is incorporated into a biointerface membrane.

Vascularization agents can include mechanisms that promote inflammation, which is believed to cause accelerated neovascularization and wound healing in vivo. In one embodiment, a xenogenic carrier, for example, bovine collagen, which by its foreign nature invokes an immune response, stimulates neovascularization, and is incorporated into a biointerface membrane of the preferred embodiments. In another embodiment, Lipopolysaccharide, which is a potent immunostimulant, is incorporated into a biointerface membrane. In another embodiment, a protein, for example, a bone morphogenetic protein (BMP), which is known to modulate bone healing in tissue, is incorporated into a biointerface membrane of a preferred embodiment.

Generally, angiogenic agents are substances capable of stimulating neovascularization, which can accelerate and sustain the development of a vascularized tissue bed at the tissue-device interface. Angiogenic agents include, but are not limited to, Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-Beta), Transforming Growth Factor Alpha (TGF-Alpha), Hepatocyte Growth Factor, Tumor Necrosis Factor-Alpha (TNF-Alpha), Placental Growth Factor (PLGF), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lactic Acid, Insulin, Copper Sulfate, Estradiol, prostaglandins, cox inhibitors, endothelial cell binding agents (for example, decorin or vimentin), glenipin, hydrogen peroxide, nicotine, and Growth Hormone.

Generally, pro-inflammatory agents are substances capable of stimulating an immune response in host tissue, which can accelerate or sustain formation of a mature vascularized tissue bed. For example, pro-inflammatory agents are generally irritants or other substances that induce chronic inflammation and chronic granular response at the wound-site. While not wishing to be bound by theory, it is believed that formation of high tissue granulation induces blood vessels, which supply an adequate or rich supply of analytes to the device-tissue interface. Pro-inflammatory agents include, but are not limited to, xenogenic carriers, Lipopolysaccharides, *S. aureus* peptidoglycan, and proteins.

Other substances that can be incorporated into membranes of preferred embodiments include various pharmacological agents, excipients, and other substances well known in the art of pharmaceutical formulations.

Bioactive Agent Delivery Systems and Methods

There are a variety of systems and methods by which the bioactive agent is incorporated into the biointerface membranes of the preferred embodiments. In some embodiments, the bioactive agent is incorporated at the time of manufacture of the biointerface membrane. For example, the bioactive agent can be blended prior to curing the biointerface membrane, or subsequent to biointerface membrane manufacture, for example, by coating, imbibing, solvent-casting, or sorption of the bioactive agent into the biointerface membrane. Although the bioactive agent is preferably incorporated into the biointerface membrane, in some embodiments the bioactive agent can be administered concurrently with, prior to, or after implantation of the device systemically, for example, by oral administration, or locally, for example, by subcutaneous injection near the implantation site. A combination of bioactive agent incorporated in the biointerface membrane and bioactive agent administration locally and/or systemically can be preferred in certain embodiments.

The biointerface membranes of the preferred embodiments preferably include a bioactive agent, which is incorporated into at least one of the first and second domains of the biointerface membrane, and/or which is incorporated into the device and adapted to diffuse through the first and/or second domains, in order to modify the tissue response of the host to the membrane. In some embodiments wherein the biointerface membrane is used with an analyte-measuring device, the bioactive agent is incorporated only into a portion of the biointerface membrane adjacent to the sensing region of the device, over the entire surface of the device except over the sensing region, or any combination thereof, which can be helpful in controlling different mechanisms and/or stages of the maturation of the FBC. In some alternative embodiments however, the bioactive agent is incorporated into the implantable device proximal to the biointerface membrane, such that the bioactive agent diffuses through the biointerface membrane to the host tissue.

The bioactive agent can include a carrier matrix, wherein the matrix includes one or more of collagen, a particulate matrix, a resorbable or non-resorbable matrix, a controlled-release matrix, and/or a gel. In some embodiments, the carrier matrix includes a reservoir, wherein a bioactive agent is encapsulated within a microcapsule. The carrier matrix can include a system in which a bioactive agent is physically entrapped within a polymer network. In some embodiments, the bioactive agent is cross-linked with the biointerface membrane, while in others the bioactive agent is sorbed into the biointerface membrane, for example, by adsorption, absorption, or imbibing. The bioactive agent can be deposited in or on the biointerface membrane, for example, by coating, filling, or solvent casting. In certain embodiments, ionic and nonionic surfactants, detergents, micelles, emulsifiers, demulsifiers, stabilizers, aqueous and oleaginous carriers, solvents, preservatives, antioxidants, or buffering agents are used to incorporate the bioactive agent into the biointerface membrane. The bioactive agent can be incorporated into a polymer using techniques such as described above, and the polymer can be used to form the biointerface membrane, coatings on the biointerface membrane, portions of the biointerface membrane, and/or a portion of an implantable device.

The biointerface membrane can be manufactured using techniques known in the art. The bioactive agent can be sorbed into the biointerface membrane, for example, by soaking the biointerface membrane for a length of time (for example, from about an hour or less to about a week or more, preferably from about 4, 8, 12, 16, or 20 hours to about 1, 2, 3, 4, 5, or 7 days). Absorption of Dexamethasone into a porous silicone membrane is described in the experimental section.

The bioactive agent can be blended into uncured polymer prior to forming the biointerface membrane. The biointerface membrane is then cured and the bioactive agent thereby cross-linked and/or encapsulated within the polymer that forms the biointerface membrane. For example, Monobutyrin was covalently bonded to a silicone matrix in such a manner that is slowly cleavable under in vivo conditions. The alcohol groups of Monobutyrin react with a silanol group, resulting in a C—O—Si bond. This bond is known to be susceptible to hydrolysis, and is therefore cleaved to yield the original alcohol and silanol. Thus, the Monobutyrin is released from the silicone matrix according to the rate of hydrolysis. Other bioactive agents, such as Dexamethasone, comprise alcohol groups and can be bound to a silicone matrix in a similar manner.

In yet another embodiment, microspheres are used to encapsulate the bioactive agent. The microspheres can be formed of biodegradable polymers, most preferably synthetic polymers or natural polymers such as proteins and polysaccharides. As used herein, the term polymer is used to refer to both to synthetic polymers and proteins. U.S. Pat. No. 6,281,015, which is incorporated herein by reference in its entirety, discloses some systems and methods that can be used in conjunction with the preferred embodiments. In general, bioactive agents can be incorporated in (1) the polymer matrix forming the microspheres, (2) microparticle(s) surrounded by the polymer which forms the microspheres, (3) a polymer core within a protein microsphere, (4) a polymer coating around a polymer microsphere, (5) mixed in with microspheres aggregated into a larger form, or (6) a combination thereof. Bioactive agents can be incorporated as particulates or by co-dissolving the factors with the polymer. Stabilizers can be incorporated by addition of the stabilizers to the factor solution prior to formation of the microspheres.

The bioactive agent can be incorporated into a hydrogel and coated or otherwise deposited in or on the biointerface membrane. Some hydrogels suitable for use in the preferred embodiments include cross-linked, hydrophilic, three-dimensional polymer networks that are highly permeable to the bioactive agent and are triggered to release the bioactive agent based on a stimulus.

The bioactive agent can be incorporated into the biointerface membrane by solvent casting, wherein a solution including dissolved bioactive agent is disposed on the surface of the biointerface membrane, after which the solvent is removed to form a coating on the membrane surface.

In yet another embodiment, the interconnected cavities of the biointerface membrane are filled with the bioactive agent. Preferably, a bioactive agent, with or without a carrier matrix, fills the cavities of the membrane, depending on the loading and release properties desired, which are discussed in more detail below.

The bioactive agent can be compounded into a plug of material, which is placed within the implantable device, such as is described in U.S. Pat. Nos. 4,506,680 and 5,282,844, which are incorporated herein by reference in their entirety. In contrast to the method disclosed in U.S. Pat. Nos. 4,506,680 and 5,282,844, in the preferred embodiments it is preferred to dispose the plug beneath a membrane system, for example, beneath the sensing membrane or biointerface membrane. In this way, the bioactive agent is controlled by diffusion through the membrane, which provides a mechanism for sustained-release of the bioactive agent long-term in the host.

Release of Bioactive Agents

Numerous variables can affect the pharmacokinetics of bioactive agent release. The bioactive agents of the preferred embodiments can be optimized for short- and/or long-term release. In some embodiments, the bioactive agents of the preferred embodiments are designed to aid or overcome factors associated with short-term effects (for example, acute inflammation) of the foreign body response, which can begin as early as the time of implantation and extend up to about one month after implantation. In some embodiments, the bioactive agents of the preferred embodiments are designed to aid or overcome factors associated with long-term effects, for example, chronic inflammation, barrier cell layer formation, or build-up of fibrotic tissue of the foreign body response, which can begin as early as about one week after implantation and extend for the life of the implant, for example, months to years. In some embodiments, the bioactive agents of the preferred embodiments combine short- and long-term release to exploit the benefits of both.

As used herein, "controlled," "sustained," or "extended" release of the factors can be continuous or discontinuous, linear or non-linear. This can be accomplished using one or more types of polymer compositions, drug loadings, selections of excipients or degradation enhancers, or other modifications, administered alone, in combination or sequentially to produce the desired effect.

Short-term release of the bioactive agent in the preferred embodiments generally refers to release over a period of from about 1 day or less to about 2, 3, 4, 5, 6, or 7 days, 2 or 3 weeks, 1 month, or more. More preferably, the short-term release of the bioactive agent occurs over from about 14, 15, 16, 17, or 18 days up to about 19, 20, or 21 days.

Conventional devices, such as implantable analyte measuring-devices, drug delivery devices, and cell transplantation devices that require transport of solutes across the device-tissue interface for proper function, tend to lose their function after the first few days following implantation. At least one reason for this loss of function is the lack of direct contact with circulating fluid for appropriate analyte transport to the device. Therefore, in some embodiments, short-term release of certain bioactive agents, for example vascularization agents, can increase the circulating fluid to the device for an extended period of time.

Additionally, it is believed that short-term release of the bioactive agent can have a positive effect of the functionality of porous biointerface membranes during the initial tissue ingrowth period prior to formation of a capillary bed. For example, when a device requiring analyte transport across its device-tissue interface is implanted, a "sleep period" can occur which begins as early as the first day after implantation and extends as far as one month after implantation. However shorter sleep periods are more common. During this sleep period, extensive ingrowth of tissue into the porous structure causes the inflammatory cells responsible for facilitating wound healing to proliferate within the local environment of the wound region. Because these cells are respiring, they consume some or all of the glucose and oxygen that is within the wound environment, which has shown to block adequate flow of analytes to the implantable device. Accordingly in some embodiments, it is believed that short-term release of certain bioactive agents, for example vascularization agents, can aid in providing adequate vascularization to substantially overcome the effects of the sleep period, and thereby allow sufficient analytes to pass through to the implantable device.

Additionally, it is believed that short-term release of the bioactive agent can have an enhanced effect on neovascularization at the tissue-device interface. Although neovascularization alone is generally not sufficient to provide sufficient analyte transport at the device-tissue interface, in combination with other mechanisms, enhanced neovascularization can result in enhanced transport of analytes from the host to the implanted device. Therefore in some embodiments, short-term release of certain bioactive agents, for example angiogenic agents, can have a positive effect on neovascularization and thereby enhance transport of analytes at the device-tissue interface.

Additionally, it is believed that short-term release of the bioactive agent can be sufficient to reduce or prevent barrier cell layer formation. Formation of a cohesive monolayer of closely opposed cells, e.g. macrophages and foreign body giant cells, interfere with the transport of analytes across the tissue-device interface, also known as a barrier cell layer, and are large contributors to poor device performance. See U.S. Pat. No. 6,702,857, which is incorporated herein by reference in its entirety. Therefore in some embodiments, it is believed that short-term release of certain bioactive agents, for example, anti-barrier cell agents, can aid in preventing barrier cell layer formation.

Additionally, it is believed that short-term release of the bioactive agent can be sufficient to prevent negative effects of acute inflammation caused, for example, by surgical trauma, micro-motion, or macro-motion of the device in the soft tissue. Short-term release of anti-inflammatory agents can be sufficient to rescue a biointerface membrane from the negative effects associated with such acute inflammation, rendering adequate analyte transport.

Long-term release of the bioactive agent in the preferred embodiments generally occurs over a period of from about 1 month to about 2 years or more, preferably from at least about 2 months to at least about 13, 14, 15, 16, 17, 18, 19, 20, 21, 22, or 23 months, and more preferably from at least about 3 months to at least about 4, 5, 6, 7, 8, 9, 10, 11, or 12 months.

Long-term glucose-measuring device experiments demonstrate that many biointerface materials experience a distinct and continual decline in sensitivity, for example, reduced analyte transport, beginning at three months after implantation in some cases. It is believed that this decline in analyte transport can be a result of barrier cell layer formation, cellular growth at the membrane, and/or thickening of the fibrous elements of the foreign body capsule. Other contributing factors can include chronic inflammation, which is believed to be due to micro-motion or macro-motion of the device; delamination of the biointerface membrane, which is believed to be due to cellular ingrowth within and under the biointerface membrane; compression of the biointerface membrane due to increasing compression of the foreign body capsule around the device; and distortion of the biointerface membrane, which is believed to be a result of a combination of compression and cellular ingrowth, for example.

Accordingly, long-term release of certain bioactive agents can modulate the foreign body response sufficiently to prevent long-term thickening of the foreign body capsule, reduce or prevent barrier cell layer formation, reduce or prevent chronic inflammation, reduce or prevent extensive cellular ingrowth, and/or reduce or prevent compression of the foreign body capsule on the biointerface membrane.

Loading of Bioactive Agents

The amount of loading of the bioactive agent into the biointerface membrane can depend upon several factors. For example, the bioactive agent dosage and duration can vary with the intended use of the biointerface membrane, for example, cell transplantation, analyte measuring-device, and the like; differences among patients in the effective dose of bioactive agent; location and methods of loading the bioactive agent; and release rates associated with bioactive agents and optionally their carrier matrix. Therefore, one skilled in the art will appreciate the variability in the levels of loading the bioactive agent, for the reasons described above.

In some embodiments, wherein the bioactive agent is incorporated into the biointerface membrane without a carrier matrix, the preferred level of loading of the bioactive agent into the biointerface membrane can vary depending upon the nature of the bioactive agent. The level of loading of the bioactive agent is preferably sufficiently high such that a biological effect is observed. Above this threshold, bioactive agent can be loaded into the biointerface membrane so as to imbibe up to 100% of the solid portions, cover all accessible surfaces of the membrane, and/or fill up to 100% of the accessible cavity space. Typically, the level of loading (based on the weight of bioactive agent(s), biointerface membrane, and other substances present) is from about 1 ppm or less to about 1000 ppm or more, preferably from about 2, 3, 4, or 5 ppm up to about 10, 25, 50, 75, 100, 200, 300, 400, 500, 600, 700, 800, or 900 ppm. In certain embodiments, the level of loading can be 1 wt. % or less up to about 50 wt. % or more, preferably from about 2, 3, 4, 5, 6, 7, 8, 9, 10, 15, or 20 wt. % up to about 25, 30, 35, 40, or 45 wt. %.

When the bioactive agent is incorporated into the biointerface membrane with a carrier matrix, such as a gel, the gel concentration can be optimized, for example, loaded with one or more test loadings of the bioactive agent. It is generally preferred that the gel contain from about 0.1 or less to about 50 wt. % or more of the bioactive agent(s), preferably from about 0.2, 0.3, 0.4, 0.5, 0.6, 0.7, 0.8, or 0.9 wt. % to about 6, 7, 8, 9, 10, 15, 20, 25, 30, 35, 40, or 45 wt. % or more bioactive agent(s), more preferably from about 1, 2, or 3 wt. % to about 4 or 5 wt. % of the bioactive agent(s). Substances that are not bioactive can also be incorporated into the matrix.

Referring now to microencapsulated bioactive agents, the release of the agents from these polymeric systems generally occur by two different mechanisms. The bioactive agent can be released by diffusion through aqueous filled channels generated in the dosage form by the dissolution of the agent or by voids created by the removal of the polymer solvent or a pore forming agent during the original micro-encapsulation. Alternatively, release can be enhanced due to the degradation of the polymer. With time, the polymer erodes and generates increased porosity and microstructure within the device. This creates additional pathways for release of the bioactive agent.

Implantable Devices

Biointerface membranes of the preferred embodiments are suitable for use with implantable devices in contact with a biological fluid. For example, the biointerface membranes can be utilized with implantable devices and methods for monitoring and determining analyte levels in a biological fluid, such as measurement of glucose levels for individuals having diabetes. In some embodiments, the analyte-measuring device is a continuous device. Alternatively, the device can analyze a plurality of intermittent biological samples. The analyte-measuring device can use any method of analyte-measurement, including enzymatic, chemical, physical, electrochemical, spectrophotometric, polarimetric, calorimetric, radiometric, or the like.

Although some of the description that follows is directed at glucose-measuring devices, including the described biointerface membranes and methods for their use, these biointerface membranes are not limited to use in devices that measure or monitor glucose. These biointerface membranes are suitable for use in a variety of devices, including, for example, those that detect and quantify other analytes present in biological fluids (including, but not limited to, cholesterol, amino acids, and lactate), cell transplantation devices (see, e.g. U.S. Pat. Nos. 6,015,572, 5,964,745, and 6,083,523), drug delivery devices (see, e.g. U.S. Pat. Nos. 5,458,631, 5,820,589, and 5,972,369) and electrical delivery and/or measuring devices such as implantable pulse generation cardiac pacing devices (see, e.g. U.S. Pat. Nos. 6,157,860, 5,782,880, and 5,207,218), electrocardiogram devices (see, e.g. U.S. Pat. Nos. 4,625,730 and 5,987,352) electrical nerve stimulating devices (see, e.g. U.S. Pat. Nos. 6,175,767, 6,055,456, and 4,940,065), and in combination with angiogenic factor gene transfer technology to enhance implantable device function (see, e.g. Klueh U, Dorsky D I, Kreutzer D L. Use of vascular endothelial cell growth factor gene transfer to enhance implantable device function in vivo. J. Biomed. Mater. Res. 2003 Dec. 15; 67A(4):1072-86), to name but a few. The biointerface membranes can be utilized in conjunction with transplanted cells, for example, transplanted genetic engineered cells of Langerhans, either allo, auto or xeno geneic in origin, as pancreatic beta cells to increase the diffusion of nutrients to the islets, but additionally utilizing a biointerface membrane of the preferred embodiment on a measuring-device proximal to the transplanted cells to sense glucose in the tissues of the patient to monitor the viability of the implanted cells. Preferably, implantable devices that include the biointerface membranes of the preferred embodiments are implanted in soft tissue, for example, abdominal, subcutaneous, and peritoneal tissues, the brain, the intramedullary space, and other suitable organs or body tissues.

In addition to the glucose-measuring device described below, the biointerface membranes of the preferred embodiments can be employed with a variety of known continuous glucose measuring-devices. For example, the biointerface membrane can be employed in conjunction with a continuous glucose measuring-device that comprises a subcutaneous measuring-device such as is described in U.S. Pat. No. 6,579,690 to Bonnecaze et al. and U.S. Pat. No. 6,484,046 to Say et al. In another alternative embodiment, the continuous glucose measuring-device comprises a refillable subcutaneous measuring-device such as is described in U.S. Pat. No. 6,512,939 to Colvin et al. Indeed, the teachings of the preferred embodiments can be used with virtually any monitoring device suitable for implantation (or subject to modification allowing implantation); additional examples include, but are not limited, to those described in U.S. Pat. Nos. 4,703,756 and 4,994,167 to Shults et al.; U.S. Pat. No. 4,703,756 to Gough et al., and U.S. Pat. No. 4,431,004 to Bessman et al.; the contents of each being hereby incorporated by reference, and Bindra et al., Anal. Chem. 63:1692-96 (1991). All of the above patents are incorporated in their entirety herein by reference. In general, it is understood that the disclosed embodiments are applicable to a variety of continuous glucose measuring-device configurations.

Implantable devices for detecting the presence of an analyte or analyte concentrations in a biological system can utilize the biointerface membranes of the preferred embodiments to increase local vascularization and interfere with the formation of a barrier cell layer, thereby assuring that the measuring-device receives analyte concentrations representative of that in the vasculature. Drug delivery devices can utilize the biointerface membranes of the preferred embodiments to protect the drug housed within the device from host inflammatory or immune cells that might potentially damage or destroy the drug. In addition, the biointerface membrane can prevent or hinder the formation of a barrier cell layer that can interfere with proper dispensing of drug from the device for treatment of the host. Correspondingly, cell transplantation devices can utilize the biointerface membranes of the preferred embodiments to protect the transplanted cells from attack by the host inflammatory or immune response cells while simultaneously preventing the formation of a barrier cell layer, thereby permitting nutrients as well as other biologically active molecules needed by the cells for survival to diffuse through the membrane.

Figure 3:
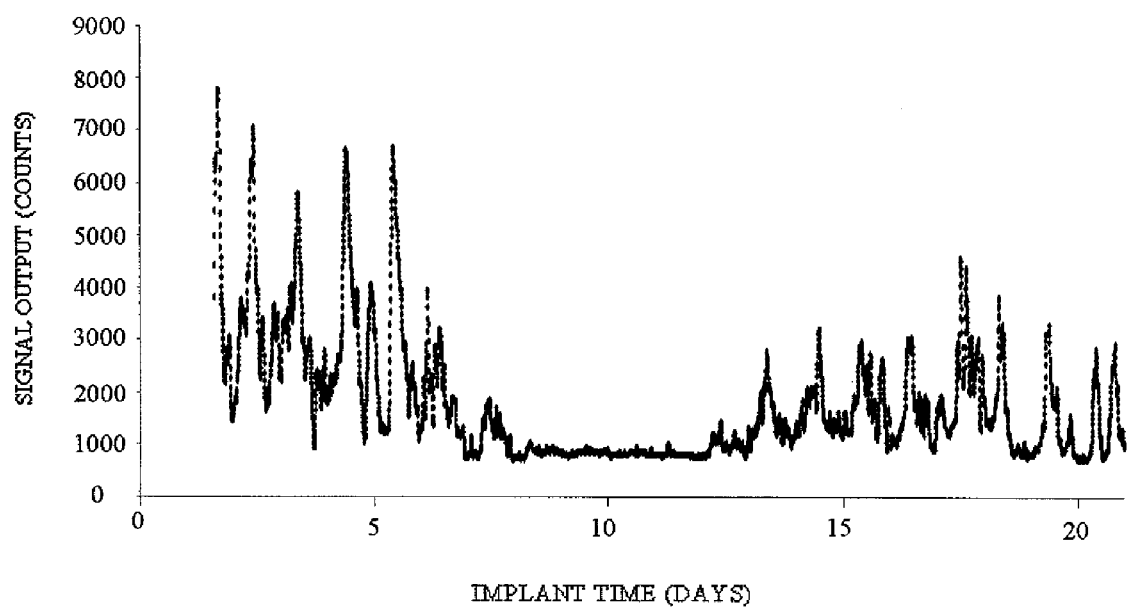
FIG. 3 is a graph of sensor output from a glucose sensor implanted in a human, showing the raw data signal from the sensor from time of implant up to about 21 days after implant.

FIG. 3 is a graph of signal output from a glucose-measuring device implanted in a human, wherein the device included a biointerface membrane without a bioactive agent incorporated therein. The graph shows the data signal produced by the device from time of implant up to about 21 days after implant. The x-axis represents time in days; the y-axis presents the data signal from the device output in counts. The term "counts," as used herein, is a broad term and is used in its ordinary sense, including, without limitation, a unit of measurement of a digital signal. In one example, a raw data signal measured in counts is directly related to a voltage (converted by an A/D converter), which is directly related to current. The glucose-measuring device of this experiment is described in more detail with reference to FIGS. 4A and 4B.

Referring to FIG. 3, the device associated with the signal output was implanted during day 1. The associated signal output is shown beginning at day 1 and substantially tracks the rise and fall of the patient's glucose levels during the first few days after implant. It is noted that approximately 5 days after device implant, the signal output experienced a temporary decrease in sensitivity, sometimes referred to as a "sleep period." It is believed that this loss in sensitivity is due to migration of cells, which consume glucose and oxygen during formation of a vascularized foreign body capsule (tissue bed) into and around the biointerface membrane. In this example, the sleep period continues for approximately 7 days during which time the glucose-measuring device does not accurately track the patient's glucose levels. Approximately 12 days after implant, the signal output resumes function, as indicated by the rise and fall of the signal output, which correlates with the rise and fall the patient's glucose levels. It is believed that this resuming of signal output correlates with a reduction in the numbers of inflammatory cells and a mature vascularized tissue bed within and around the biointerface membrane that allows glucose and oxygen to transport through the biointerface membrane to the glucose-measuring device. The difference in sensitivity of the device before and after the sleep period is attributed to the effect of the vascularized tissue bed on the transport of glucose and oxygen therethrough. In summary, it has been shown that the implantable device with a biointerface membrane but without a bioactive agent incorporated therein sometimes undergoes a sleep period in the device during the formation of the vascularized tissue bed and/or a foreign body capsule surrounding and within the implant.

In order to overcome the sleep period described above, it is believed that by incorporating bioactive agents that enhance local vascularization and inhibit inflammatory cells within or around the biointerface membranes of the preferred embodiments on implanted devices, accelerated maturation of a vascularized tissue bed and decreased inflammatory response will occur, which increases the rate at which devices become functional, reducing or eliminating the loss insensitivity seen in the experiment above. The bioactive agents that are incorporated into the biointerface membrane 30 used on implantable devices of certain preferred embodiments are chosen to optimize the rate of biointerface formation.

In some embodiments, the bioactive agents that are incorporated into the biointerface membrane 30 used on implantable devices are chosen to optimize reliable biointerface formation. In some situations, stable device function does not occur due to faulty surgical techniques, acute or chronic movement of the implant, or other surgery-, patient-, or implantation site-related complications, which can create acute and/or chronic inflammation at the implant site and subsequent formation of barrier cell layer and/or thick fibrotic tissue build-up. While not wishing to be bound by theory, it is believed that bioactive agents described in the preferred embodiments, for example anti-inflammatory agents and/or anti-barrier cell agents, can provide sufficient biological activity to reduce the effects of site-related complications, and thereby increase reliability of device functionality.

In some embodiments, the bioactive agents that are incorporated into the biointerface membrane 30 used on implantable devices are chosen to optimize the stability of the biointerface. Even after devices have been implanted for some length of time and begin to function, it is observed that device stability can be lost gradually or suddenly. It is believed that this loss of stability or function can be attributed the biointerface, based on post-explantation histological examinations. This conclusion is further supported by the observation that devices typically function in vitro after removal from animals or humans. It is therefore believed that delivery of bioactive agents described in the preferred embodiments can increase the stability of the biointerface so that device calibration values remain sufficiently stable so as to provide accurate measurements.

Figure 4A:
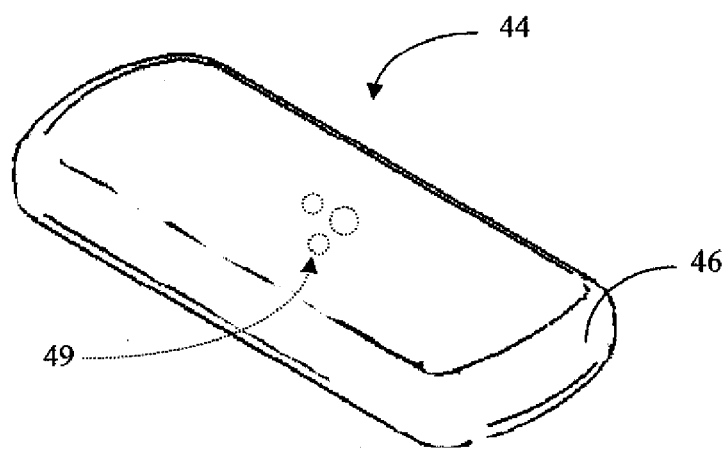
FIG. 4A is a perspective view of an assembled glucose-measuring device, including sensing and biointerface membranes incorporated thereon.
Figure 4B:
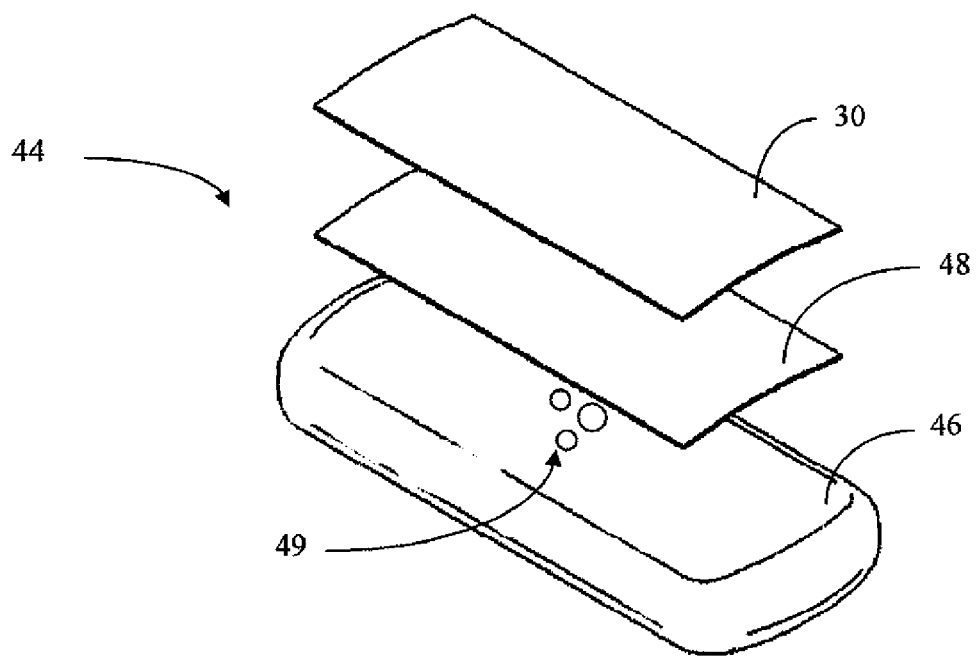
FIG. 4B is an exploded perspective view of the glucose-measuring device of FIG. 4A, showing the sensing membrane and the biointerface membrane.

FIGS. 4A and 4B are perspective views of an implantable glucose measuring-device of one preferred embodiment. FIG. 4A is a view of the assembled glucose measuring-device, including sensing and biointerface membranes incorporated thereon. FIG. 4B is an exploded view of the glucose measuring-device 44, showing the body 46, the sensing membrane 48, and the biointerface membrane 30 of a preferred embodiment, such as is described in more detail above.

The body 46 is preferably formed from epoxy molded around the measuring-device electronics (not shown), however the body can be formed from a variety of materials, including metals, ceramics, plastics, or composites thereof. Co-pending U.S. patent application Ser. No. 10/646,333, entitled, "Optimized Device Geometry for an Implantable Glucose Device" discloses suitable configurations suitable for the body 46, and is incorporated by reference in its entirety.

In one preferred embodiment, the measuring-device 44 is an enzyme-based measuring-device, which includes an electrode system 49 (for example, a platinum working electrode, a platinum counter electrode, and a silver/silver chloride reference electrode), which is described in more detail with reference to U.S. patent application Ser. No. 09/916,711, entitled "Sensor head for use with implantable devices," which is incorporated herein by reference in its entirety. However, a variety of electrode materials and configurations can be used with the implantable glucose measuring-devices of the preferred embodiments. The top ends of the electrodes are in contact with an electrolyte phase (not shown), which is a free-flowing fluid phase disposed between a sensing membrane 48 and the electrode system 49. In this embodiment, the counter electrode is provided to balance the current generated by the species being measured at the working electrode. In the case of a glucose oxidase based glucose measuring-device, the species measured at the working electrode is $H_2O_2$. Glucose oxidase catalyzes the conversion of oxygen and glucose to hydrogen peroxide and gluconate according to the following reaction:

$$Glucose + O_2 \rightarrow Gluconate + H_2O_2$$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons (2H), two electrons ($2e^-$), and one oxygen molecule ($O_2$).

In this embodiment, a potentiostat is employed to monitor the electrochemical reaction at the electroactive surface(s). The potentiostat applies a constant potential to the working and reference electrodes to determine a current value. The current that is produced at the working electrode (and flows through the circuitry to the counter electrode) is substantially proportional to the amount of $H_2O_2$ that diffuses to the working electrode. Accordingly, a raw signal can be produced that is representative of the concentration of glucose in the user's body, and therefore can be utilized to estimate a meaningful glucose concentration.

Figure 5A:
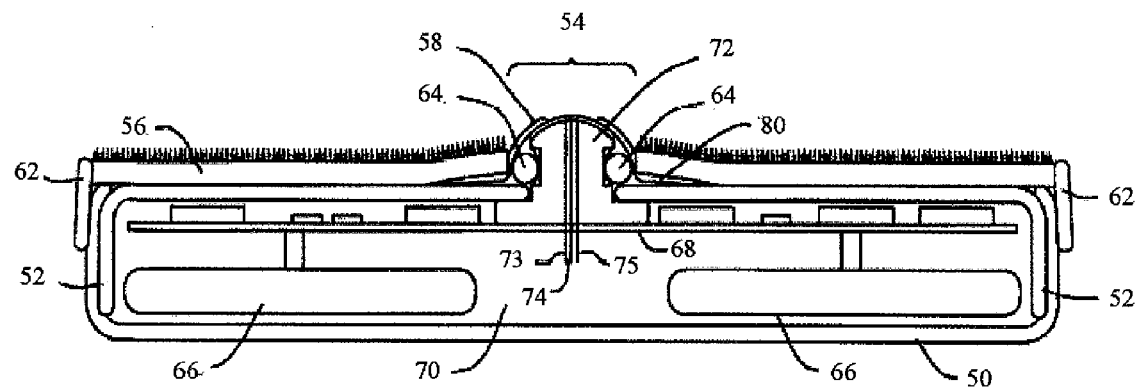
FIG. 5A depicts a cross-sectional drawing of one embodiment of an implantable analyte measuring device of a preferred embodiment.
Figure 5B:
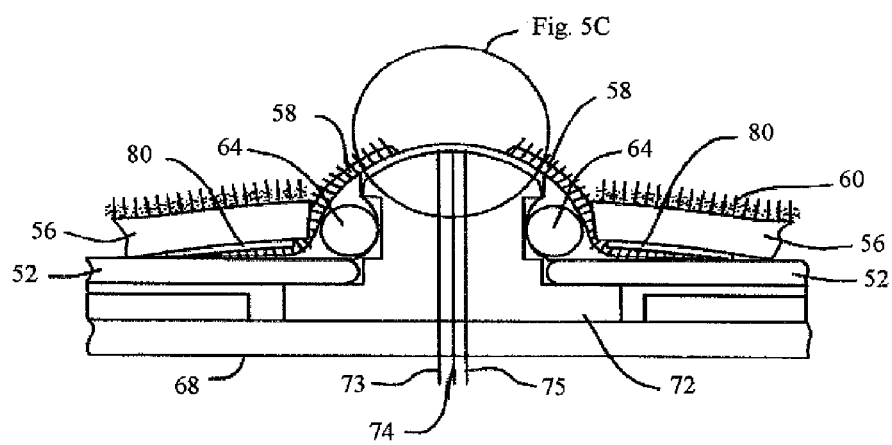
FIG. 5B depicts a cross-sectional exploded view of the sensor interface dome of FIG. 5A.
Figure 5C:
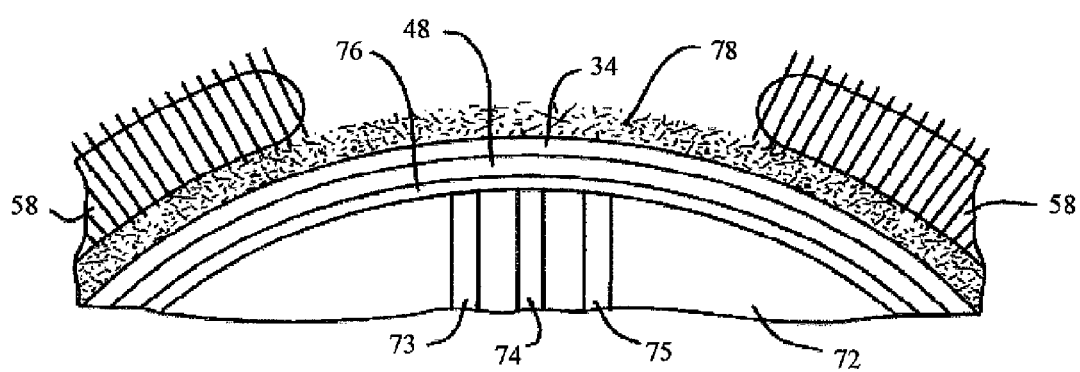
FIG. 5C depicts a cross-sectional exploded view of the electrode-membrane region of FIG. 5B detailing the sensor tip and the functional membrane layers.

In some embodiments, the sensing membrane 48, also referred to as the enzyme membrane, includes an enzyme, for example, glucose oxidase, and covers the electrolyte phase. The sensing membrane 48 preferably includes a resistance domain most distal from the electrochemically reactive surfaces, an enzyme domain less distal from the electrochemically reactive surfaces than the resistance domain, and an electrolyte domain adjacent to the electrochemically reactive surfaces. However, it is understood that a sensing membrane 48 modified for other devices, for example, by including fewer or additional domains, is within the scope of the preferred embodiments. Copending U.S. patent appl. Ser. No. 10/838,912 filed May 3, 2004 and entitled, "IMPLANTABLE ANALYTE SENSOR" and U.S. patent application Ser. No. 09/916,711, entitled, "SENSOR HEAD FOR USE WITH IMPLANTABLE DEVICES," each of which are incorporated herein by reference in their entirety, describes membranes that can be used in some embodiments of the sensing membrane 48. In some embodiments, the sensing membrane 48 can additionally include an interference domain that blocks some interfering species; such as described in the above-cited co-pending patent application. FIGS. 5A to 5C illustrate one configuration for the sensing membrane, and is described in more detail with reference to FIG. 5C below. Co-pending U.S. patent application Ser. No. 10/695,636, entitled, "SILICONE COMPOSITION FOR BIOCOMPATIBLE MEMBRANE" also describes membranes that can be used for the sensing membrane 48 of the preferred embodiments, and is incorporated herein by reference in its entirety.

The biointerface membrane 30 includes a biointerface membrane of a preferred embodiment, which covers the sensing membrane and supports tissue ingrowth, interferes with the formation of a barrier cell layer, and protects the sensitive regions of the measuring-device 44 from host inflammatory response. Preferably, the biointerface membrane 30 is a formed from a non-resorbable membrane and includes a porous architecture with a bioactive agent incorporated therein.

The biointerface membranes of the preferred embodiments can incorporate a variety of mechanisms, including materials, architecture, cavity size, and incorporation of one or bioactive agents, which can be function alone or in combination to enhance wound healing, which when incorporated into an analyte measuring-device, result in enhanced device performance.

In one embodiment, an anchoring material (not shown) is formed substantially around the device body in order to stabilize the device in vivo. Controlled release of a bioactive agent from the biointerface membrane 30, such as an anti-inflammatory agent, is provided for a period of time up to about one month, which is believed to be sufficient to reduce the effects of tissue trauma at the device interface prior to stabilization of the device in vivo. Consequently, when the device is stable (for example, when sufficient tissue ingrowth into the anchoring material occurs to ensure minimal motion and less broken fat cells, seepage and other inflammatory factors), it is safe to permit the biointerface to heal with good vascularization.

FIG. 5A is a cross-sectional view of an alternative embodiment of an implantable analyte-measuring device. FIG. 5B depicts a cross-sectional exploded view of the sensor interface dome of FIG. 5A. FIG. 5C depicts a cross-sectional exploded view of the electrode-membrane region of FIG. 5B detailing the sensor tip and the functional membrane layers. It is noted that this illustrates an exemplary embodiment, and can be modified.

Referring now to the architectural arrangement around the sensor interface of the implantable device of the embodiment of FIGS. 5A to 5C, this embodiment contemplates the use of materials covering all or a portion of the device to assist in the stabilization of the device following implantation. However, it should be pointed out that the preferred embodiments do not require a device comprising particular electronic components (e.g. electrodes, circuitry, and the like). In the discussion that follows, an example of an implantable device that includes the features of the preferred embodiments is first described. Thereafter, the components in and around the sensor interface region are described in more detail.

This embodiment illustrates an oval-shaped device; however, devices with other shapes can also be used with the preferred embodiments. Copending U.S. patent application Ser. No. 10/646,333 entitled, "OPTIMIZED SENSOR GEOMETRY FOR AN IMPLANTABLE GLUCOSE SENSOR," which is incorporated herein by reference in its entirety, describes some configurations suitable for implantable devices of the preferred embodiments. The device includes a housing having an upper portion and a lower portion, which together define a cavity. Referring to FIG. 5A, the device comprises a main housing (also referred to as casing or packaging) consisting of a bottom member 50 with upwardly angled projecting extensions along its perimeter. The four downwardly projecting extensions of a similarly shaped top member 52 engage the upwardly projecting extensions of the bottom member 50. As indicated in FIG. 5A, there is an aperture in top member 52 that allows for protrusion of the sensor interface dome 54. While this embodiment is preferably configured with a protrusion of the sensor interface dome 54; in some embodiments, a precise understanding of the effect of the protrusion is not required in order to practice the preferred embodiments, the protrusion is believed to assist in the formation of vasculature in the sensor interface dome 54 region, and hence presentation of sample to the electrodes.

In certain embodiments, a top member sheath 56 covers the top member 52; like the top member 52, the top member sheath 56 has an aperture, which allows the sensor interface dome 56 to protrude therethrough. As indicated in detail in FIG. 5B, the top member sheath 56 angles upward as it approaches the aperture, allowing the sensor interface capsular attachment layer 58 to be secured thereto. The top member sheath 56 can be coated with a sheath capsular attachment layer 60; in some embodiments, the sheath capsular attachment layer extends beyond the top member sheath (e.g. it can jacket the sides of the device or the bottom member).

Maintaining the blood supply near an implanted foreign body like an implanted analyte-monitoring sensor requires stable fixation of FBC tissue on the surface of the foreign body. This can be achieved, for example, by using capsular attachment membrane materials (e.g. those materials that comprise the sensor interface and top member capsular attachment layers) developed to repair or reinforce tissues, including, but not limited to, polyester (DACRON™; DuPont; poly(ethylene terephthalate)) velour, expanded polytetrafluoroethylene (TEFLON™; Gore), polytetrafluoroethylene felts, polypropylene cloth, and related porous implant materials. In this embodiment, the preferred material for FBC attachment is surgical-grade polyester velour. FBC tissue tends to aggressively grow into the materials disclosed above and form a strong mechanical bond (i.e., capsular attachment); this fixation of the implant in its capsule prevents motion artifact or disturbance of the newly developed capillary blood supply. In preferred embodiments, capsular attachment materials are not used in the region of the sensor interface so as not to interfere with the vasculature development in that region.

Side braces 62 secure the top member sheath 56 to the bottom member 50 (see FIG. 5A). A conventional O-ring 64 or other suitable mechanical means can be used to assist in the attachment of the membrane layers (e.g. the enzyme layer). In a preferred embodiment, the housing is approximately 1.4 cm from the base of the bottom member 50 to the top of the sheath capsular attachment layer 60, and approximately 7.0 cm in length.

The interior (i.e., the cavity) of the housing comprises one or more batteries 66 operably connected to an electronic circuit means (e.g. a circuit board 68), which, in turn, is operably connected to at least one electrode (described below); in preferred embodiments, at least two electrodes are carried by the housing. Any electronic circuitry and batteries that renders reliable, continuous, long-term (e.g. months to years) results can be used in conjunction with the devices of the preferred embodiments.

In this embodiment, the housing preferably utilizes a simple, low-cost packaging technique which protects the components of the device for at least one year in aqueous media. In some preferred embodiments, the components of the housing (e.g. the top and bottom members) comprise thermoformed high-density polyethylene. The area in the cavity of the housing that surrounds the batteries, electronic circuitry, and the like, can be filled with an encapsulant 70 (see FIG. 5A), a material that secures in place the components within the cavity but that does not interfere with the operation of those components. In some preferred embodiments, the encapsulant 70 is based on mixtures of petroleum wax and low melting temperature resins developed for the hot-melt glue industry [Shults et al., IEEE Trans. Biomed. Eng. 41:937-942 (1994). In addition to the high-quality moisture barrier formed with this approach, the electronics (e.g. the circuit board 68) can be recycled by remelting and draining the encapsulant when the battery expires.

In this embodiment, preferred encapsulant compositions include approximately 54% PW 130/35H wax (Astor Wax), approximately 40% MVO 2528 resin (Exxon Chemical), and approximately 6% XS 93.04 resin (Exxon Chemical, Houston, Tex.). These pelletized compounds render a well-mixed solution after heating and mixing at about 120° C. for approximately one hour. This solution is then poured into the polyethylene housing containing the implant electronics, taking caution to not to exceed the burst temperature of, e.g. approximately 160° C. when lithium batteries are used, for example.

FIG. 5B depicts a cross-sectional exploded view of the sensor interface dome 54 of FIG. 5A. Referring to FIG. 5B, the sensor interface dome comprises a region of, for example, epoxy insulation 72 in which is embedded a silver reference electrode 73, a platinum working electrode 74, and a platinum counter electrode 75. The preferred embodiments are neither limited by the composition of the electrodes nor their position within the sensor interface dome 54.

FIG. 5C depicts a cross-sectional exploded view of the electrode-membrane region set forth in FIG. 5B detailing the sensor tip and the functional membrane layers. As depicted in FIG. 5C, the electrode-membrane region comprises several different membrane layers, the compositions and functions of which are described in detail below. The top ends of the electrodes are in contact with the electrolyte phase 76, a free-flowing fluid phase. The electrolyte phase is covered by the enzyme membrane 78, also referred to as the sensing membrane, that contains an enzyme, e.g. glucose oxidase, and several functional polymer layers (as described below). In turn, a bioprotective membrane 34, and serves, in part, to protect the sensor from external forces that can result in environmental stress cracking of the enzyme membrane 48. In some embodiments, the bioprotective membrane 34 comprises a cell impermeable (second) domain such as described with reference to FIGS. 2A and 2B above. An angiogenic layer 78 is placed over the bioprotective membrane 34 and serves to promote vascularization in the sensor interface region. In some embodiments, the angiogenic layer 78 comprises a cell disruptive (first) domain such as described with reference to FIGS. 2A and 2B above.

A retaining gasket 80 composed of, for example, silicone rubber, is used to retain the sensor interface capsular attachment layer 58 (FIGS. 5A-B) and the angiogenic layer 78 and the bioprotective membrane 34 (not shown). In these embodiments, the angiogenic layer 78 and the bioprotective membrane 34 pass over the tip of the sensor interface dome 54, over the O-ring 64, and then under the sensor interface capsular attachment layer 58 and the retaining gasket 80.

The preferred embodiments contemplate the construction of the membrane layers of the sensor interface region using standard film coating techniques. This type of membrane fabrication facilitates control of membrane properties and membrane testing.

As alluded to above and disclosed in FIG. 5C, in a preferred embodiment, the sensor interface region comprises several different layers and membranes that cover the electrodes of an implantable analyte-measuring device. The characteristics of these layers and membranes are now discussed in more detail. The layers and membranes prevent direct contact of the biological fluid sample with the electrodes, while permitting selected substances (e.g. analytes) of the fluid to pass therethrough for electrochemical reaction with the electrodes.

The membranes used in the sensor interface region are semipermeable membranes. Generally speaking, the two fundamental diffusion processes by which a semipermeable membrane can limit the amount of a substance that passes therethrough are i) diffusion through the semipermeable membrane as a porous structure and ii) diffusion through the semipermeable membrane as a monolithic, homogeneous structure. The preferred embodiments are not limited by the nature of the semipermeable membranes used in the sensor interface region.

A semipermeable membrane that comprises a porous structure consists of a relatively impermeable matrix that includes a plurality of "microholes" or pores of molecular dimensions. Transfer through these membranes is primarily due to passage of substances through the pores (i.e., the membrane acts as a microporous barrier or sieve). Examples of materials that can be used to form porous, semipermeable membranes include, but are not limited to, polyethylene, polyvinylchloride, polytetrafluoroethylene, polypropylene, polyacrylamide, cellulose acetate, polymethyl methacrylate, silicone polymers, polycarbonate, and cellulosic polymers.

Because diffusion is primarily due to passage of the substance through pores, the permeability is related to the effective size of the pores, the membrane thickness, and to the molecular size of the diffusing substance. As a result, there is little selectivity in the separation of two chemically or structurally related molecules, except when their molecular size is approximately the same as the size of the pore; when this occurs, forces acting between the substance and the surface of the pore channel can influence the rate of transfer. In addition, the upper size limit to diffusion is determined by the largest pore diameter, and the overall diffusion rate depends on the total number of pores.

In contrast, passage of a substance through a monolithic, homogeneous membrane depends upon selective dissolution and diffusion of the substance as a solute through a solid, non-porous film. As used herein, the term "monolithic" means substantially non-porous and having a generally unbroken surface. The term "homogeneous", with reference to a membrane, means having substantially uniform characteristics from one side of the membrane to the other. However, a membrane may have heterogeneous structural domains, for example, created by using block copolymers (i.e., polymers in which different blocks of identical monomer units alternate with each other), and still be characterized functionally as homogeneous with respect to its dependence upon dissolution rather than sieving to effect separation of substances. A monolithic membrane can thus be used to selectively separate components of a solution on the basis of properties other than the size, shape and density of the diffusing substances. Monolithic, homogeneous membranes act as a barrier because of the preferential diffusion therethrough of some substance. They can be formed from materials such as those previously listed for porous membranes, including, but not limited to, polyethylene, polyvinylchloride, tetrafluorethylene, polypropylene, polyacrylamide, polymethyl methacrylate, silicone polymers, polycarbonate, collagen, polyurethanes and block copolymers thereof (block copolymers are discussed in U.S. Pat. Nos. 4,803,243 and 4,686,044, hereby incorporated by reference).

Angiogenic Layer

For implantable glucose monitoring devices, a sensor/tissue interface is created which provides the sensor with oxygen and glucose concentrations comparable to that normally available to tissue comprised of living cells. Absent such an interface, the sensor is associated with unstable and chaotic performance indicating that inadequate oxygen and/or glucose are reaching the sensor. The development of suitable interfaces in other contexts has been reported. For example, investigators have developed techniques that stimulate and maintain blood vessels inside a FBC to provide for the demanding oxygen needs of pancreatic islets within an implanted membrane. See, e.g. See, e.g. Brauker et al., Abstract from 4th World Biomaterials Congress, Berlin (1992). These techniques depend, in part, on the use of a vascularizing layer on the exterior of the implanted membrane. However, previously described implantable analyte-monitoring devices have not been able to successfully maintain sufficient blood flow to the sensor interface.

As described above, the outermost layer of the electrode-membrane region comprises an angiogenic material. Namely, any material that promotes angiogenesis in or around the membrane. For example, the angiogenic layer can be comprised of hydrophilic polyvinylidene fluoride (e.g. Durapore®; Millipore), mixed cellulose esters (e.g. MF; Millipore), polyvinyl chloride (e.g. PVC; Millipore), and other polymers including, but not limited to, polypropylene, polysulfone, and polymethacrylate. Preferably, the thickness of the angiogenic layer is about 10 μm to about 20 μm. In one embodiment, the angiogenic layer comprises pores sizes of about 0.5 μm to about 20 μm, and more preferably about 1.0 μm to about 10 μm, sizes that allow most substances to pass through, including, e.g. macrophages. The preferred material is expanded PTFE of a thickness of about 15 μm and pore sizes of about 5 μm to about 10 μm.

In some embodiments, the angiogenic layer comprises a cell disruptive (first) domain such as described with reference to FIGS. 2A and 2B, above. For example, the angiogenic layer can comprise a bioactive agent, such as a vascularization agent, which promotes vascularization in or around the membrane.

To further promote stable foreign body capsule structure without interfering with angiogenesis, an additional outermost layer of material comprised of a thin low-density non-woven polyester (e.g. manufactured by Gore) can be laminated over the preferred PTFE described above. In preferred embodiments, the thickness of this layer is about 120 μm. This additional thin layer of material does not interfere with angiogenesis and enhances the manufacturability of the angiogenic layer. See, e.g. See U.S. Pat. No. 5,453,278 to Brauker et al., hereby incorporated by reference; PCT Patent Publication Nos. 96/32076, 96/01611, and 92/07525 assigned to Baxter.

Bioprotective Membrane

The inflammatory response that initiates and sustains a FBC is associated with both advantages and disadvantages. Some inflammatory response is needed to create a new capillary bed in close proximity to the surface of the sensor in order to i) continuously deliver adequate oxygen and glucose and ii) create sufficient tissue ingrowth to anchor the implant and prevent motion artifact. On the other hand, inflammation is associated with invasion of tissue macrophages that have the ability to biodegrade many artificial biomaterials (some of which were, until recently, considered nonbiodegradable). When activated by a foreign body, tissue macrophages degranulate, releasing from their cytoplasmic myeloperoxidase system hypochlorite (bleach), $H_2O_2$ and other oxidant species. Both hypochlorite and $H_2O_2$ are known to break down a variety of polymers, including polyurethane, by a phenomenon referred to as environmental stress cracking. See, e.g. Phillips et al., J. Biomat. Appl., 3:202-227 (1988); Stokes, J. Biomat. Appl. 3:228-259 (1988). Indeed, environmental stress cracking has been shown to limit the lifetime and performance of an enzyme-active polyurethane membrane stretched over the tip of a glucose sensor. See, e.g. Updike et al., Am. Soc. Artificial Internal Organs, 40:157-163 (1994).

Because both hypochlorite and $H_2O_2$ are short-lived chemical species in vivo, biodegradation will not occur if macrophages are kept a sufficient distance from the enzyme active membrane. This preferred embodiment contemplates the use of protective biomaterials (for example, a cell impermeable domain) of a few microns thickness or more that are permeable to oxygen and glucose and are placed over the tip of the sensor to keep the macrophages from gaining proximity to the enzyme (sensing) membrane. The bioprotective layer should be biostable for long periods of time (e.g. several years); the preferred embodiments contemplate the use of polymers including, but not limited to, polypropylene, polysulfone, polytetrafluoroethylene (PTFE), and poly(ethylene terephthalate) (PET). Preferably, the bioprotective layer is constructed of expanded PTFE with a pore size of about 0.2 μm to about 0.5 μm and a thickness of about 15 μm to about 35 μm. Most preferably, the bioprotective layer is constructed of expanded PTFE with a pore size of 0.4 μm and a thickness of approximately 25 μm (e.g. Millicell CM-Biopore®; Millipore).

In some embodiments, the bioprotective layer comprises materials and methods such as described above with reference to the cell impermeable (second) domain with reference to FIGS. 2A and 2B above, however the preferred embodiments are not limited by the nature of the bioprotective layer. In some embodiments, a bioactive agent is incorporated into at least one of the angiogenic layer and bioprotective membrane 78, 34, or into the sensor interface dome and adapted to diffuse through the membrane layers, in order to modify the tissue response of the host to the membrane.

The Enzyme Membrane

The preferred embodiments contemplate membranes impregnated with enzyme. It is not intended that the preferred embodiments be limited by the nature of the enzyme membrane. The enzyme membrane of a preferred embodiment is depicted in FIG. 5C as being a single, homogeneous structure. However, in preferred embodiments, the enzyme membrane comprises a plurality of distinct layers such as described above with reference to FIGS. 4A and 4b and in the following description. In one preferred embodiment, the enzyme membrane comprises the following four layers (in succession from the bioprotective membrane to the electrolyte phase): i) a resistance layer; ii) an enzyme layer; iii) an interference layer; and iv) an electrolyte layer.

Resistance Layer

There is a molar excess of glucose relative to the amount of oxygen in samples of blood. Indeed, for every free oxygen molecule in extracellular fluid, there are typically more than 100 glucose molecules present. See, e.g. Updike et al., Diabetes Care 5:207-21 (1982). However, an immobilized enzyme-based sensor using oxygen ($O_2$) as cofactor is supplied with oxygen in non-rate-limiting excess in order to respond linearly to changes in glucose concentration while not responding to changes in oxygen tension. More specifically, when a glucose-monitoring reaction is oxygen-limited, linearity is not achieved above minimal concentrations of glucose. Without a semipermeable membrane over the enzyme layer, linear response to glucose levels can be obtained only up to about 40 mg/dL; however, in a clinical setting, linear response to glucose levels are desirable up to at least about 500 mg/dL.

The resistance layer comprises a semipermeable membrane that controls the flux of oxygen and glucose to the underlying enzyme layer (i.e., limits the flux of glucose), rendering a supply of oxygen in non-rate-limiting excess. As a result, the upper limit of linearity of glucose measurement is extended to a much higher value than that which could be achieved without the resistance layer. The devices of the preferred embodiments contemplate resistance layers comprising polymer membranes with oxygen-to-glucose permeability ratios of approximately 200:1; as a result, one-dimensional reactant diffusion is adequate to provide excess oxygen at all reasonable glucose and oxygen concentrations found in the subcutaneous matrix [Rhodes et al., Anal. Chem., 66:1520-1529 (1994).

In preferred embodiments, the resistance layer has a thickness of less than about 45 μm, more preferably in the range of about 15 μm to about 40 μm and most preferably in the range of about 20 μm to about 35 μm.

Enzyme Layer

In addition to glucose oxidase, the preferred embodiments contemplate the use of a membrane layer impregnated with other oxidases, e.g. galactose oxidase, uricase. For an enzyme-based electrochemical glucose sensor to perform well, the sensor's response is not limited by enzyme activity or cofactor concentration. Because enzymes, including the very robust glucose oxidase, are subject to deactivation as a function of ambient conditions, this behavior needs to be accounted for in constructing sensors for long-term use.

The principle of losing half of the original enzyme activity in a specific time can be used in calculating how much enzyme needs to be included in the enzyme layer to provide a sensor of required lifetime (see Experimental section). Previously, researchers have found that, when placed in a saline solution at 37° C., glucose electrodes lose half of their electrode enzyme activity in 85 to 105 days. See, e.g. Tse and Gough, Biotechnol. Bioeng. 29:705-713 (1987). Under reasonable diabetic conditions and normal enzyme loading (e.g., 2.times.10.sup.-4 M glucose oxidase; see Example 4), useful sensor lifetimes can last for at least one year. However, exposure of the sensor to high levels of glucose in combination with low oxygen levels for prolonged periods can result in shortened sensor lifetimes. See, e.g. Rhodes et al., Anal. Chem., 66:1520-1529 (1994).

Excess glucose oxidase loading is required for long sensor life. The Experimental section provides a procedure that can be used to determine the appropriate amount of enzyme to be included in the enzyme layer. When excess glucose oxidase is used, up to two years of performance is possible from the glucose-monitoring devices contemplated by the preferred embodiments.

Interference Layer

The interference layer comprises a thin, hydrophobic membrane that is nonswellable and has a low molecular weight cut-off. The interference layer is permeable to relatively low molecular weight substances, such as hydrogen peroxide, but restricts the passage of higher molecular weight substances, including glucose and ascorbic acid. The interference layer serves to allow analytes and other substances that are to be measured by the electrodes to pass through, while preventing passage of other substances.

The interference layer has a preferred thickness of less than about 5 μm, more preferably in the range of about 0.1 μm to about 5 μm and most preferably in the range of about 0.5 μm to about 3 μm.

Electrolyte Layer

To ensure electrochemical reaction, the electrolyte layer comprises a semipermeable coating that maintains hydrophilicity at the electrode region of the sensor interface. The electrolyte layer enhances the stability of the interference layer of the preferred embodiments by protecting and supporting the membrane that makes up the interference layer. Furthermore, the electrolyte layer assists in stabilizing operation of the device by overcoming electrode start-up problems and drifting problems caused by inadequate electrolyte. The buffered electrolyte solution contained in the electrolyte layer also protects against pH-mediated damage that can result from the formation of a large pH gradient between the hydrophobic interference layer and the electrode (or electrodes) due to the electrochemical activity of the electrode.

Preferably the coating comprises a flexible, water-swellable, substantially solid gel-like film having a "dry film" thickness of about 2.5 µm to about 12.5 µm, preferably about 6.0 µm. "Dry film" thickness refers to the thickness of a cured film cast from a coating formulation onto the surface of the membrane by standard coating techniques. The coating formulation comprises a premix of film-forming polymers and a crosslinking agent and is curable upon the application of moderate heat.

Suitable coatings are formed of a curable copolymer of a urethane polymer and a hydrophilic film-forming polymer. Particularly preferred coatings are formed of a polyurethane polymer having anionic carboxylate functional groups and non-ionic hydrophilic polyether segments, which is crosslinked in the present of polyvinylpyrrolidone and cured at a moderate temperature of about 50° C.

Particularly suitable for this purpose are aqueous dispersions of fully reacted colloidal polyurethane polymers having cross-linkable carboxyl functionality (e.g. BAYBOND®; Mobay Corporation). These polymers are supplied in dispersion grades having a polycarbonate-polyurethane backbone containing carboxylate groups identified as XW-121 and XW-123; and a polyester-polyurethane backbone containing carboxylate groups, identified as XW-110-2. Particularly preferred is BAYBOND® 123, an aqueous anionic dispersion of an aliphatic polycarbonate urethane polymer sold as a 35 weight percent solution in water and co-solvent N-methyl-2-pyrrolidone.

Polyvinylpyrrolidone is also particularly preferred as a hydrophilic water-soluble polymer and is available commercially in a range of viscosity grades and average molecular weights ranging from about 18,000 to about 500,000, under the PVP K® homopolymer series by BASF Wyandotte and by GAF Corporation. Particularly preferred is the homopolymer having an average molecular weight of about 360,000 identified as PVP-K90 (BASF Wyandotte). Also suitable are hydrophilic, film-forming copolymers of N-vinylpyrrolidone, such as a copolymer of N-vinylpyrrolidone and vinyl acetate, a copolymer of N-vinylpyrrolidone, ethylmethacrylate and methacrylic acid monomers, and the like.

The polyurethane polymer is crosslinked in the presence of the polyvinylpyrrolidone by preparing a premix of the polymers and adding a cross-linking agent just prior to the production of the membrane. Suitable cross-linking agents can be carbodiimides, epoxides and melamine/formaldehyde resins. Carbodiimide is preferred, and a preferred carbodiimide crosslinker is UCARLNK® XL-25 (Union Carbide).

The flexibility and hardness of the coating can be varied as desired by varying the dry weight solids of the components in the coating formulation. The term "dry weight solids" refers to the dry weight percent based on the total coating composition after the time the crosslinker is included. A preferred useful coating formulation can contain about 6 to about 20 dry weight percent, preferably about 8 dry weight percent, polyvinylpyrrolidone; about 3 to about 10 dry weight percent preferably about 5 dry weight percent cross-linking agent; and about 70 to about 91 weight percent, preferably about 87 weight percent of a polyurethane polymer, preferably a polycarbonate-polyurethane polymer. The reaction product of such a coating formulation is referred to herein as a water-swellable cross-linked matrix of polyurethane and polyvinylpyrrolidone.

The Electrolyte Phase

The electrolyte phase is a free-fluid phase comprising a solution containing at least one compound, usually a soluble chloride salt, which conducts electric current. The electrolyte phase flows over the electrodes (see FIG. 5C) and is in contact with the electrolyte layer of the enzyme membrane. The devices of the preferred embodiments contemplate the use of any suitable electrolyte solution, including standard, commercially available solutions.

Generally speaking, the electrolyte phase should have the same or less osmotic pressure than the sample being analyzed. In preferred embodiments, the electrolyte phase comprises normal saline.

Electrode

The electrode assembly of the preferred embodiments can also be used in the manner commonly employed in the making of amperometric measurements. A sample of the fluid being analyzed is placed in contact with a reference electrode, e.g. silver/silver-chloride, and the electrode of the preferred embodiments, which is preferably formed of platinum. The electrodes are connected to a galvanometer or polarographic instrument and the current is read or recorded upon application of the desired D.C. bias voltage between the electrodes.

The ability of the present device electrode assembly to accurately measure the concentration of substances such as glucose over a broad range of concentrations in fluids including undiluted whole blood samples enables the rapid and accurate determination of the concentration of those substances. That information can be employed in the study and control of metabolic disorders including diabetes.

Sensor Implantation and Radiotelemetric Output

Long-term sensor performance is best achieved, and transcutaneous bacterial infection is eliminated, with implanted devices capable of radiotelemetric output. The preferred embodiments contemplate the use of radio telemetry to provide data regarding blood glucose levels, trends, and the like. The term "radio telemetry" refers to the transmission by radio waves of the data recorded by the implanted device to an ex vivo recording station (e.g. a computer), where the data is recorded and, if desired, further processed.

Although totally implanted glucose sensors of three month lifetime, with radiotelemetric output, have been tested in animal models at intravenous sites (See, e.g. Armour et al., Diabetes, 39:1519-1526 (1990)), subcutaneous implantation is the preferred mode of implantation. See, e.g. Gilligan et al., Diabetes Care 17:882-887 (1994). The subcutaneous site has the advantage of lowering the risk for thrombophlebitis with hematogenous spread of infection and also lowers the risk of venous thrombosis with pulmonary embolism. In addition, subcutaneous placement is technically easier and more cost-effective than intravenous placement, as a non-surgeon health care provider in an outpatient setting can perform it under local anesthesia.

Preferably, the radio telemetry devices contemplated for use in conjunction with the preferred embodiments possess features including small package size, adequate battery life, acceptable noise-free transmission range, freedom from electrical interference, and easy data collection and processing. Radio telemetry provides several advantages, one of which is the ability of an implanted device to measure analyte levels in a sealed-off, sterile environment.

The preferred embodiments are not limited by the nature of the radio telemetry equipment or methods for its use. Indeed, commercially available equipment can be modified for use with the devices of the preferred embodiments (e.g. devices manufactured by Data Sciences). Similarly, custom-designed radiotelemetry devices like those reported in the literature can be used in conjunction with the implantable analyte-measuring devices of the preferred embodiments. See, e.g. McKean and Gough, IEEE Trans. Biomed. Eng. 35:526-532 (1988); Shichiri et al., Diabetes Care 9:298-301 (1986); and Shults et al., IEEE Trans. Biomed. Eng. 41:937-942 (1994). In a preferred embodiment, transmitters are programmed with an external magnet to transmit at 4-, 32-, or 256-second intervals depending on the need of the subject; presently, battery lifetimes at the current longest transmission intervals (about 256 seconds) is approximately up to two years.

Response Time and Calibration

Every measurement method reports data with some delay after the measured event. For data to be useful, this delay is smaller than some time depending on the needs of the method. Thus, response time of the devices of preferred embodiments has been carefully studied. The use of the term "initial response" is not to be confused with the term "response time." After a step function change in glucose concentration, the time delay before the first unequivocal change in sensor signal occurs is the "initial response," while the following time delay to reach 90% of the steady-state signal development is the "response time." "Response time" is the factor which normally controls how quickly a sensor can track a dynamically changing system.

Furthermore, the time required before a glucose sensor in a FBC will indicate an initial response to a bolus intravenous glucose injection is a function of the animal "circulation time" and the sensor's "initial response". The circulation time is the time required for a bolus glucose injection to reach the site of sensor implantation.

Generally speaking, equilibration between vascular and interstitial compartments for glucose is so rapid that it plays no role in either the initial response or the observed response time. If the tip of the sensor is in intimate contact with the interstitial compartment (e.g., FBC), then there is no significant delay in glucose diffusing from the capillary lumen to the tip of the sensor. The inventors have found that the glucose sensors of the preferred embodiments provide initial responses of about 30 seconds in dogs about half of which is circulation time. The dog model represents a useful and accepted model for determining the efficacy of glucose monitoring devices.

While the devices of the preferred embodiments do not require a specific response time, in preferred embodiments, the in vitro 90% response times at 37° C. for subsequently subcutaneously implanted devices are in the range of 2 to 5 minutes in dogs. Though the use of the devices of the preferred embodiments does not require an understanding of the factors that influence response time or the factors' mechanisms of action, in vivo response times are believed to be primarily a function of glucose diffusion through the sensor membrane (e.g. a 40-60 micron membrane). Of note, response times of up to about 10 minutes do not limit the clinical utility of tracking blood glucose in diabetic patients because physiologic or pathologic glucose levels do not change more rapidly than a few percent per minute.

In calibrating the glucose sensors of the preferred embodiments, a single point recalibration of the sensor at four-week intervals against an acceptable glucose reference method is preferred (e.g. calibration against blood obtained from a finger-prick). Generally speaking, the recalibration amounts to a simple adjustment in sensor gain. The sensor offset current (i.e., the current at 0 mg/dL glucose) needs to remain invariant over the duration of the implant for the sensor to provide optimal data.

EXPERIMENTS

The following examples serve to illustrate certain preferred embodiments and aspects and are not to be construed as limiting the scope thereof.

In the preceding description and the experimental disclosure which follows, the following abbreviations apply: Eq and Eqs (equivalents); mEq (milliequivalents); M (molar); mM (millimolar) µM (micromolar); N (Normal); mol (moles); mmol (millimoles); µmol (micromoles); nmol (nanomoles); g (grams); mg (milligrams); µg (micrograms); Kg (kilograms); L (liters); mL (milliliters); dL (deciliters); µL (microliters); cm (centimeters); mm (millimeters); µm (micrometers); nm (nanometers); h and hr (hours); min. (minutes); s and sec. (seconds); ° C. (degrees Centigrade).

Example 1

The polyurethanes are preferably prepared as block copolymers by solution polymerization techniques as generally described in Lyman, J. Polymer Sci. 45:49 (1960). Specifically, a two-step solution polymerization technique is used in which the poly(oxyethylene) glycol is first "capped" by reaction with a diisocyanate to form a macrodiisocyanate. The macrodiisocyanate is then coupled with a diol (or diamine) and the diisocyanate to form a block copolyetherurethane (or a block copolyurethaneurea). The resulting block copolymers are tough and elastic and can be solution-cast in N,N-dimethylformamide to yield clear films that demonstrate good wet strength when swollen in water.

In particular, a mixture of 8.4 g (0.006 mol), poly(oxyethylene) glycol (CARBOWAX® 1540, Union Carbide), and 3.0 g (0.012 mol) 4,4'-diphenylmethane diisocyanate in 20 mL dimethyl sulfoxide/4-methyl-2-pentanone (50/50) is placed in a three-necked flask equipped with a stirrer and condenser and protected from moisture. The reaction mixture is stirred and heated at 110° C. for about one hour. To this clear solution is added 1.5 g (0.014 mol) 1,5-pentanediol and 2.0 g (0.008 mol) 4,4'-diphenylmethane diisocyanate.

After heating at 110° C. for an additional two hours, the resulting viscous solution is poured into water. The tough, rubbery, white polymer precipitate that forms is chopped in a Waring Blender, washed with water and dried in a vacuum oven at about 60° C. The yield is essentially quantitative. The inherent viscosity of the copolymer in N,N-dimethyl formamide is 0.59 at 30° C. (at a concentration of about 0.05 percent by weight).

Example 2

As previously described, the electrolyte layer, the membrane layer closest to the electrode, can be coated as a water-swellable film. This example illustrates a coating comprising a polyurethane having anionic carboxylate functional groups and hydrophilic polyether groups and polyvinylpyrrolidone (PVP) that can be cross-linked by carbodiimide.

A coating preparation is prepared comprising a premix of a colloidal aqueous dispersion of particles of a urethane polymer having a polycarbonate-polyurethane (PC-PU) backbone containing carboxylate groups and the water-soluble hydrophilic polymer, PVP, which is crosslinked by the addition of the cross-linking agent just before production of the coated membrane. Example coating formulations are illustrated in Table 1.

TABLE 1

|  | A | | B | | C | |
|---|---|---|---|---|---|---|
|  | Weight | Dry Weight % Solids | Weight | Dry Weight % Solids | Weight | Dry Weight % Solids |
| Premix | | | | | | |
| PVP[1] | 48 | 6 | 64 | 8 | 160 | 20 |
| PC-PV[2] | 260 | 91 | 248 | 87 | 200 | 70 |
| Cross-Linking Agent | | | | | | |
| Carbodiimide[3] | 6 | 3 | 10 | 5 | 20 | 10 |
| Totals | 314 | 100 | 322 | 100 | 380 | 100 |

[1]Aqueous solution containing 12.5 weight percent PVP prepared from polyvinylpyrrolidone having a number average molecular weight of about 360,000 sold as a powder under the trademark BASF K90 by BASF Wyandotte Corporation.
[2]Colloidal dispersion of a polycarbonatepolyurethane (PCPU) polymer at about 35 weight percent solids in a cosolvent mixture of about 53 weight percent water and about 12 weight percent Nmethyl-2-pyrrolidone (BAYBOND ® 123 or XW123; Mobay Corporation). As supplied, the dispersion has a pH of about 7.5-9.0.
[3]Carbodiimide (UCARLNK ® XL25SE, Union Carbide Corporation supplied at about 50 weight percent solids in a solvent solution of propylene glycol monomethylether acetate.

The viscosity and pH of the premix can be controlled and maintained during processing and to prolong its useful life by adding water or adjusting the pH with dilute ammonia solution or an equivalent base prior to adding the crosslinker.

For production, the coating is applied with a Mayer rod onto the unbound surface of a multilayered membrane. The amount of coating applied should cast a film having a "dry film" thickness of about 2.5 µm to about 12.5 µm, preferably about 6.0 µm. The coating is dried above room temperature preferably at about 50° C. This coating dries to a substantially solid gel-like film that is water swellable to maintain electrolyte between the membrane covering the electrode and the electrode in the electrode assembly during use.

Example 3

The following procedure was used to determine the amount of enzyme to be included in the enzyme layer. It is to be understood that the preferred embodiments are not limited to the use of this or a similar procedure, but rather contemplates the use of other techniques known in the art.

A starting glucose oxidase concentration of $2 \times 10^{-4}$ M was calculated from the enzyme weight and the final volume of the enzyme layer. Thereafter, a series of eight additional membrane formulations was prepared by decrementing enzyme concentration in 50% steps (referred to as a change of one "half loading") down to 7.8-7 M. Sensor responses were then collected for this range of enzyme loadings and compared to computer-simulated sensor outputs. The simulation parameter set used included previously determined membrane permeabilities and the literature mechanisms and kinetics for glucose oxidase. See, e.g. Rhodes et al., Anal. Chem., 66:1520-1529 (1994).

There was a good match of real-to-simulated sensor output at all loadings (data not shown). Approximately a six-to-seven "half loading" drop in enzyme activity was required before the sensor output dropped 10%; another two-to-three half loading drop in enzyme activity was required to drop the sensor response to 50% of the fully loaded sensor response. These results indicate that, at the loading used and the decay rates measured, up to two years of performance is possible from these sensors when the sensor does not see extended periods of high glucose and physiologically low $O_2$ concentrations.

Example 4

This example illustrates long-term glucose sensor device response following subcutaneous implantation of sensor devices contemplated by the preferred embodiments into a dog. The stages of FBC development are indicated by the long term glucose sensor device response.

Figure 6:
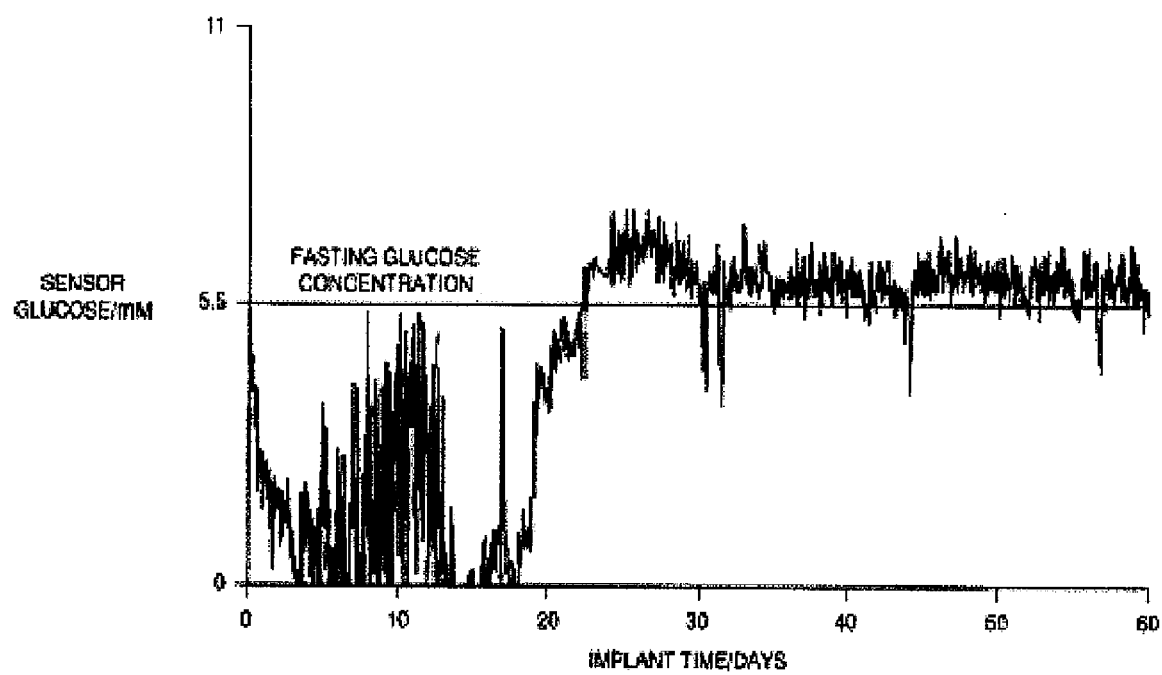
FIG. 6 graphically depicts glucose levels as a function of the number of days post-implant.

FIG. 6 graphically depicts glucose levels as a function of the number of days post-implant. The data in FIG. 6 was taken at four-minute intervals for 60 days after implantation. Sensor response is calculated from a single preimplant calibration at 37° C. Normal canine fasting glucose concentration of 5.5 mM is shown for comparison.

The data set forth in FIG. 6 can be used to illustrate the four typically identifiable phases in FBC formation. Phase 1 shows rapidly dropping response from the time of implant to, in this case, day 3. Though an understanding of the mechanism for this drop in sensor output is not required in order to practice the preferred embodiments, it is believed to reflect low $pO_2$ and low glucose present in fluid contacting the sensor. Phase 2 shows intermittent sensor-tissue contact in seroma fluid from, in this case, day 3 to about day 13. During this phase, fragile new tissue and blood supply intermittently make contact with the sensor (which is surrounded by seroma fluid). Phase 3 shows stabilization of capillary supply between, in this case, days 13 and 22. More specifically, the noise disappears and sensor output rises over approximately six days to a long-term level associated with tracking of FBC glucose. Again, though an understanding of this effect is not required to practice the preferred embodiments, the effect is believed to reflect consistent contact of FBC tissue with the sensor surface. Phase 4 from, in this case, day 22 to day 60, shows duration of useful sensor device life. While there are timing variations of the stages from sensor device to sensor device, generally speaking, the first three steps of this process take from 3 days to three weeks and continuous sensing has been observed for periods thereafter (e.g. for periods of 150 days and beyond).

Example 5

In addition to collecting normoglycemic or non-diabetic dog data from the sensor of the preferred embodiments as shown in Example 4, calibration stability, dynamic range, freedom from oxygen dependence, response time and linearity of the sensor can be studied by artificial manipulation of the intravenous glucose of the sensor host.

Figure 7:
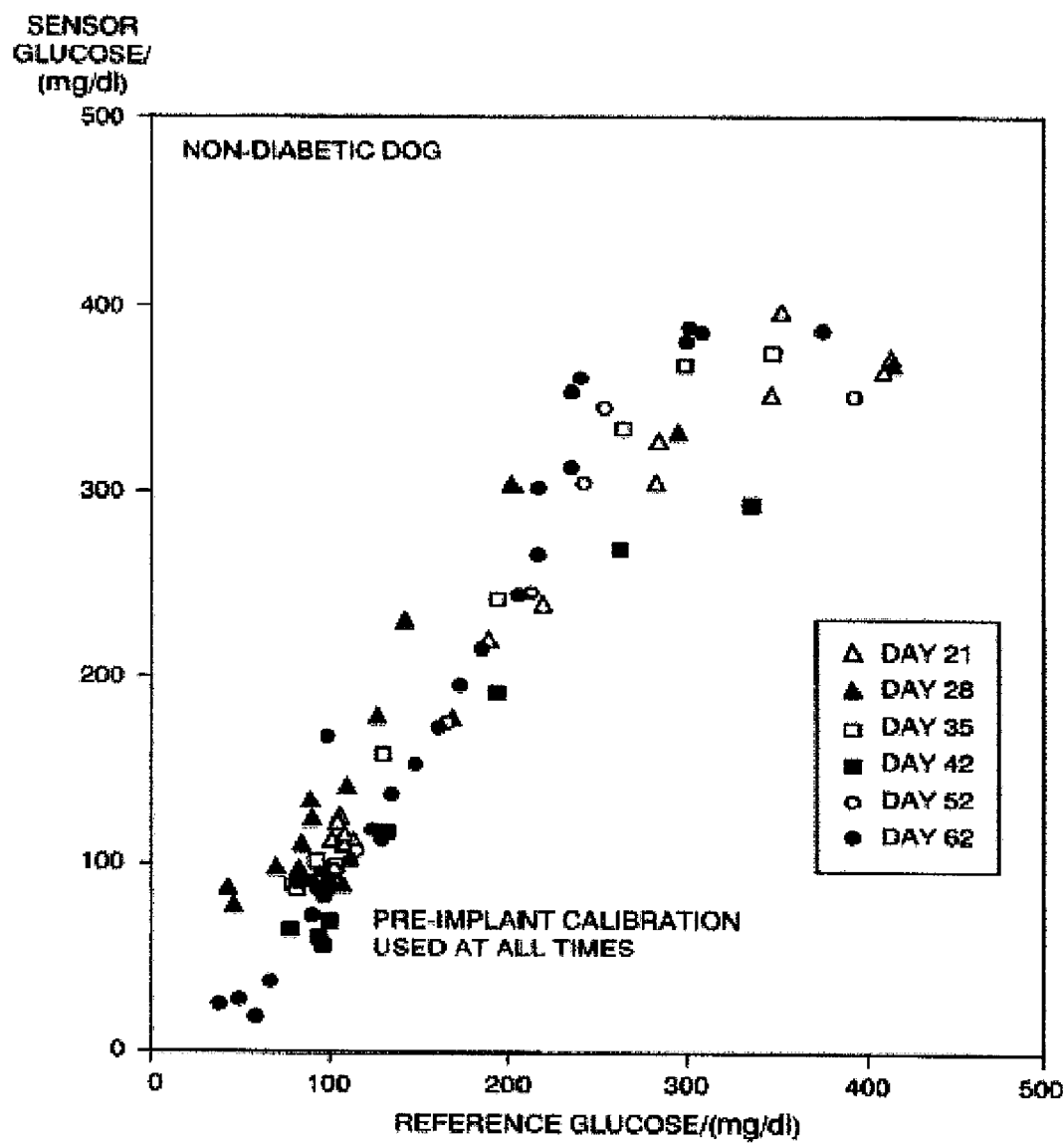
FIG. 7 graphically depicts a correlation plot (days 21 to 62) of a glucose infusion study with one device of a preferred embodiment.

This was done in this example via infusion of a 15 g bolus of 50% sterile Dextrose given intravenously in less than about 20 seconds. Reference blood glucose data was then taken from a different vein at 2-5 minute intervals for up to 2 hours after bolus infusion. FIG. 7 depicts correlation plots of six bolus infusion studies, at intervals of 7-10 days on one sensor of the preferred embodiments. Sensor glucose concentrations are calculated using a single 37° C. in vitro preimplantation calibration. The sensor response time is accounted for in calculating the sensor glucose concentrations at times of reference blood sampling by time shifting the sensor data 4 minutes.

As with any analytical system, periodic calibration should be performed with the devices of the preferred embodiments. Thus, the preferred embodiments contemplate some interval of calibration and/or control testing to meet analytical, clinical and regulatory requirements.

Example 6

This example describes experiments directed at sensor accuracy and long-term glucose sensor response of several sensor devices contemplated by the preferred embodiments.

Pre-Implant In Vitro Evaluation

Figure 8:
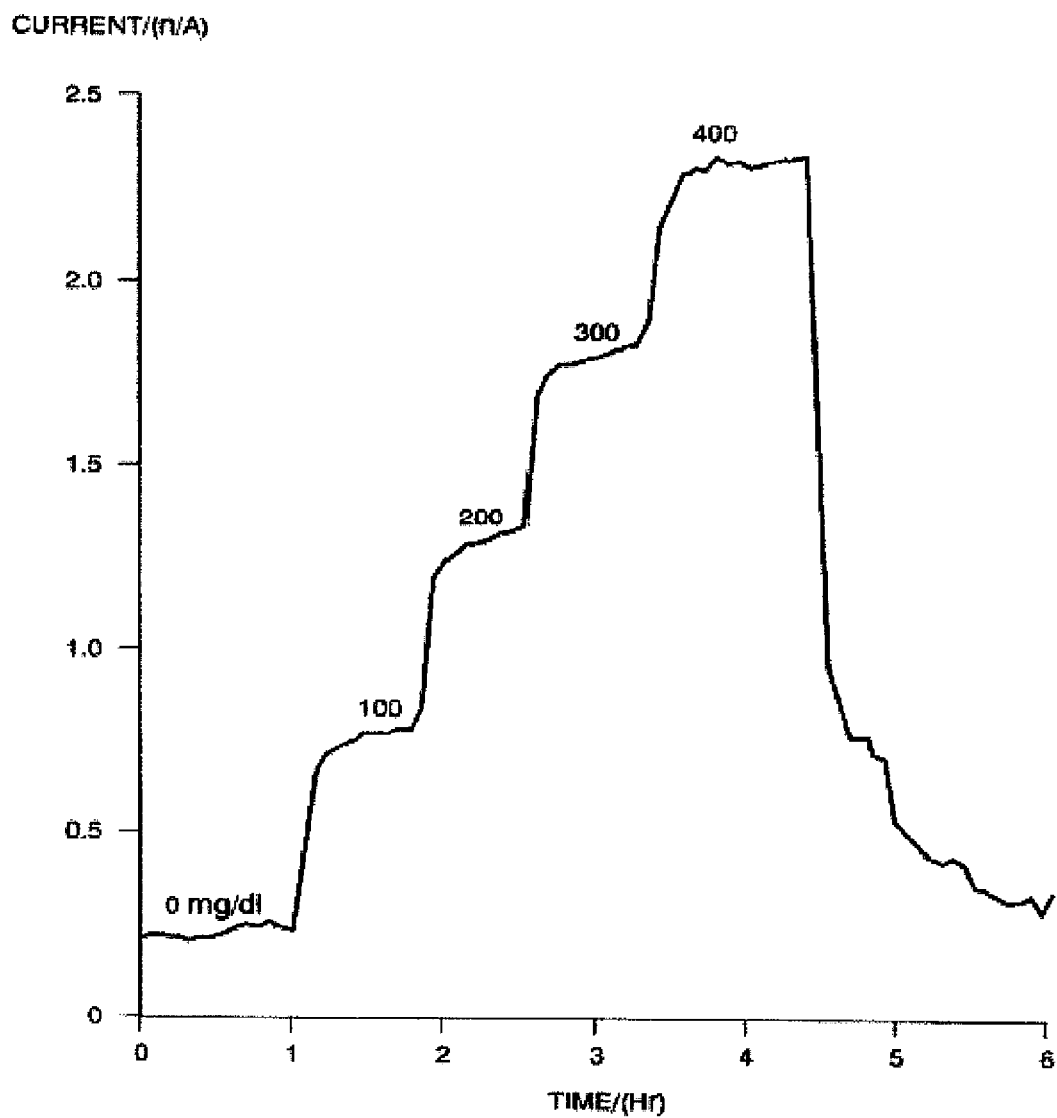
FIG. 8 depicts a typical response to in vitro calibration to glucose of a device of a preferred embodiment.

In vitro testing of the sensor devices was accomplished in a manner similar to that previously described. See, e.g. Gilligan et al., Diabetes Care 17:882-887 (1994). Briefly, sensor performance was verified by demonstrating linearity to 100 mg/dL glucose concentration steps from 0 mg/dL through 400 mg/dL (22 mM) with a 90% time response to the glucose steps of less than 5 minutes. A typical satisfactory response to this protocol is shown in FIG. 8. Modulating dissolved oxygen concentration from a $pO_2$ of 150 down to 30 mm Hg (0.25 to 0.05 mM) showed no more than a 10% drop in sensor output at 400 mg/dL for the preferred sensor devices of the preferred embodiments. Stability of calibration was maintained within 10% for one week before the final bioprotective and angiogenesis membranes were added to finalize the implant package. A final calibration check was made and had to be within 20% of the prior results for the sensor to be passed on to the implant stage. These final calibration factors (linear least squares regression for the zero glucose current and output to 100 mg/dL current) are used for the initial in vivo calibration. Sensor devices were then wet sterilized with 0.05% thimerosal for 24 hours just prior to implantation.

In Vivo Testing

Six sensor devices meeting the parameters described above were surgically implanted under general anesthesia (pentothal induction to effect, followed by halothane maintenance) into the paravertebral subcutaneous tissue of the same mongrel non-diabetic dog. A two-inch skin incision was made several inches from the spine for each implant allowing the creation of a tight-fitting subcutaneous pouch by blunt dissection. The implant was then inserted into the pouch in sensor-down configuration. Subcutaneous tissue was then closed with 3-0 vicryl and skin with 2-0 nylon. Animals were closely monitored for discomfort after surgery and analgesics administered as necessary.

These sensor devices were implanted two-at-a-time in the same dog at approximately six week intervals. Four of the sensor devices were covered with a PTFE-comprising angiogenic layer (these sensor devices were designated Sensors 1901, 1902, 1903, and 1905), while two of the sensor devices served as control sensor devices and did not contain an angiogenic layer, i.e., they contained a bioprotective membrane and the underlying sensor interface structures, as previously described (these sensor devices were designated Sensors 1904 and 1906). To insure anchoring of the device into the subcutaneous tissue, the sensor-side of each implant, except for just over the tip of the sensor, was jacketed in surgical grade double velour polyester fabric (Meadox Medical, Inc.). All sensor devices were tracked after implantation at four-minute intervals using radiotelemetry to follow the long-term sensor response to normoglycemia, allowing verification of the long-term stability of the sensors. To screen for sensor response to changing glucose on selected days following implantation, the response to 0.5 mg glucagon administered subcutaneously was assessed. Responding sensors were identified by a characteristically stable signal prior to glucagon administration followed by a substantial increase in signal within 20 minutes of glucagon injection. The sensor transients then reversed and returned to the prior signal levels within one hour after glucagon injection.

To determine in vivo sensor response times, short-term stability, linearity to glucose concentration, and possible oxygen cofactor limitation effects, glucose infusion studies of up to five hours duration were performed on the dog. These studies were run approximately once every three weeks. The dog was pretrained to rest comfortably and was fully alert during this testing. These experiments used the somatostatin analog octreotide (SANDOSTATIN®, Sandoz) to inhibit the release of insulin, allowing for a slow ramping of blood glucose to the 400-500 mg/dL concentration range.

Sensors were monitored at 32-second intervals to allow simultaneous tracking of up to six sensor devices. In this protocol, octreotide was injected (36-50 µg/kg) 15-20 minutes before initiation of the glucose infusion. Two peripheral veins were cannulated in the dog to allow for glucose infusion and blood glucose sampling. Ten percent dextrose (0.55 mM) was continuously infused at gradually increasing rates to provide smooth increases in blood glucose from the approximate fasting glucose concentration of about 100 mg/dL to greater than 400 mg/dL. This infusion protocol provides sensor glucose concentration data which can be correlated with reference plasma glucose values when blood samples were drawn from the animal every 5 to 10 minutes. The primary reference glucose determinations were made using a hexokinase method on the DuPont Dimension AR®. A DIRECT 30/30® meter (Markwell Medical) was also used during the course of the experiment to serve as a secondary monitor for the reference blood glucose values and estimate when 400 mg/dL had been reached. At this point the glucose infusion pump was turned off and the blood glucose allowed to return to its normal level.

An additional variation of the protocol described above involved studying the effects of insulin administration on blood glucose concentration prior to the octreotide injection. For these studies 5 units of insulin were injected intravenously, the blood glucose tracked down to 40 mg/dl with the DIRECT 30/30®, the octreotide injection made as before, and the infusion pump then started. While the initial glucose pump rate was the same, it was increased faster than before to counteract the insulin and to maintain the same experimental timing.

Once studies were completed, the data was initially analyzed using the final in vitro sensor calibration factors to calculate the implanted sensor glucose concentration. If changes were needed in these factors to optimize the linear regression of sensor to reference blood glucose they were made and noted and followed over the lifetime of the sensor device.

At varying points in time, the implanted sensor devices became less than optimal and were then explanted to determine the underlying cause (less than optimal was defined as the inability to accurately track glucose infusion during two successive tests). Explantation surgical protocols were very similar to those used in the implantation procedure except that the foreign body capsule was opened around the perimeter of the oval implant. The back and sides of the housing had no tissue attachment (as they were not covered with polyester velour), and thus easily separated from the surrounding tissue. The top of the sensor device with attached capsule was then carefully cut free from the subcutaneous tissues.

Once explanted, the sensor devices were carefully examined under a dissecting microscope to look at the state of the capsule tissue contacting the sensor membranes. Once this had been characterized and documented, the tissue was carefully removed from the membrane surface and saved for histological examination. If sensor visualization demonstrated intact membrane layers an initial in vitro calibration check was performed. The sensors were then disassembled from the top membrane down (i.e., from the membrane furthest from the electrodes) with a glucose and hydrogen peroxide calibration check made after removal of each layer. This allowed differentiation of the mechanisms leading to less than optimal results in the membranes and determination of whether processes such as environmental stress cracking, biofouling, or loss of enzyme activity were occurring.

Figure 9A:
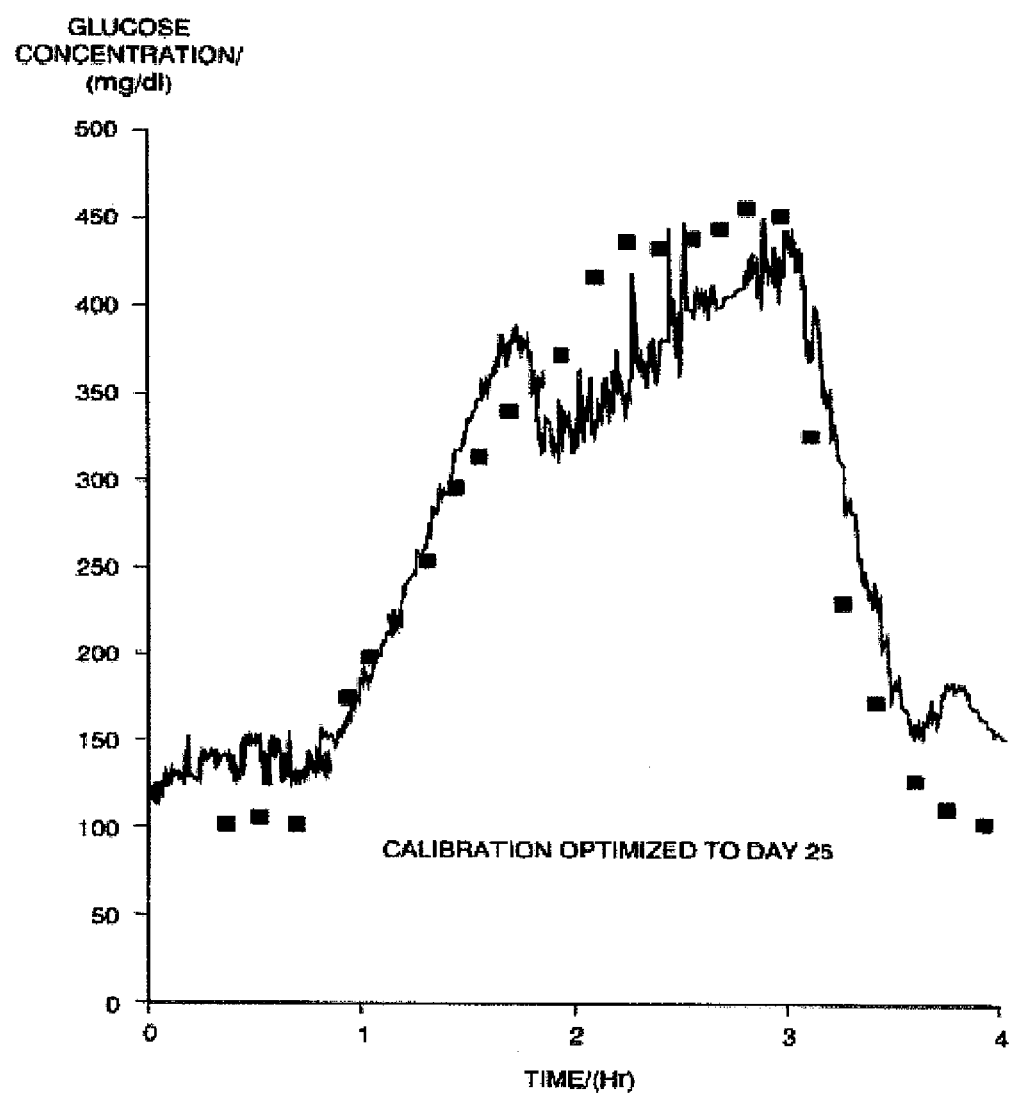
FIGS. 9A, 9B, and 9C graphically depict three in vivo sensor response curves plotted in conjunction with the reference blood glucose values for one device of a preferred embodiment at post-implant times of 25, 88, and 109 days.
Figure 9B:
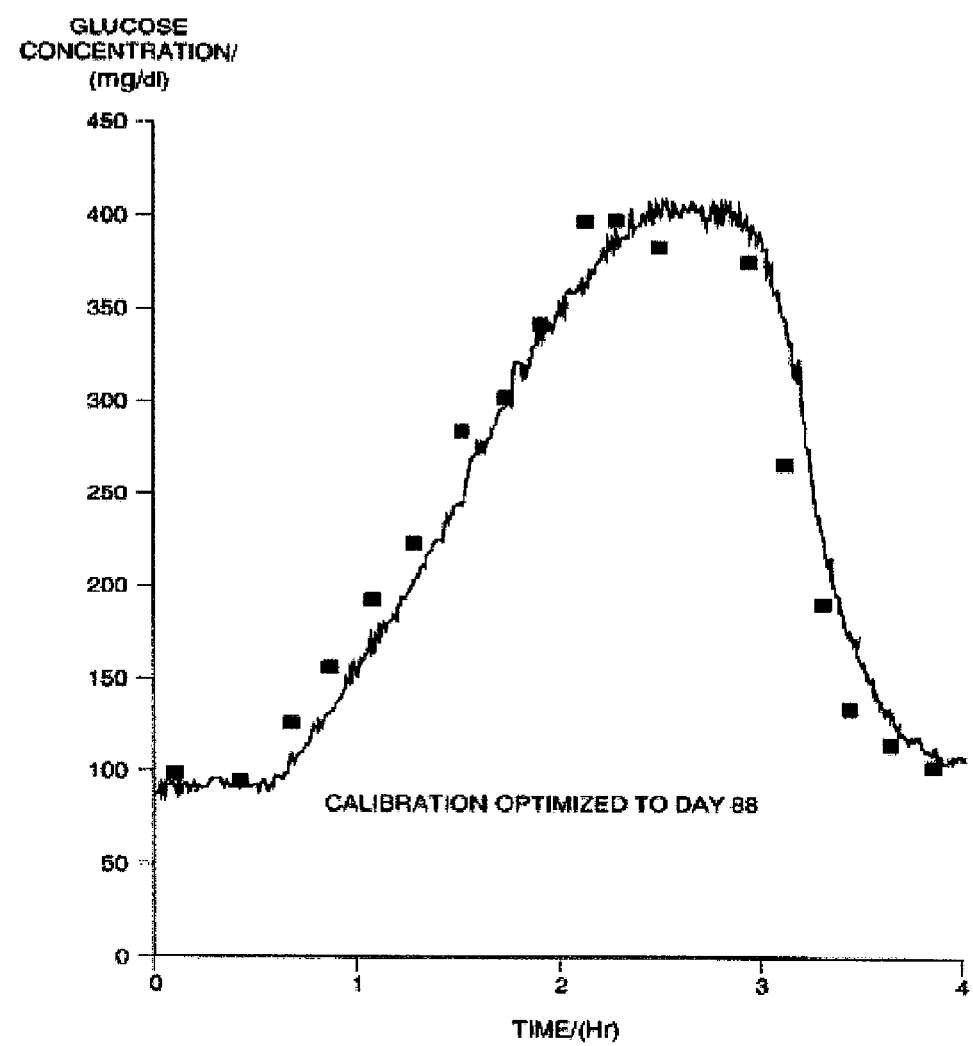
Figure 9C:
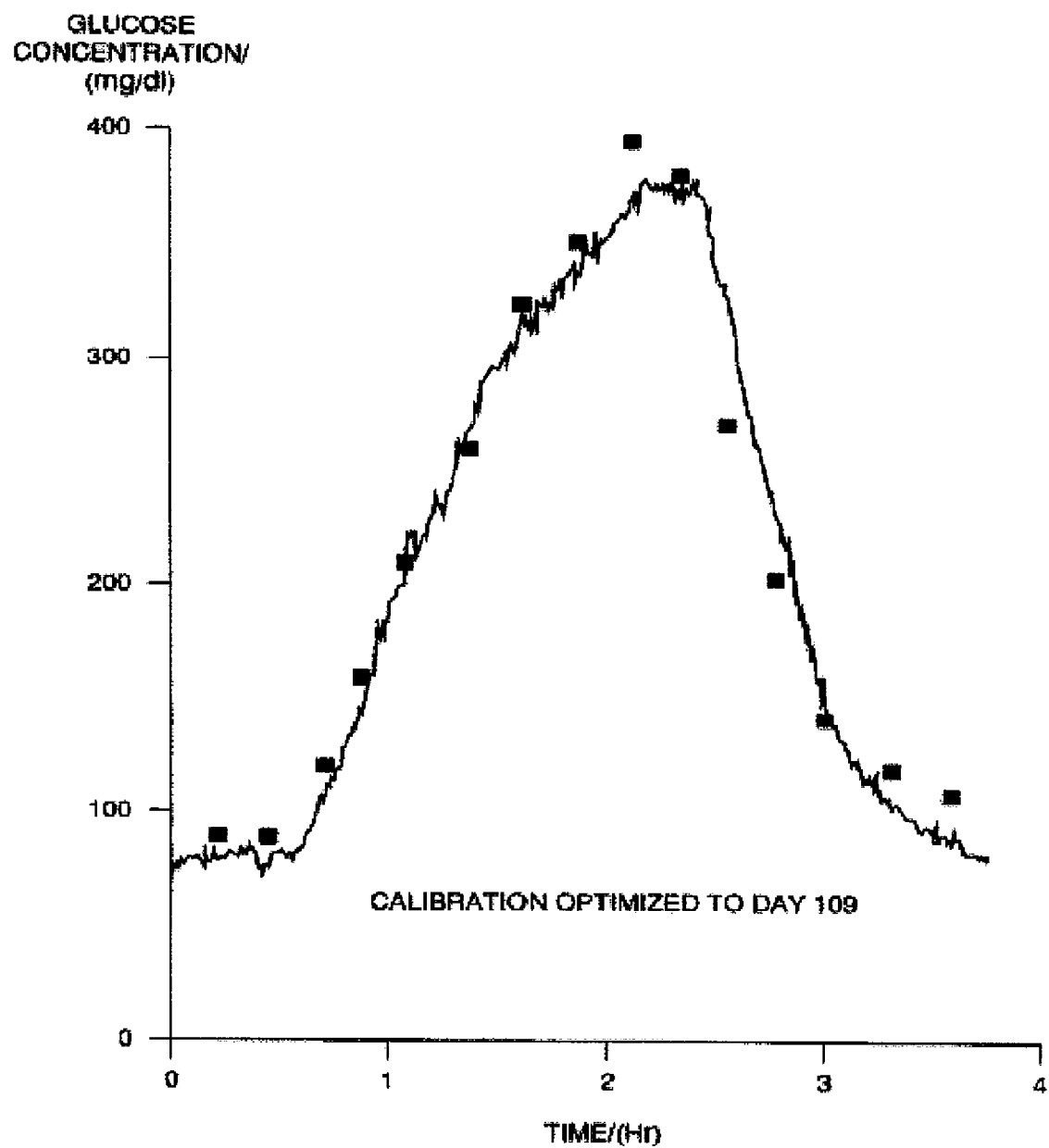

Typical Glucose Infusion Studies: The six sensor devices were tracked for 20-150 days and were evaluated using the octreotide-glucose infusion protocol. FIGS. 9A, 9B, and 9C graphically depict three in vivo sensor response curves (using best case calibration factors) plotted in conjunction with the reference blood glucose values for Sensor 1903 at post-implant times of 25, 88, and 109 days; this data is representative of the data obtainable with the sensor devices of the preferred embodiments. Referring to FIGS. 9A-C, the arrow labeled "#1" indicates octreotide injection, the arrow labeled "#2" indicates the turning on of the glucose infusion pump, and the arrow labeled "#3" indicates the turning off of this pump. The 90% response time for this sensor over its lifetime ranged from 5-to-10 minutes and was 5 minutes for the data shown. Such time responses are adequate, since changes in diabetic patients occur at slower rates than used with infusion protocols.

Figure 10:
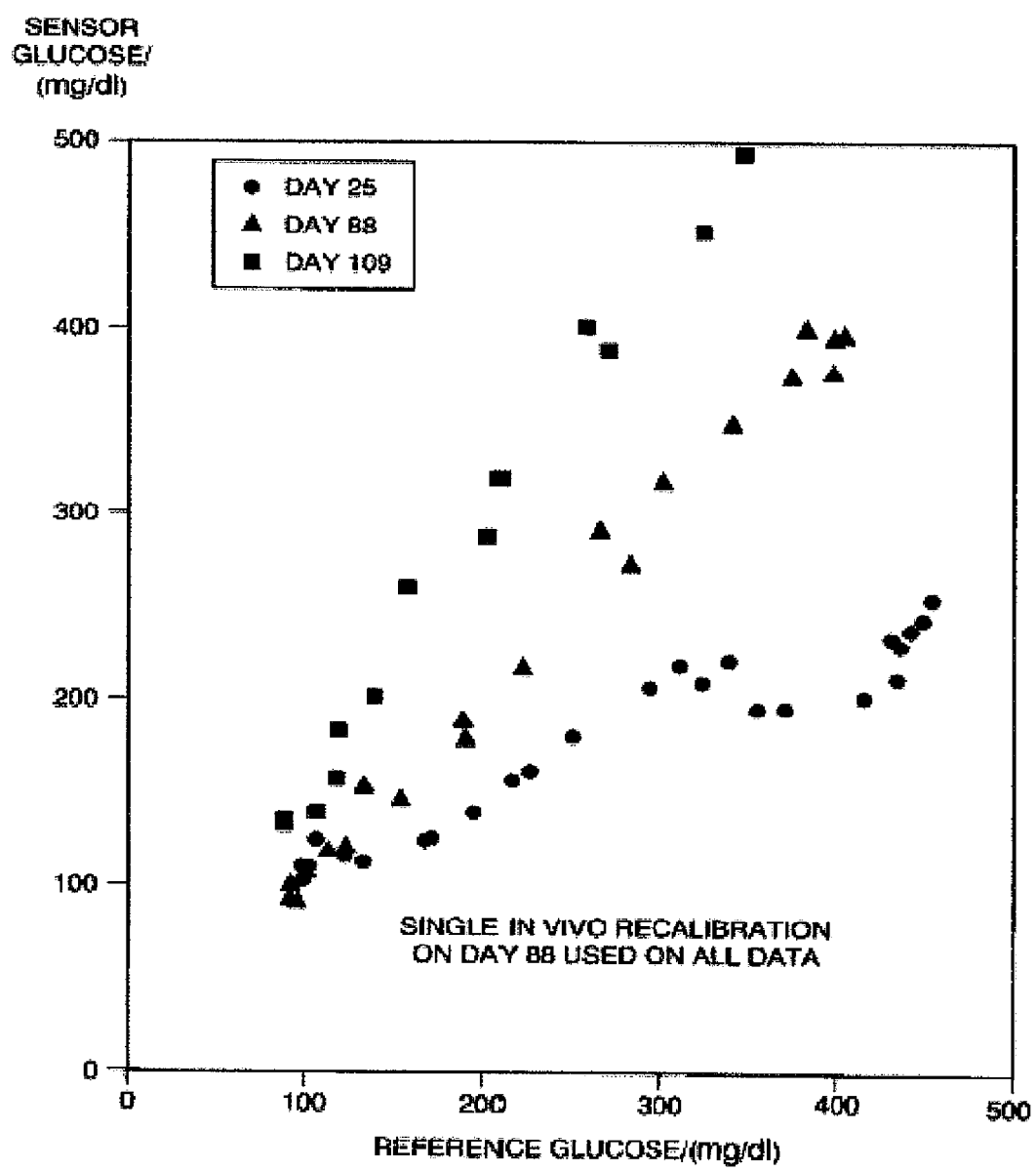
FIG. 10 graphically depicts sensor glucose versus reference glucose for one device of a preferred embodiment using the single set of calibration factors from day 88 of FIG. 5B.

FIG. 10 graphically depicts sensor glucose versus reference glucose (for Sensor 1903) using the single set of calibration factors from day 88. As depicted in FIG. 10, when sensor glucose is plotted versus reference glucose, the changes in sensor calibration over the lifetime of the sensor become apparent. These changes are reflected primarily in the output sensitivity to a known glucose concentration step while the zero current remained quite stable. The results suggest that in vivo recalibration every month would be preferred for this sensor to provide optimal glucose tracking.

Angiogenesis Stimulating Membrane Sensors vs. Control Membrane Sensors: Generally speaking, demonstration of improvement in a sensor can be judged by noting whether significant improvements in sensor start up time, increased yields of operating glucose sensors, extension of sensor lifetimes, and maintenance of calibration factors occurs. The lifetime of a glucose sensor can be defined as the time of first glucose sensing (in this case during a glucagon challenge) to the last glucose infusion study which provides correct glucose trends to concentration changes. All sensors showed glucose tracking and only one sensor showed a duration of less than 10 days. Average sensor lifetimes of 84±55 days were observed with the sensors containing the angiogenesis-stimulating membrane, values superior to the control sensors which only showed lifetimes of 35±10 days. In addition, one of the sensors incorporating the angiogenic membrane provided optimal data to 150 days.

Example 7

Preparation of Biointerface Membrane with Porous Silicone

A porous silicone cell disruptive (first) domain was prepared by mixing approximately 1 kg of sugar crystals with approximately 36 grams of water for 3-6 minutes. The mixture was then pressed into a mold and baked at 80° C. for 2 hours. The silicone was vacuumed into the mold for 6 minutes and cured at 80° C. for at least 2 hours. The sugar was dissolved using heat and deionized water, resulting in a flat sheet, porous membrane. Different architectures were obtained by varying the crystal size (crystals having an average diameter of about 90, 106, 150, 180, and 220 µm) and distribution within the mold that the silicone was cast from. After removal of silicone from the mold, the resulting membranes were measured for material thickness.

The cell-impermeable (second) domain was prepared by placing approximately 706 gm of dimethylacetamide (DMAC) into a 3 L stainless steel bowl to which a polycarbonate urethane solution (1325 g, CHRONOFLEX™ AR 25% solids in DMAC and a viscosity of 5100 cp) and polyvinylpyrrolidone (125 g, PLASDONE™ K-90D) were added. The bowl was then fitted to a planetary mixer with a paddle type blade and the contents were stirred for one hour at room temperature. The cell-impermeable domain coating solution was then coated onto a PET release liner (Douglas Hansen Co., Inc. (Minneapolis, Minn.)) using a knife over roll set at a 0.012" (305 µm) gap. This film was then dried at 305° F. (152° C.). The final film was approximately 0.0015" (38 µm) thick. The biointerface membrane was prepared by pressing the porous silicone onto the cast cell-impermeable domain.

The advantages of using porous silicone included the mechanical robustness of the material, the ability to mold it into various structural architectures, the ability to load lipid-soluble bioactive agents into the membrane without a carrier, the ability to fill the large pores of the material with collagen-coupled bioactive agents, and the high oxygen solubility of silicone that allowed the membrane to act as an oxygen antenna domain.

Various bioactive agents can be incorporated into the biomaterials of preferred embodiments. In some embodiments, such bioactive agent containing biomaterials can be employed in an implantable glucose device for various purposes, such as extending the life of the device or to facilitate short-term function. The following experiments were performed with a porous silicone biointerface membrane prepared as described above, in combination with bioactive agents, for the purpose of accelerated device initiation and long-term sustentation.

Example 8

Neovascularizing Agents in Biointerface Membranes

In this experiment, disks were employed, which were prepared for three-week implantation into the subcutaneous space of rats to test a neovascularizing agent. Monobutyrin was chosen based on its hydrophobic characteristics and ability to promote neovascularization. This experiment consisted of soaking the porous silicone prepared as described above in the concentrated solution of the bioactive compound at elevated temperature. This facilitated a partitioning of the agent into the porous silicone dependent upon its solubility in silicone rubber. Porous silicone disks were exposed to phosphate buffer mixed with Monobutyrin (500 mg/ml) for four days at 47° C. These disks were then autoclaved in the same solution, then rinsed in sterile saline immediately prior to implant. Disks were implanted into the subcutaneous dorsal space. Rats were euthanized and disks explanted at 3 weeks. Disks were fixed in 10% NBF and histologically processed and analyzed. The numbers of vessels per high power field were evaluated from porous silicone disks embedded with and without Monobutyrin after 3 weeks of implantation.

Figure 11:
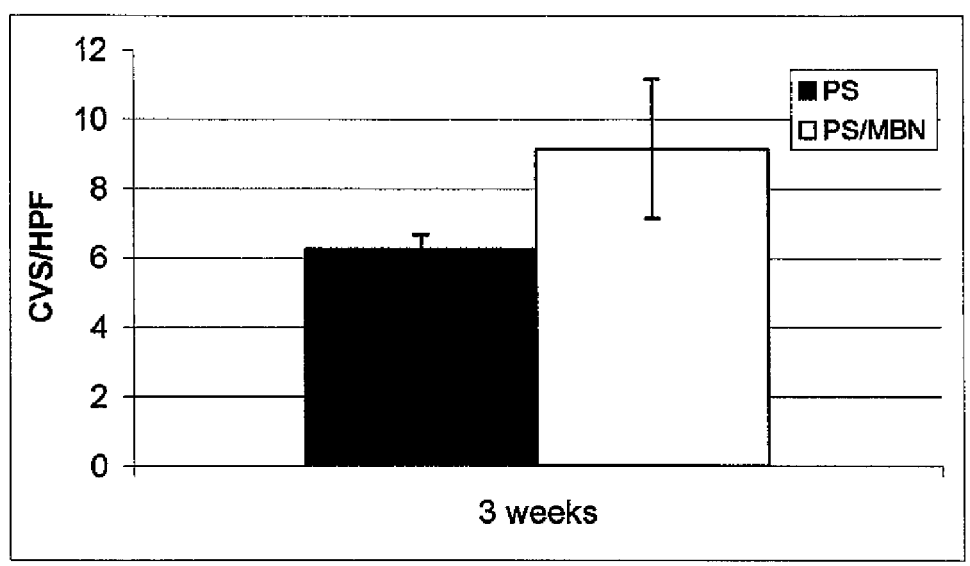
FIG. 11 is a bar graph that shows average number of vessels (per high-powered field of vision) of porous silicone materials embedded with Monobutyrin after three weeks of implantation.

FIG. 11 is a bar graph that shows average number of vessels (per high-powered field of vision) of porous silicone (PS) materials embedded with and without Monobutyrin (MBN) after three weeks of implantation. MBN was chosen because of its reported neovascularizing properties. See Halvorsen et al., *J. Clin. Invest.* 92(6):2872-6 (1993); Dobson et al., *Cell* 61(2)1 (1990); and English et al., *Cardiovasc. Res* 49(3):588-99. (2001). An overall increase in the numbers of vessels per high power field was seen with MBN as compared to porous silicone alone ($p<0.05$). These preliminary data suggested that bioactive agents absorbed into porous silicone can alter healing in the first month. It is believed that this increase in vessels results in improved device performance.

Example 9

Anti-Inflammatory Agents in Biointerface Membranes

Dexamethasone was loaded into a porous silicone biointerface membrane by sorption. In this experiment, 100 mg of Dexamethasone was mixed with 10 mL of Butanone (solvent) and the mixture heated to about 70° C.-80° C. to dissolve the Dexamethasone in the solvent. The solution was then centrifuged to ensure solubility. The supernatant was pipetted from the solution and placed in a clean glass vial. Disks of porous silicone were placed in the Dexamethasone solution at 40° C. for 5 days, after which the disks were air-dried. The disks were sprayed with 70% isopropanol to remove trapped air from the porous silicone, attached to glucose sensors, and sterilized in 0.5% glutaraldehyde for 24 hours. After rinsing, the glucose sensors were placed in a 40 mL phosphate buffer solution conical. These conicals were placed on a shaker table with a setting of about 7 or 8. Dexamethasone release in PBS solution was measured daily for the first five days and then every three days until the end of the experiment using a UV spectrometer. After each measurement when the absorbance was above 0.1, the PBS solution was changed to ensure that it did no reach its maximum solubility). The release kinetics are graphed on FIG. 12.

Figure 12:
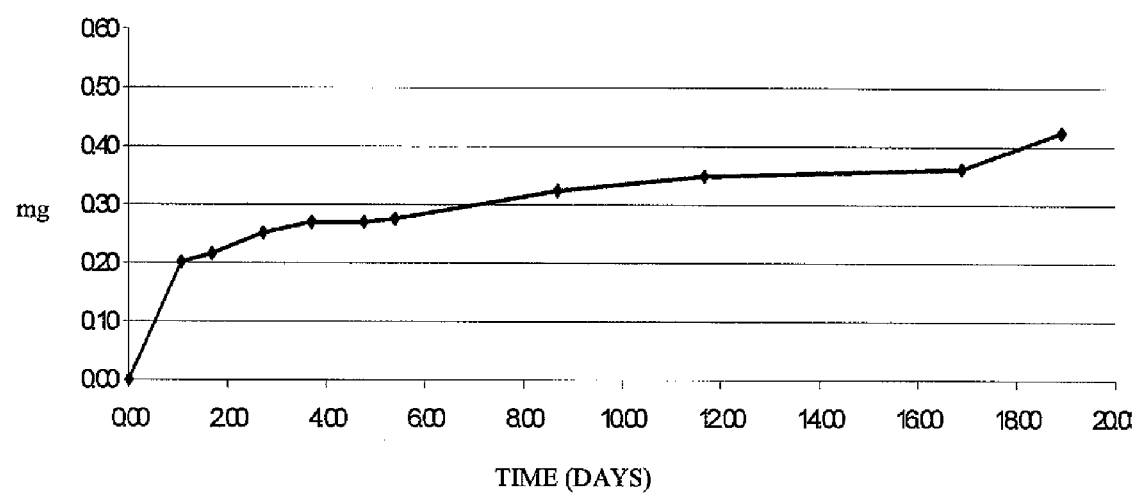
FIG. 12 is a graph that shows release kinetics over time in PBS solution for porous silicone with Dexamethasone incorporated therein.

FIG. 12 is a graph that shows the cumulative amount of Dexamethasone released over time as described above. Namely, during the first 19 days, about 0.4 mg of Dexamethasone was released in PBS solution. The amount of Dexamethasone released is at least partially dependent upon the surface area of the biointerface membrane, including throughout the cavities of the cell disruptive domain. While not wishing to be bound by theory, it is believed that Dexamethasone released over time can modify a tissue response to the biointerface membrane in vivo thereby 1) substantially overcoming the effects of a "sleep period", 2) aiding in prevention of barrier cell layer formation, and/or 3) rescuing a biointerface membrane from the negative effects associated with such acute inflammation, rendering adequate analyte transport to an implantable device.

Methods and devices that are suitable for use in conjunction with aspects of the preferred embodiments are disclosed in copending U.S. patent application Ser. No. 10/838,912 filed May 3, 2004 and entitled, "IMPLANTABLE ANALYTE SENSOR"; U.S. patent application Ser. No. 10/789,359 filed Feb. 26, 2004 and entitled, "INTEGRATED DELIVERY DEVICE FOR A CONTINUOUS GLUCOSE SENSOR"; U.S. application Ser. No. 10/685,636 filed Oct. 28, 2003 and entitled, "SILICONE COMPOSITION FOR BIOCOMPATIBLE MEMBRANE"; U.S. application Ser. No. 10/648,849 filed Aug. 22, 2003 and entitled, "SYSTEMS AND METHODS FOR REPLACING SIGNAL ARTIFACTS IN A GLUCOSE DEVICE DATA STREAM"; U.S. application Ser. No. 10/646,333 filed Aug. 22, 2003 entitled, "OPTIMIZED DEVICE GEOMETRY FOR AN IMPLANTABLE GLUCOSE DEVICE"; U.S. application Ser. No. 10/647,065 filed Aug. 22, 2003 entitled, "POROUS MEMBRANES FOR USE WITH IMPLANTABLE DEVICES"; U.S. application Ser. No. 10/633,367 filed Aug. 1, 2003 entitled, "SYSTEM AND METHODS FOR PROCESSING ANALYTE MEASURING-DEVICE DATA"; U.S. application Ser. No. 09/916,386 filed Jul. 27, 2001 and entitled "MEMBRANE FOR USE WITH IMPLANTABLE DEVICES"; U.S. application Ser. No. 09/916,711 filed Jul. 27, 2001 and entitled "SENSOR HEAD FOR USE WITH IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 10/153,356 filed May 22, 2002 and entitled "TECHNIQUES TO IMPROVE POLYURETHANE MEMBRANES FOR IMPLANTABLE GLUCOSE DEVICES"; U.S. application Ser. No. 09/489,588 filed Jan. 21, 2000 and entitled "DEVICE AND METHOD FOR DETERMINING ANALYTE LEVELS"; U.S. application Ser. No. 09/636,369 filed Aug. 11, 2000 and entitled "SYSTEMS AND METHODS FOR REMOTE MONITORING AND MODULATION OF MEDICAL DEVICES"; and U.S. application Ser. No. 09/916,858 filed Jul. 27, 2001 and entitled "DEVICE AND METHOD FOR DETERMINING ANALYTE LEVELS," as well as issued patents including U.S. Pat. No. 6,001,067 issued Dec. 14, 1999 and entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE."

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. All patents, applications, and other references cited herein are hereby incorporated by reference in their entirety.

What is claimed is:

1. A device for subcutaneous monitoring of glucose levels, comprising:
a housing;
a sensor; and
a porous biointerface layer for promoting long term microcirculatory delivery of glucose and oxygen to the sensor for a time period of at least about one month, wherein the porous biointerface layer comprises an architecture that supports tissue ingrowth and is configured to maintain sufficient fluid flow to the sensor for long term glucose measurement, wherein the porous biointerface layer further comprises a first bioactive agent configured to be released over a first time period of from about one day to about one month, wherein release of the first bioactive agent is configured to increase a rate at which the device becomes functional by at least partially overcoming sleep period effects associated with a temporary decrease in sensor sensitivity associated with tissue ingrowth into the porous biointerface layer; wherein the porous biointerface layer further comprises a second bioactive agent configured to be released over a second time period, wherein release of the second bioactive agent is configured to modulate a foreign body response to reduce a continual decline in sensor sensitivity over a life of a sensor.

2. The device of claim 1, wherein the biointerface layer comprises a material selected from the group consisting of hydrophilic polyvinylidene fluoride, mixed cellulose esters, polyvinyl chloride, polyvinyl alcohol, polyethylene, polytetrafluoroethylene, cellulose acetate, cellulose nitrate, polycarbonate, nylon, polyester, mixed esters of cellulose polyvinylidene difluoride, silicone, polyacrylonitrile, polypropylene, polysulfone, polymethacrylate, and mixtures thereof.

3. The device of claim 1, wherein the biointerface layer comprises expanded polytetrafluoroethylene.

4. The device of claim 1, wherein the biointerface layer comprises silicone.

5. The device of claim 1, wherein at least one of the first bioactive or the second bioactive agent is selected from the group consisting of anti-inflammatory agents, anti-infective agents, anesthetics, inflammatory agents, growth factors, immunosuppressive agents, antiplatelet agents, anticoagulants, ACE inhibitors, cytotoxic agents, anti-barrier cell compounds, vascularization-inducing compounds, anti-sense molecules, and mixtures thereof.

6. The device of claim 1, wherein at least one of the first bioactive agent or the second bioactive agent is an anti-inflammatory agent selected from the group consisting of nonsteroidal anti-inflammatory drugs (NTHEs), aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, tolmetin, corticosteroids, cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, dexamethasone, and mixtures thereof.

7. The device of claim 1, wherein at least one of the first bioactive agent or the second bioactive agent is an anti-infective agent selected from the group consisting of anthelmintics, mebendazole, antibiotics, aminoclycosides, gentamicin, neomycin, tobramycin, antifungal antibiotics, amphotericin b, fluconazole, griseofulvin, itraconazole, ketoconazole, nystatin, micatin, tolnaftate, cephalosporins, cefaclor, cefazolin, cefotaxime, ceftazidime, ceftriaxone, cefuroxime, cephalexin, beta-lactam antibiotics, cefotetan, meropenem, chloramphenicol, macrolides, azithromycin, clarithromycin, erythromycin, penicillins penicillin G sodium salt, amoxicillin, ampicillin, dicloxacillin, nafcillin, piperacillin, ticarcillin, tetracyclines, doxycycline, minocycline, tetracycline, bacitracin, clindamycin, colistimethate sodium, polymyxin b sulfate, vancomycin; antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine, quinolones, ciprofloxacin, levofloxacin, sulfonamides, sulfadiazine, sulfisoxazole, sulfones, dapsone, furazolidone, metronidazole, pentamidine, sulfanilamidum crystallinum, gatifloxacin, sulfamethoxazole/trimethoprim, and mixtures thereof.

* * * * *

UNITED STATES PATENT AND TRADEMARK OFFICE
CERTIFICATE OF CORRECTION

PATENT NO.         : 7,860,545 B2
APPLICATION NO.    : 12/037812
DATED              : December 28, 2010
INVENTOR(S)        : Shults et al.

Page 1 of 2

It is certified that error appears in the above-identified patent and that said Letters Patent is hereby corrected as shown below:

| Column | Line | |
|---|---|---|
| 5 | 6 | Change "betamethesone," to --betamethasone,--. |
| 5 | 16 | Change "aminoclycosides," to --aminoglycosides,--. |
| 5 | 44 | Change "xylocalne," to --xylocaine,--. |
| 7 | 19 | Change "betamethesone," to --betamethasone,--. |
| 7 | 28 | Change "aminoclycosides," to --aminoglycosides,--. |
| 7 | 55 | Change "xylocalne," to --xylocaine,--. |
| 14 | 20-21 | Change "diptheria/tetanus" to --diphtheria/tetanus--. |
| 14 | 27 | Change "perioxidase;" to --peroxidase;--. |
| 14 | 33 | Change "phenyloin," to --phenytoin;--. |
| 14 | 48 | Change "Trepenoma palladium," to --Treponema pallidum,--. |
| 14 | 49 | Change "stomatis" to --stomatitis--. |
| 15 | 3 | Change "(barbituates," to --(barbiturates,--. |
| 18 | 53 | Change "vivo" to --vivo,--. |
| 20 | 4 | Change "vivo" to --vivo,--. |
| 24 | 14 | Change "vivo" to --vivo,--. |
| 24 | 23 | Change "vivo" to --vivo,--. |
| 25 | 27 | Change "poly(l-lysine)," to --poly(1-lysine),--. |
| 25 | 28 | Change "hydroxyapeptite" to --hydroxyapatite--. |
| 28 | 7 | Change "SIP" to --S1P--. |

Signed and Sealed this
Eleventh Day of October, 2011

David J. Kappos
*Director of the United States Patent and Trademark Office*

| Col. | Line | Correction |
|---|---|---|
| 29 | 12 | Change "betamethesone," to --betamethasone,--. |
| 29 | 28 | Change "methothrexate," to --methotrexate,--. |
| 29 | 36 | Change "Cerivasttin)," to --Cerivastatin),--. |
| 29 | 44 | Change "aminoclycosides" to --aminoglycosides--. |
| 30 | 55 | Change "glenipin," to --genipin,--. |
| 36 | 29 | Change "geneic" to --generic--. |
| 39 | 19 (Approx.) | Change "(2H)," to --($2H^+$),--. |
| 43 | 51 | Change "tetrafluorethylene," to --tetrafluoroethylene,--. |
| 58 | 6 | Change "vivo" to --vivo,--. |
| 60 | 15 | In Claim 6, change "betamethesone," to --betamethasone,--. |
| 60 | 26 | In Claim 7, change "aminoclycosides," to --aminoglycosides,--. |